US011993803B2

(12) United States Patent
Brandt et al.

(10) Patent No.: US 11,993,803 B2
(45) Date of Patent: May 28, 2024

(54) MIXTURE COMPOSITION COMPRISING GLUCOLIPIDS

(71) Applicant: Evonik Operations GmbH, Essen (DE)

(72) Inventors: Kathrin Daniela Brandt, Düsseldorf (DE); Stefan Julian Liebig, Düsseldorf (DE); Hans Henning Wenk, Mülheim an der Ruhr (DE); Maciej Olek, Kahl (DE); Martin Schilling, Bonn (DE); Steffen Schaffer, Herten (DE); Mirja Wessel, Bochum (DE); Anne Jeremias, Wuppertal (DE)

(73) Assignee: Evonik Operations GmbH, Essen (DE)

(*) Notice: Subject to any disclaimer, the term of this patent is extended or adjusted under 35 U.S.C. 154(b) by 795 days.

(21) Appl. No.: 16/963,277

(22) PCT Filed: Feb. 8, 2019

(86) PCT No.: PCT/EP2019/053099
§ 371 (c)(1),
(2) Date: Jul. 20, 2020

(87) PCT Pub. No.: WO2019/154970
PCT Pub. Date: Aug. 15, 2019

(65) Prior Publication Data

US 2021/0371773 A1 Dec. 2, 2021

(30) Foreign Application Priority Data

Feb. 9, 2018 (EP) .................................... 18156045

(51) Int. Cl.
*C12P 7/00* (2006.01)
*C07K 14/195* (2006.01)
(Continued)

(52) U.S. Cl.
CPC .......... *C12P 7/6463* (2013.01); *C07K 14/195* (2013.01); *C11D 1/10* (2013.01);
(Continued)

(58) Field of Classification Search
CPC ................................... C11D 3/48; C11D 1/10
See application file for complete search history.

(56) References Cited

U.S. PATENT DOCUMENTS 3,234,258 A 2/1966 Louis
4,814,272 A * 3/1989 Wagner ................. C07H 15/04 435/100

(Continued)

FOREIGN PATENT DOCUMENTS

CA 2053900 A1 10/1990
DE 19648439 A1 5/1998

(Continued)

OTHER PUBLICATIONS

Brandt et al., U.S. Appl. No. 16/857,523, filed Apr. 24, 2020.

(Continued)

*Primary Examiner* — Necholus Ogden, Jr.
(74) *Attorney, Agent, or Firm* — Grüneberg and Myers PLLC

(57) ABSTRACT

The invention relates to a mixture composition comprising glucolipids, to its use for producing formulations and to formulations comprising this mixture composition.

12 Claims, 1 Drawing Sheet

Specification includes a Sequence Listing.

(51) Int. Cl.

| | |
|---|---|
| ***C11D 1/10*** | (2006.01) |
| ***C11D 3/48*** | (2006.01) |
| ***C12N 9/10*** | (2006.01) |
| ***C12N 15/52*** | (2006.01) |
| ***C12P 7/62*** | (2022.01) |
| ***C12P 7/6436*** | (2022.01) |
| ***C12P 7/6463*** | (2022.01) |

(52) U.S. Cl.
CPC .............. *C11D 3/48* (2013.01); *C12N 9/1051* (2013.01); *C12N 15/52* (2013.01); *C12P 7/62* (2013.01); *C12P 7/6436* (2013.01)

(56) References Cited

U.S. PATENT DOCUMENTS

| | | | | |
|---|---|---|---|---|
| 4,933,281 | A | 6/1990 | Daniels et al. | |
| 5,075,041 | A | 12/1991 | Lutz | |
| 5,417,879 | A * | 5/1995 | Hall | C11D 1/06 510/351 |
| 5,520,839 | A * | 5/1996 | Hall | C11D 1/825 536/123.13 |
| 7,202,063 | B1 * | 4/2007 | Gunther | C12N 1/20 435/123 |
| 8,466,248 | B2 | 6/2013 | Meyer et al. | |
| 8,911,982 | B2 | 12/2014 | Schaffer et al. | |
| 9,005,928 | B2 | 4/2015 | Schaffer et al. | |
| 9,068,211 | B2 | 6/2015 | Schaffer et al. | |
| 9,085,787 | B2 | 7/2015 | Schaffer et al. | |
| 9,102,968 | B2 | 8/2015 | Schaffer et al. | |
| 9,157,108 | B2 | 10/2015 | Schaffer et al. | |
| 9,243,212 | B2 | 1/2016 | Kuppert et al. | |
| 9,271,908 | B2 | 3/2016 | Allef et al. | |
| 9,351,485 | B2 | 5/2016 | Geissler-Blank et al. | |
| 9,434,755 | B2 | 9/2016 | Schilling et al. | |
| 9,580,720 | B2 | 2/2017 | Schaffer et al. | |
| 10,174,353 | B2 | 1/2019 | Thum et al. | |
| 10,292,924 | B2 | 5/2019 | Schilling et al. | |
| 10,370,493 | B2 | 8/2019 | Brandt et al. | |
| 10,544,384 | B2 | 1/2020 | Scheuermann et al. | |
| 10,604,722 | B2 | 3/2020 | Schilling et al. | |
| 10,618,867 | B2 | 4/2020 | Liebig et al. | |
| 10,676,495 | B2 | 6/2020 | Lu et al. | |
| 10,941,173 | B2 | 3/2021 | Lu et al. | |
| 10,988,713 | B2 | 4/2021 | Schilling et al. | |
| 11,254,896 | B2 | 2/2022 | Kuppert et al. | |
| 2007/0191292 | A1 * | 8/2007 | Gandhi | A61P 31/10 514/28 |
| 2012/0145956 | A1 | 6/2012 | Walden et al. | |
| 2014/0178444 | A1 * | 6/2014 | Stadler | A61P 31/10 424/59 |
| 2016/0045424 | A1 | 2/2016 | Schwab et al. | |
| 2016/0249604 | A1 | 9/2016 | Geissler-Blank et al. | |
| 2017/0094968 | A1 | 4/2017 | Sieverding | |
| 2017/0306264 | A1 | 10/2017 | Peggau et al. | |
| 2018/0023040 | A1 | 1/2018 | Schilling et al. | |
| 2018/0066297 | A1 | 3/2018 | Haas et al. | |
| 2018/0344602 | A1 | 12/2018 | Schuch et al. | |
| 2019/0040095 | A1 | 2/2019 | Lu et al. | |
| 2019/0233856 | A1 | 8/2019 | Thum et al. | |
| 2019/0269158 | A1 | 9/2019 | Schilling et al. | |
| 2019/0271020 | A1 | 9/2019 | Thum et al. | |
| 2019/0300728 | A1 | 10/2019 | Klostermann et al. | |
| 2019/0300917 | A1 | 10/2019 | Eckstein et al. | |
| 2019/0307657 | A1 | 10/2019 | Wenk et al. | |
| 2020/0199492 | A1 | 6/2020 | Xue et al. | |
| 2020/0207938 | A1 | 7/2020 | Klostermann et al. | |
| 2020/0214959 | A1 | 7/2020 | Lu et al. | |
| 2020/0407761 | A1 | 12/2020 | Wessel et al. | |
| 2021/0337835 | A1 | 11/2021 | Schilling et al. | |
| 2022/0186048 | A1 | 6/2022 | Reuter et al. | |
| 2022/0186075 | A1 | 6/2022 | Reuter et al. | |

FOREIGN PATENT DOCUMENTS

| | | | |
|---|---|---|---|
| DE | 10 2008 001 788.4 | | 11/2009 |
| DE | 10 2012 201 360 | A1 | 8/2013 |
| EP | 0 153 634 | B1 | 8/1989 |
| EP | 2 410 039 | A1 | 1/2012 |
| EP | 2 786 742 | A1 | 10/2014 |
| EP | 2 787 065 | A1 | 10/2014 |
| JP | S58/217598 | | 12/1983 |
| JP | S60-188092 | A | 9/1985 |
| JP | S64-13998 | A | 1/1989 |
| WO | 90/13533 | | 11/1990 |
| WO | 2011/157496 | A1 | 12/2011 |
| WO | 2012/010406 | A1 | 1/2012 |
| WO | 2014/197457 | A1 | 12/2014 |
| WO | 2015/091294 | A1 | 6/2015 |
| WO | 2021/180612 | A1 | 9/2021 |
| WO | 2021/190993 | A1 | 9/2021 |
| WO | 2022/017844 | A1 | 1/2022 |
| WO | 2022/233700 | A1 | 11/2022 |

OTHER PUBLICATIONS

International Search Report mailed on Mar. 19, 2019 in PCT/EP2019/053099 (5 pages).

Written Opinion mailed on Mar. 19, 2019 in PCT/EP2019/053099 (6 pages).

T. Matsuyama et al., "Surface-active novel glycolipid and linked 3-hydroy fatty acids produced by Serratia rubidaea," copyright Jun. 1990, Journal of Bacteriology, vol. 172, No. 6, pp. 3015-3022 (8 pages).

Ahmad Mohammad Abdel-Mawgoud et al., "Rhamnolipids: diversity of structures, microbial origins and roles," copyright Mar. 2010, Applied Microbiology and Biotechnology, vol. 86, No. 5, pp. 1323-1336 (14 pages).

Kleinen et al., U.S. Appl. No. 17/436,104, filed Sep. 3, 2021.

D. Schulz, et al., "Marine Biosurfactants, I. Screening for Biosurfactants among Crude Oil Degrading Marine Microorganisms from the North Sea", 1991, pp. 197-203.

* cited by examiner

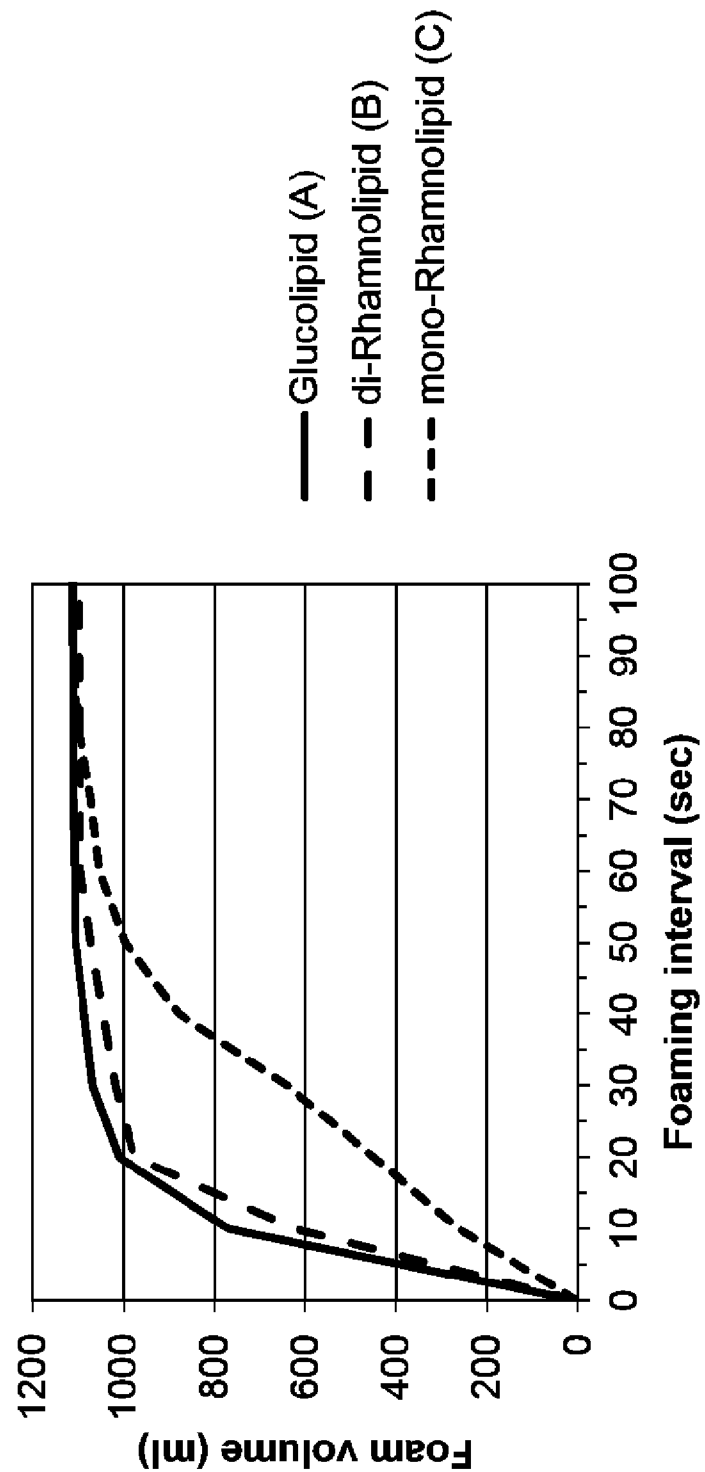
Glucolipid (A)
di-Rhamnolipid (B)
mono-Rhamnolipid (C)
Foam volume (ml)
1200
1000
800
600
400
200
0
0 10 20 30 40 50 60 70 80 90 100
Foaming interval (sec)

MIXTURE COMPOSITION COMPRISING GLUCOLIPIDS

CROSS REFERENCE TO RELATED APPLICATIONS

This application is a 35 U.S.C. § 371 U.S. national phase entry of International Application No. PCT/EP2019/053099 having an international filing date of Feb. 8, 2019, which claims the benefit of European Application No. 18156045.9 filed Feb. 9, 2018, each of which is incorporated herein by reference in its entirety.

FIELD

The invention relates to a mixture composition comprising glucolipids, to its use for producing formulations and to formulations comprising this mixture composition.

BACKGROUND

EP2787065 discloses formulations comprising rhamnolipids, where the content of di-rhamnolipids is bigger than the content of mono-rhamnolipids, and that the excess of di-rhamnolipids increases the rate of foam formation and/or for foam stabilization.

Matsuyama T., Tanikawa T., Nakagawa Y. (2011) *Serrawettins and Other Surfactants Produced by Serratia*. In: Soberón-Chávez G. (eds) Biosurfactants. Microbiology Monographs, vol 20. Springer, Berlin, Heidelberg disclose a structure of rubiwettin RG1 to be beta-D-glucopyranosyl 3-(3'-hydroxytetradecanoyloxy)decanoate.

DE19648439 discloses mixtures used for the preparation of washing-up liquids comprising glycolipids and surfactants.

SUMMARY

It was an object of the invention to provide bio-based compositions which have the same advantages as di-rhamnolipids, while having a simpler structure and/or lower molecular weight.

BRIEF DESCRIPTION OF THE DRAWING

The FIGURE shows a graph of foam volume of different lipids vs. time.

DETAILED DESCRIPTION

Surprisingly, it has been found that the mixture composition described below is able to achieve the object addressed by the invention.

The present invention therefore provides mixture compositions comprising certain glucolipids in defined weight ratios.

The present invention further provides formulations comprising the mixture compositions according to the invention.

One advantage of the mixture compositions according to the invention is their excellent foam stability under aqueous conditions.

A further advantage of the mixture compositions according to the invention is their outstanding foam volume under aqueous conditions.

A further advantage of the mixture compositions according to the invention is their exceptional foaming behavior.

A further advantage of the mixture compositions according to the invention is their simple formulatability in any desired aqueous surface-active systems.

A further advantage of the mixture compositions according to the invention is their good thickenability with conventional thickeners in formulations.

A further advantage is their good ability to wash off skin and hair.

A further advantage of the mixture compositions according to the invention is their mildness and good physiological compatibility, in particular characterized by a high value in the red blood cell (RBC) test.

A further advantage is their good skin feel during and after washing.

A further advantage of the mixture compositions according to the invention is that they leave behind a soft skin feel after washing.

A further advantage of the mixture compositions according to the invention is that they leave behind a smooth skin feel after washing.

A further advantage of the mixture compositions according to the invention is that they have a refatting effect on the skin.

A further advantage of the mixture compositions according to the invention is that they can be synthesized essentially free from oil.

A further advantage is that the mixture compositions according to the invention can be produced with higher space-time yield, higher carbon yields, and higher product concentration than di-rhamnolipids.

In connection with the present invention, the term "glucolipid" is understood as meaning compounds of the general formula (I) or salts thereof, formula (I)

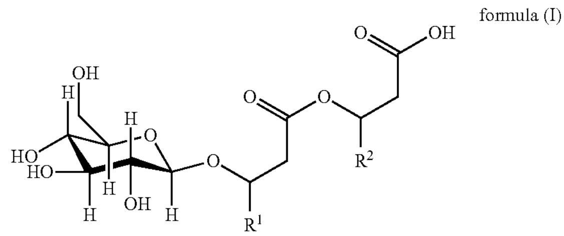

where m=1 or 0, $R^1$ and $R^2$=independently of one another identical or different organic radical having 2 to 24 carbon atoms, in particular optionally branched, optionally substituted, in particular hydroxy-substituted, optionally unsaturated, in particular optionally mono-, di- or tri-unsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12.

Distinct glucolipids are abbreviated according to the following nomenclature:

"GL-CXCY" is understood as meaning glucolipids of the general formula (I) in which one of the radicals $R^1$ and $R^2$=$(CH_2)_o$—$CH_3$ where o=X−4 and the remaining radical $R^1$ or $R^2$=$(CH_2)_o$—$CH_3$ where o=Y−4.

The nomenclature used thus does not differentiate between "CXCY" and "CYCX".

If one of the aforementioned indices X and/or Y is provided with ":Z", then this means that the respective radical $R^1$ and/or $R^2$=an unbranched, unsubstituted hydrocarbon radical with X−3 or Y−3 carbon atoms having Z double bonds.

In connection with the present invention, the "pH" is defined as the value which is measured for a corresponding substance at 25° C. after stirring for five minutes using a pH electrode calibrated in accordance with ISO 4319 (1977).

In connection with the present invention, the term "aqueous medium" is understood as meaning a composition which comprises at least 5% by weight of water, based on the total composition under consideration.

Unless stated otherwise, all the stated percentages (%) are percentages by mass.

The present invention provides a mixture composition comprising glucolipids of the general formula (I) or salts thereof

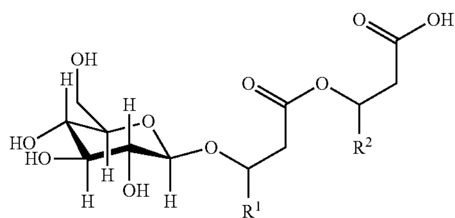

formula (I), where $R^1$ and $R^2$=independently of one another identical or different organic radical having 2 to 24 carbon atoms, characterized in that the mixture composition comprises at least 51% by weight to preferably 98% by weight, preferably 60% by weight to 95% by weight, more preferably 70% by weight to 90% by weight, particularly preferably 75% by weight to 85% by weight, glucolipids GL-C10C10 of the general formula (I) with $R^1$ and $R^2$=$(CH_2)_6$—$CH_3$, where the percentages by weight refer to the sum of all of the glucolipids of the general formula (I) present.

A preferred mixture composition according to the invention is characterized in that the pH of the mixture composition at 25° C. is from 3.5 to 9, preferably from 5 to 7 and particularly preferably from 5.6 to 6.6.

The glucolipids present in the mixture composition according to the invention are present at least partially as salts on account of the given pH.

In preferred mixture compositions according to the invention the cations of the glucolipid salts present are selected from the group comprising, preferably consisting of, $Li^+$, $Na^+$, $K^+$, $Mg^+$, $Ca^+$, $Al^+$, $NH_4^+$, primary ammonium ions, secondary ammonium ions, tertiary ammonium ions and quaternary ammonium ions.

Exemplary representatives of suitable ammonium ions are tetramethylammonium, tetraethylammonium, tetrapropylammonium, tetrabutylammonium and [(2-hydroxyethyl) trimethylammonium] (choline) and also the cations of 2-aminoethanol (ethanolamine, MEA), diethanolamine (DEA), 2,2',2"-nitrilotriethanol (triethanolamine, TEA), 1-aminopropan-2-ol (monoisopropanolamine), ethylenediamine, diethylenetriamine, triethylenetetramine, tetraethylenepentamine, 1,4-diethylenediamine (piperazine), aminoethylpiperazine and aminoethylethanolamine.

The mixtures of the abovementioned cations may also be present as cations of the glucolipid salts present according to the invention.

Particularly preferred cations are selected from the group comprising, preferably consisting of, $Na^+$, $K^+$, $NH_4^+$ and the triethanolammonium cation.

It may be advantageous and is therefore preferred if the mixture composition according to the invention comprises 1% by weight to 30% by weight, preferably 5% by weight to 25% by weight, particularly preferably 10% by weight to 20% by weight, of GL-C8C10, where the percentages by weight refer to the sum of all of the glucolipids of the general formula (I) present.

A preferred mixture composition according to the invention is characterized in that the mixture composition comprises 0.5% by weight to 20% by weight, preferably 3% by weight to 17% by weight, particularly preferably 5% by weight to 15% by weight, of GL-C10C12:1, where the percentages by weight refer to the sum of all of the glucolipids of the general formula (I) present.

A further preferred mixture composition according to the invention is characterized in that the mixture composition comprises 0.5% by weight to 20% by weight, preferably 2% by weight to 15% by weight, particularly preferably 3% by weight to 12% by weight, of GL-C10C12 where the percentages by weight refer to the sum of all of the glucolipids of the general formula (I) present.

A particularly preferred mixture composition according to the invention is characterized in that the mixture composition comprises 1% by weight to 30% by weight, preferably 5% by weight to 25% by weight, particularly preferably 10% by weight to 20% by weight, of GL-C8C10, 0.5% by weight to 20% by weight, preferably 3% by weight to 17% by weight, particularly preferably 5% by weight to 15% by weight, of GL-C10C12:1, 0.5% by weight to 20% by weight, preferably 2% by weight to 15% by weight, particularly preferably 3% by weight to 12% by weight, of GL-C10C12 where the percentages by weight refer to the sum of all of the glucolipids of the general formula (I) present.

A very particularly preferred mixture composition according to the invention is characterized in that the mixture composition comprises 10% by weight to 20% by weight, of GL-C8C10, 5% by weight to 15% by weight, of GL-C10C12:1, 3% by weight to 12% by weight, of GL-C10C12 where the percentages by weight refer to the sum of all of the glucolipids of the general formula (I) present.

Over and above this, it is preferred if the mixture composition according to the invention comprises glucolipids of the formula GL-CX in only small amounts. In particular, the mixture composition according to the invention comprises preferably 0% by weight to 5% by weight, preferably 0.01% by weight to 4% by weight, particularly preferably 0.1% by weight to 3% by weight, of GL-C10, where the percentages by weight refer to the sum of all of the glucolipids of the general formula (I) present.

The mixture composition according to the invention preferably contains at least 60% by weight, preferably at least 80% by weight, particularly preferably at least 90% by weight, of glucolipids of the general formula (I), where the percentages by weight refer to the total dry mass of the overall mixture composition.

The term "total dry mass" in the context of the present invention is understood to mean the portion of the mixture composition according to the invention which remains— naturally in addition to water—after the mixture composition according to the invention has been freed of the components which are liquid at 25° C. and 1 bar.

The mixture compositions according to the invention can advantageously be incorporated into cosmetic formulations in particular.

Consequently, a further subject matter of the present invention is the use of the mixture compositions according to the invention for producing formulations, in particular cosmetic formulations, and also the formulations, in particular cosmetic formulations, which comprise the mixture composition according to the invention.

The formulation according to the invention preferably contains 0.5% by weight to 20% by weight, preferably 2% by weight to 15% by weight, particularly preferably 3% by weight to 12% by weight, of glucolipids of the general formula (I), where the percentages by weight refer to the overall formulation.

Besides the mixture compositions according to the invention, preferred formulations according to the invention comprise at least—next to the glucolipid—one further surfactant, it being possible to use, for example, anionic, nonionic, cationic and/or amphoteric surfactants. Preferably, from an applications-related point of view, preference is given to mixtures of anionic and nonionic surfactants. The total surfactant content of the formulation is preferably 5 to 60% by weight and particularly preferably 15 to 40% by weight, based on the total formulation.

The nonionic surfactants used are preferably alkoxylated, advantageously ethoxylated, in particular primary alcohols having preferably 8 to 18 carbon atoms and on average 1 to 12 mol of ethylene oxide (EO) per mol of alcohol, in which the alcohol radical can be linear or preferably 2-position methyl-branched or can contain linear and methyl-branched radicals in a mixture, as are customarily present in oxo alcohol radicals. In particular, however, alcohol ethoxylates with linear radicals from alcohols of native origin having 12 to 18 carbon atoms, for example from coconut, palm, tallow fat or oleyl alcohol, and on average 2 to 8 EO per mol of alcohol are preferred. The preferred ethoxylated alcohols include, for example, C12-C14-alcohols with 3 EO, 4 EO or 7 EO, C9-C11-alcohol with 7 EO, C13-C15-alcohols with 3 EO, 5 EO, 7 EO or 8 EO, C12-C18-alcohols with 3 EO, 5 EO or 7 EO and mixtures of these, such as mixtures of C12-C14-alcohol with 3 EO and C12-C18-alcohol with 7 EO. The stated degrees of ethoxylation are statistical average values which can be an integer or a fraction for a specific product. Preferred alcohol ethoxylates have a narrowed homolog distribution. In addition to these nonionic surfactants, it is also possible to use fatty alcohols with more than 12 EO. Examples thereof are tallow fatty alcohol with 14 EO, 25 EO, 30 EO or 40 EO. Nonionic surfactants which contain EO and PO (propylene oxide) groups together in the molecule can also be used. In this connection, it is possible to use block copolymers with EO-PO block units or PO-EO block units, but also EO-PO-EO copolymers or PO-EO-PO copolymers.

It is of course also possible to use mixed alkoxylated nonionic surfactants in which EO and PO units are not distributed blockwise, but randomly. Such products are obtainable as a result of the simultaneous action of ethylene oxide and propylene oxide on fatty alcohols.

Furthermore, alkyl glycosides can also be used as further nonionic surfactants.

A further class of preferably used nonionic surfactants, which are used either as the sole nonionic surfactant or in combination with other nonionic surfactants, are alkoxylated, preferably ethoxylated or ethoxylated and propoxylated fatty acid alkyl esters, preferably having 1 to 4 carbon atoms in the alkyl chain, in particular fatty acid methyl esters, as are described for example in the Japanese patent application JP 58/217598 or which are preferably prepared by the process described in the international patent application WO-A-90/13533.

Nonionic surfactants of the amine oxide type, for example N-cocoalkyl-N,N-dimethylamine oxide and N-tallowalkyl-N,N-dihydroxyethylamine oxide, and of the fatty acid alkanolamide type may also be suitable. The amount of these nonionic surfactants is preferably not more than that of the ethoxylated fatty alcohols, in particular not more than half thereof.

Further suitable surfactants are polyhydroxy fatty acid amides; the polyhydroxy fatty acid amides are substances which can usually be obtained by reductive amination of a reducing sugar with ammonia, an alkylamine or an alkanolamine and subsequent acylation with a fatty acid, a fatty acid alkyl ester or a fatty acid chloride.

The anionic surfactants used are, for example, those of the sulphonate and sulphate type. Suitable surfactants of the sulphonate type here are preferably C9-C13-alkylbenzenesulphonates, olefinsulphonates, i.e. mixtures of alkene- and hydroxyalkanesulphonates, and also disulphonates, as are obtained, for example, from C12-C18-monoolefins with a terminal or internal double bond by sulphonation with gaseous sulphur trioxide and subsequent alkaline or acidic hydrolysis of the sulphonation products. Also of suitability are alkanesulphonates which are obtained from C12-C18-alkanes, for example by sulphochlorination or sulphoxidation with subsequent hydrolysis or neutralization. Similarly, the esters of $\alpha$-sulpho fatty acids (ester sulphonates), for example the $\alpha$-sulphonated methyl esters of hydrogenated coconut, palm kernel or tallow fatty acids, are also suitable.

Further suitable anionic surfactants are sulphated fatty acid glycerol esters. Fatty acid glycerol esters are to be understood as meaning the mono-, di- and triesters, and also mixtures thereof, as are obtained in the preparation by esterification of a monoglycerol with 1 to 3 mol of fatty acid or in the transesterification of triglycerides with 0.3 to 2 mol of glycerol. Preferred sulphated fatty acid glycerol esters here are the sulphation products of saturated fatty acids having 6 to 22 carbon atoms, for example of caproic acid, caprylic acid, capric acid, myristic acid, lauric acid, palmitic acid, stearic acid or behenic acid.

Preferred alk(en)yl sulphates are the alkali metal and in particular the sodium salts of the sulphuric acid half-esters of the C12-C18-fatty alcohols, for example from coconut fatty alcohol, tallow fatty alcohol, lauryl, myristyl, cetyl or stearyl alcohol or the C10-C20-oxo alcohols and those half-esters of secondary alcohols of these chain lengths. Furthermore, preference is given to alk(en)yl sulphates of the specified chain length which contain a synthetic straight-chain alkyl radical prepared on a petrochemical basis, and which have an analogous degradation behavior to the suitable compounds based on fatty chemical raw materials. From the point of view of washing, the C12-C16-alkyl sulphates and C12-C18-alkyl sulphates and also C14-C18-alkyl sulphates are preferred. 2,3-Alkyl sulphates, which are prepared for example in accordance with the U.S. Pat. No. 3,234,258 or 5,075,041 and can be obtained as commercial products of the Shell Oil Company under the name DAN®, are also suitable anionic surfactants.

The sulphuric acid monoesters of the straight-chain or branched C7-C20-alcohols ethoxylated with 1 to 6 mol of ethylene oxide, such as 2-methyl-branched C9-C11-alcohols having on average 3.5 mol of ethylene oxide (EO) or C12-C18-fatty alcohols with 1 to 4 EO, are also suitable. On account of their high foaming behavior, they are used in cleaning compositions only in relatively small amounts, for example in amounts of from 1 to 5% by weight.

Further suitable anionic surfactants are also the salts of alkylsulphosuccinic acid, which are also referred to as sulphosuccinates or as sulphosuccinic acid esters and constitute the monoesters and/or diesters of sulphosuccinic acid with alcohols, preferably fatty alcohols and in particular ethoxylated fatty alcohols. Preferred sulphosuccinates contain C8-C18-fatty alcohol radicals or mixtures of these. Particularly preferred sulphosuccinates contain a fatty alcohol radical which is derived from ethoxylated fatty alcohols. In this connection, sulphosuccinates whose fatty alcohol radicals are derived from ethoxylated fatty alcohols with a narrow homolog distribution are particularly preferred in turn. It is likewise also possible to use alk(en)ylsuccinic acid having preferably 8 to 18 carbon atoms in the alk(en)yl chain or salts thereof.

Particularly preferred anionic surfactants are soaps. Also of suitability are saturated and unsaturated fatty acid soaps, such as the salts of lauric acid, myristic acid, palmitic acid, stearic acid, (hydrogenated) erucic acid and behenic acid, and also soap mixtures derived in particular from natural fatty acids, for example coconut, palm kernel, olive oil or tallow fatty acid. The anionic surfactants including the soaps can be in the form of their sodium, potassium or ammonium salts, as well as soluble salts of organic bases, such as mono-, di- or triethanolamine. Preferably, the anionic surfactants are in the form of their sodium or potassium salts, in particular in the form of the sodium salts.

Amphoteric surfactants which can be used according to the invention are those surface-active compounds which carry at least one quaternary ammonium group and at least one —$COO^-$— or —$SO_3^-$ group in the molecule. Particularly preferred amphoteric surfactants in this connection are betaine surfactants such as alkyl- or alkylamidopropylbetaines. In particular, betaines such as the N-alkyl-N,N-dimethylammonium glycinates, e.g. the cocoalkyldimethylammonium glycinate, N-acylaminopropyl-N,N-dimethylammonium glycinates, e.g. the cocoacylaminopropyldimethylammonium glycinate, the C12-C18-alkyldimethylacetobetaine, the cocoamidopropyldimethylacetobetaine, 2-alkyl-3-carboxymethyl-3-hydroxyethylimidazolines and sulphobetaines having in each case 8 to 18 carbon atoms in the alkyl or acyl group, and also the cocoacylaminoethylhydroxyethylcarboxymethyl glycinate are preferred here. A particularly preferred zwitterionic surfactant is the N,N-dimethyl-N-(lauroylamidopropyl)ammoniumacetobetaine known under the INCI name Cocamidopropyl Betaine.

Further suitable amphoteric surfactants are formed by the group of amphoacetates and amphodiacetates, in particular, for example, coco- or laurylamphoacetates or -diacetates, the group of amphopropionates and amphodipropionates, and the group of amino acid-based surfactants such as acyl glutamates, in particular disodium cocoyl glutamate and sodium cocoyl glutamate, acyl glycinates, in particular cocoyl glycinates, and acyl sarcosinates, in particular ammonium lauroyl sarcosinate and sodium cocoyl sarcosinate.

Furthermore, the formulations according to the invention can comprise at least one additional component selected from the group of emollients,
emulsifiers,
thickeners/viscosity regulators/stabilizers,
UV photoprotective filters,
antioxidants,
hydrotropes (or polyols),
solids and fillers,
film formers,
pearlescent additives,
deodorant and antiperspirant active ingredients,
insect repellents,
self-tanning agents,
preservatives,
conditioners,
perfumes,
dyes,
odor absorbers,
cosmetic active ingredients,
care additives,
superfatting agents,
solvents.

Substances which can be used as exemplary representatives of the individual groups are known to the person skilled in the art and can be found for example in the German application DE 102008001788.4. This patent application is hereby incorporated by reference and thus forms part of the disclosure.

As regards further optional components and the amounts of these components used, reference is made expressly to the relevant handbooks known to the person skilled in the art, for example K. Schrader, "Grundlagen and Rezepturen der Kosmetika [Fundamentals and Formulations of Cosmetics]", 2nd edition, page 329 to 341, Hüthig Buch Verlag Heidelberg.

The amounts of the respective additives are dependent on the intended use.

Typical guide formulations for the respective applications are known prior art and are contained for example in the brochures of the manufacturers of the respective base materials and active ingredients. These existing formulations can generally be adopted unchanged. If required, however, the desired modifications can be undertaken without complication by means of simple experiments for the purposes of adaptation and optimization.

The mixture compositions according to the invention and the formulations according to the invention comprising the mixture composition according to the invention can advantageously be used for the cleaning of surfaces. In this form of the use according to the invention, the surface is preferably the surface of a living being, in particular of a person, with such surfaces particularly preferably being selected from skin and hair. In the context of the inventive use on the surface of a living being, the inventive use is a non-therapeutic use, preferably a cosmetic use.

The examples listed below describe the present invention by way of example without any intention of limiting the invention, the scope of application of which arises from the entire description and the claims, to the embodiments specified in the examples.

The following FIGURES form part of the description:

The FIGURE: Foam volume of different lipids vs. time

EXAMPLES

Example 1: Construction of an Expression Vector for the *P. aeruginosa* Gene rhlA and *S. rubidaea* Gene rbwB For the heterologous expression of the gene rhlA (SEQ ID NO: 3) from *P. aeruginosa* and rbwB (SEQ ID NO: 1) from *S. rubidaea* the plasmid pACYC_rhlA_Pa rbwB_Srub was constructed.

The synthetic operon consisting of rhlA_Pa (SEQ ID NO: 7) which encodes a 3-(3-hydroxyalkanoyloxy)alkanoic acid (HAAs) synthase (RhlA, SEQ ID NO: 4) and a glucosyltransferase (RbwB, SEQ ID NO: 2), respectively, was cloned under the control of the rhamnose inducible promoter Prim into the vector pACYCATh-5. Downstream of the synthetic operon a terminator sequence is located. The genes were amplified from genomic DNA of *P. aeruginosa* and *S. rubidaea* respectively via PCR. The $P_{Rha}$ promoter cassette (SEQ ID NO: 5) and the terminator sequence (SEQ ID NO: 6) were amplified from *E. coli* K12 genomic DNA. The vector is based on pACYC184 (New England Biolabs, Frankfurt/Main, Germany) and carries a p15A origin of replication for *E. coli* and a pVS1 origin of replication for the replication in *P. putida* KT2440. The pVS1 origin comes from the *Pseudomonas* plasmid pVS1 (Itoh Y, Watson J M, Haas D, Leisinger T, Plasmid 1984, 11(3), 206-20). rhlA and rbwB were fused via cross-over PCR to generate an optimized operon. For amplification the Phusion™ High-Fidelity Master Mix from New England Biolabs (Frankfurt/Main, Germany) was used according to manufacturer's manual. In the next step the fusion construct was cloned into the vector pACYCATh-5 using the restriction sites ApaI/PspXI. The ligated product was transformed into chemically competent *E. coli* DH5a cells (New England Biolabs, Frankfurt/Main, Germany). Procedure of PCR purification, cloning and transformation were carried out according to manufacturer's manual. The correct insertion of the target genes was checked by restriction analysis and the authenticity of the introduced DNA fragments was verified by DNA sequencing. The resulting plasmid was named pACYC_rhlA_Pa rbwB_Srub (SEQ ID NO: 8).

The *P. putida* strain KT2440 was transformed with the plasmid pACYC_rhlA_Pa rbwB_Srub by means of electroporation (Iwasaki K, et al., *Biosci. Biotech. Biochem.* 1994. 58(5):851-854)) and plated onto LB-agar plates supplemented with kanamycin (50 μg/mL). Transformants were checked for the presence of the correct plasmid by plasmid preparation and analytic restriction analysis. The resulting strain was named BS-PP-368 (*P. putida* KT2440 pACYC_rhlA_Pa rbwB_Srub).

Example 2: Production of Glucolipid with Strain BS-PP-368 (*P. putida* KT2440 pACYC_rhlA_Pa rbwB_Srub)

For the production of glucolipid the DASGIP® parallel bioreactor system from Eppendorf (Hamburg, Germany) was used. The fermentation was performed using 1 L reactors. pH and pO2 were measured online for process monitoring. OTR/CTR measurements served for estimating the metabolic activity and cell fitness, inter alia.

The pH electrodes were calibrated by means of a two-point calibration using standard solutions of pH 4.0 and pH7.0, as specified in DASGIP's technical instructions. The reactors were equipped with the necessary sensors and connections as specified in the technical instructions, and the agitator shaft was fitted. The reactors were then filled with 300 ml water and autoclaved for 20 min at 121° C. to ensure sterility. The pO2 electrodes were connected to the measuring amplifiers and polarized overnight (for at least 6 h). Thereafter, the water was removed under a clean bench and replaced by fermentation medium (2.2 g/L $(NH_4)_2SO_4$, 0.02 g/L NaCl, 0.4 g/L $MgSO_4 \times 7H_2O$, 0.04 g/L $CaCl_2) \times 2H_2O$, sterilized separately: 2 g/L $KH_2PO_4$, 8.51 g/L $KH_2PO_4$, 20 g/L glucose, 10 mL/L trace elements solution M12 (sterile-filtered: 0.2 g/L $ZnSO_4 \times 7$ $H_2O$, 0.1 g/L $MnCl_2 \times 4H_2O$, 1.5 g/L $Na_3$-Citrat×2 $H_2O$, 0.1 g/L $CuSO_4 \times 5$ $H_2O$, 0.002 g/L $NiCl_2 \times 6$ $H_2O$, 0.003 g/L $Na_2MoO_4 \times 2$ $H_2O$, 0.03 g/L $H_3BO_3$, 1 g/L $FeSO_4 \times 7$ $H_2O$). Thereafter, the pO2 electrodes were calibrated to 100% with a one-point calibration (stirrer: 600 rpm/aeration 10 sl/h air), and the feed, correction agent and induction agent lines were cleaned by "cleaning in place" as specified in the technical instructions. To this end, the tubes were rinsed first with 70% ethanol, then with 1 M NaOH, then with sterile fully-demineralized water and, finally, filled with the respective media.

Using the *P. putida* strain BS-PP-368, 25 ml LB1 medium (10 g/L tryptone, 5 g/L yeast extract, 1 g/L NaCl, pH 7.0) supplemented with kanamycin (50 μg/mL) in a baffeled shake flask were inoculated with 100 μl of a glycerol stock solution and incubated for ~18 h over night at 30° C. and 200 rpm. The first preculture was used to inoculate 50 ml seed medium (autoclaved: 4.4 g/L $Na_2HPO_4$*2 $H_2O$, 1.5 g/L $KH_2PO_4$, 1 g/L $NH_4Cl$, 10 g/L yeast extract, sterilized separately: 20 g/L glucose, 0.2 g/L $MgSO_4$*7 $H_2O$, 0.006 g/L $FeCl_3$, 0.015 g/L $CaCl_2$), 1 ml/L trace elements solution SL6 (sterile-filtered: 0.3 g/L $H_3BO_3$, 0.2 g/L $CoCl_2 \times 6$ $H_2O$, 0.1 g/L $ZnSO_4 \times 7$ $H_2O$, 0.03 g/L $MnCl_2 \times 4H_2O$, 0.01 g/L $CuCl_2 \times 2$ $H_2O$, 0.03 g/L $Na_2MoO_4 \times 2$ $H_2O$, 0.02 g/L $NiCl_2 \times 6$ $H_2O$) in a 500 ml baffeled shake flask (starting $OD_{600}$ 0.2). The culture were incubated for ~7 h at 200 rpm and 30° C. In order to inoculate the reactors with an optical density of 0.7, the $OD_{600}$ of the second preculture stage was measured and the amount of culture required for the inoculation was calculated.

The required amount of culture was added with the help of a 30 ml syringe through a septum into the heat-treated and aerated reactor.

The standard program shown in Table 1 is used:

TABLE 1

Standard program used for heated and aerated reactor a)

| DO controller | | pH controller | |
|---|---|---|---|
| Preset | 0% | Preset | 0 mL/h |
| P | 0.1 | P | 5 |
| Ti | 300 s | Ti | 200 s |
| Min | 0% | Min | 0 mL/h |
| Max | 100% | Max | 40 mL/h |

TABLE 1-continued

Standard program used for heated and aerated reactor b)

| N (Rotation) | From | To | XO2 (gas mixture) | from | to | F (gas flow) | from | to |
|---|---|---|---|---|---|---|---|---|
| Growth and biotransformation | 0%<br>500 rpm | 40%<br>1500 rpm | Growth and biotransformation | 0%<br>21% | 100%<br>21% | Growth and biotransformation | 35%<br>9 sl/h | 100%<br>72 sL/h |

c)

| Script | |
|---|---|
| Trigger fires | 31% DO (1/60 h) |
| Temperature | 37° C. |
| Induction rhamnose | 3 h after the feed start |
| Feed trigger | 50% DO |
| Feed rate | 1.5 [mL/h] |

The pH was adjusted unilaterally to pH 7.0 with 12.5% strength ammonia solution. During the growth phase and the biotransformation, the dissolved oxygen (pO2 or DO) in the culture was adjusted to at least 30% via the stirrer speed and the aeration rate. After the inoculation, the DO dropped from 100% to these 30%, where it was maintained stably for the remainder of the fermentation.

The fermentation was carried out as a fed batch. The feed starts with a 2.5 g/L*h glucose feed, composed of 500 g/L glucose, and was triggered via the DO peak which indicates the end of the batch phase. 3 h after the feed start, the expression of glucolipid production was induced with 0.2% (w/v) rhamnose. The inducer concentration referred to the volume at the beginning of fermentation. For both sugars stock solution of 220 g/L was used. The production of glucolipid started with the induction. At specified time points samples were taken from the fermenter to determine the concentration of glucolipids produced. After 65 h fermentation 11.1 g/L glucolipid was produced.

Example 3: HPLC-Based Quantification of Glucolipids

Quantification of glucolipids was carried out by means of HPLC. Using a displacement pipette (Combitip), 900 µl of 70% (v/v) n-propanol was introduced into a 2 ml reaction vessel and the reaction vessel was immediately closed for minimization of evaporation. The addition of 100 µl fermentation broth followed. After shaking for 1 min in a Retsch mill at a frequency of 30 Hz, the resulting crude extract mixture was centrifuged for 5 min at 13,000 rpm, and 8000 of the clear supernatant was transferred into an HPLC vial. Further dilutions of cell broth were carried out in 55% (v/v) propanol. Samples were stored at −20° C. before measurement.

For the detection and quantification of lipids an evaporation light scattering detector (Sedex LT-ELSD Model 85LT) was used. The measurement was carried out by means of Agilent Technologies 1200 Series (Santa Clara, Calif.) and a Zorbax SB-C8 Rapid Resolution column (4.6×150 mm, 3.5 µm, Agilent). The injection volume was 5.0 µl and the run time was 20 min. Mobile phase A: aqueous 0.1% TFA (trifluoracetic acid, solution); mobile phase B: methanol. The column temperature was 40° C. The ELSD (detector temperature 60° C.) and the DAD (diode array, 210 nm) were used as detectors.

| | t [min] | | Flow [1 ml/min] |
|---|---|---|---|
| Gradient: | 0.00 | 70% | 1.00 |
| | 15.00 | 100% | 1.00 |
| | 15.01 | 70% | 1.00 |
| | 20.00 | 70% | 1.00 |

Table 2. Gradient of mobile phases of A and B over time

The gradient used starts with 70% B in A to 100% B within 15 minutes at a flow rate of 1 mL/min followed by 5 minutes of re-equilibration with 70% B in A (see Table 2). Reference materials were used whose identity and purity were checked by HPLC-MS/MS and NMR.

The product of example 2 has a composition as described below and is called "production example 1" from now on:

GL-C10C10: 63.7%,
GL-C8C10: 15.5%,
GL-C10C12:1: 7.9%,
GL-C10C12: 6.6%,
GL-C8C8: 1.8%,
GL-C10C10:1: 1.3%
GL-C12C12:1: 1.1%
GL-C12C12: 0.8%
GL-C10: 1.3%

Example 4: Evaluation of Foaming Properties Using the SITA Foam Tester

Foamability of surfactants and surfactant based products is an important consumer-perceived attribute. Fast flash foaming and high foam volumes are indications to the consumers that the product is an efficacious quality product. Both parameters can be determined using the "SITA foam tester R-2000" measuring device from SITA Messtechnik GmbH. In this device, foam is generated by introducing air into a defined volume of a surfactant solution through a special rotor. The total volume of liquid and resulting foam is measured over time by means of a computer controlled sensing technique.

Using this method, production example 1 (A) was evaluated for its foamability in comparison to a composition of di-Rhamnolipids (B) and a composition of mono-Rhamnolipids (C), both bearing a comparable fatty acid substitution.

(B) and (C) are prepared by means of preparative column chromatography.

For this 10 g of freeze-dried RL mixture (JBR 505, Jeneil Biosurfactants, initially~5% by weight total rhamnolipid concentration) are dissolved in 5% by weight concentration in water-saturated ethyl acetate which comprises 1% by weight of acetic acid. 750 g of a silica 60 gel (200-500 μm; 35-70 mesh; Sigma-Aldrich, Germany) are suspended in water-saturated ethyl acetate (acidified with 1% by weight of acetic acid) and poured into a column (diameter=65 mm, maximum fill level=600 mm, 11 solvent reservoir). 2-3 cm of acid-treated sea sand (Riedel de Haen, Seelze, Germany) are coated as protective layer over the stationary phase. The eluent used is likewise water-saturated ethyl acetate which comprises 1% by weight of acetic acid. The rhamnolipid solution is placed onto the prepared column. The eluent flow rate is adjusted to 15 ml/min. The eluate is collected in 100 ml fractions and analysed by means of thin-film chromatography and HPLC. The mono- and di-rhamnolipid forms can be separated this way. Fractions of identical composition are combined and the solvent is stripped off on a rotary evaporator. Then, the residue is dissolved in water and freeze-dried. In order to obtain adequate amounts, this procedure is carried out several times. The purity of the resulting fractions is determined as >99% by weight by means of $^{1}$H-NMR and HPLC.

The composition produced in example 2 (A) and the rhamnolipids (B) and (C) were each diluted to a concentration of 0.5% active surfactant matter with water of a total hardness of 10° dH (German hardness). The pH of each test solution was adjusted to 6.0. 300 ml of each test solution were then tested for their foamability at 30° C. using a constant stirring speed of 1500 rpm for 10 sec. A total of 10 such measurement intervals were carried out for each test solution. The FIGURE illustrated the foam volume over time for each test solution:

Measurement parameters: temperature: 30° C.±0.5° C.; sample volume/measurement: 300 ml; concentration of test sample: 0.5% in water; water: 10° dH (=german hardness), pH: 6, stirring speed: 1500 rpm; stirring time: 10 sec; number of intervals: 10; number Surprisingly, as seen in the FIGURE, the composition according to the invention (A) shows the best performance in the SITA foam test, as it shows the fastest flash foaming and generates the highest foam volumes in the SITA foam test.

Production example 1 (A) performs very much better than the composition of mono-rhamnolipids (C), and also to lesser extent but still significantly better than the composition of di-Rhamnolipids (B). This finding is very surprising as there is a much greater structural similarity between (A) and (C) than between (A) and (B).

Example 5: Example Formulations

The following examples are for the purpose of illustration and are not to be construed as limitations of the present invention since many variations thereof are possible without departing from its scope.

The example formulations are made using conventional methods. If necessary, the pH value is adjusted by addition of either aqueous sodium hydroxide or citric acid at the end of the manufacturing process.

The term "Glucolipid" as used in the example formulations always refers to production example 1.

The term "Glycolipids" as used in the example formulations always refers to Rhamnolipids, which are commercially available as Rheance One from Evonik Nutrition & Care GmbH.

Shampoo

Example Formulation 1: Volume and Body Shampoo

| Ingredient | % |
|---|---|
| Aqua | ad 100 |
| Sodium Lauryl Sulfate | 7.0 |
| Sodium Laureth Sulfate | 5.0 |
| Cocamidopropyl Betaine | 2.0 |
| Glucolipid | 2.0 |
| Sodium Citrate | 1.5 |
| Sodium Xylenesulfonate | 1.5 |
| Sodium Chloride | 1.4 |
| Citric Acid | ad pH 5.5 |
| Sodium Levulinate, Sodium Benzoate | 1.0 |
| Hydroxypropyl Methylcellulose | 1.0 |
| Tetrasodium EDTA | 0.8 |
| Butylphenyl Methylpropional | 0.5 |
| Panthenol | 0.5 |
| Panthenyl Ethyl Ether | 0.3 |
| Linalool | 0.1 |
| Hexyl Cinnamal | 0.1 |
| Limonene | 0.1 |
| Benzyl Salicylate | 0.2 |
| Magnesium Nitrate | 0.1 |
| Magnesium Chloride | 0.1 |
| Methylchloroisothiazolinone | 0.1 |
| Dyes | q.s. |

Example Formulation 2: Repair Shampoo

| Ingredient | % |
|---|---|
| Aqua | ad 100 |
| Sodium Laureth Sulfate | 7.0 |
| Glycolipids | 3.0 |
| Glucolipid | 3.0 |
| Glycol Distearate | 2.5 |
| Cocamidopropyl Betaine | 2.0 |
| Sodium Citrate | 1.8 |
| Cocamide MEA | 1.8 |
| Sodium Xylenesulfonate | 1.5 |
| Dimethicone | 1.5 |
| Citric Acid | ad pH 5.0 |
| Sodium Benzoate | 0.7 |
| Polyquaternium-76 | 0.5 |
| Sodium Chloride | 0.9 |
| Glycerin | 0.5 |
| Tetrasodium EDTA | 0.3 |
| Butylphenyl Methylpropional | 0.2 |
| Hexyl Cinnamal | 0.1 |
| Linalool | 0.1 |
| alpha-Isomethyl Ionone | 0.1 |
| Geraniol | 0.2 |
| Hydrochloric Acid | 0.1 |
| Magnesium Nitrate | 0.1 |
| Methylchloroisothiazolinone | 0.1 |
| Magnesium Chloride | 0.1 |
| Methylisothiazolinone | 0.1 |
| Dyes | q.s. |

Example Formulation 3: Anti-Dandruff Shampoo

| Ingredient | % |
|---|---|
| Aqua | ad 100 |
| Sodium Laureth Sulfate | 6.0 |
| Sodium Lauryl Sulfate | 5.0 |
| Glucolipid | 4.0 |
| Cocamide MEA | 4.0 |
| Zinc Carbonate | 3.0 |
| Glycol Distearate | 2.5 |
| Dimethicone | 1.0 |
| Zinc Pyrithione | 1.0 |
| Sodium Chloride | 0.6 |

-continued

| Ingredient | % |
|---|---|
| Cetyl Alcohol | 0.8 |
| Guar Hydroxypropyltrimonium Chloride | 0.3 |
| Sodium Xylenesulfonate | 0.5 |
| Magnesium Sulfate | 0.7 |
| Sodium Benzoate | 0.7 |
| Ammonium Laureth Sulfate | 0.3 |
| Citric Acid | ad pH 4.5 |
| Benzyl Alcohol | 0.2 |
| Methylchloroisothiazolinone | 0.1 |
| Methylisothiazolinone | 0.1 |
| Parfum, Dyes | q.s. |

Example Formulation 4: Strengthening Shampoo

| Ingredient | % |
|---|---|
| Water | ad 100 |
| Sodium Lauryl Sulfate | 6.0 |
| Sodium Laureth Sulfate | 4.0 |
| Cocamidopropyl Betaine | 3.0 |
| Glucolipid | 3.0 |
| Glycol Distearate | 2.5 |
| Dimethicone | 2.0 |
| Sodium Citrate | 1.5 |
| Cocamide MEA | 1.0 |
| Sodium Xylenesulfonate | 1.0 |
| Citric Acid | ad pH 5.0 |
| Sodium Benzoate | 0.7 |
| Sodium Chloride | 0.8 |
| Tetrasodium EDTA | 0.3 |
| Polyquaternium-6 | 0.5 |
| Honey (Mel) | 0.5 |
| *Prunus Armeniaca* (Apricot) Fruit Extract | 0.5 |
| Methylchloroisothiazolinone | 0.1 |
| Methylisothiazolinone | 0.1 |
| Parfum, Dyes | q.s. |

Example Formulation 5: Shampoo

| Ingredient | % |
|---|---|
| Aqua | ad 100 |
| Sodium Laureth Sulfate | 9.0 |
| Cocamidopropyl Betaine | 3.0 |
| Glucolipid | 3.0 |
| Glycerin | 2.5 |
| Sodium Chloride | 1.7 |
| Glycol Distearate | 1.5 |
| Panthenol | 0.2 |
| Propylene Glycol | 0.3 |
| Hydroxypropyl Guar Hydroxypropyltrimonium Chloride | 0.3 |
| Sodium Benzoate | 0.7 |
| PEG-55 Propylene Glycol Oleate | 0.5 |
| Citric Acid | ad pH 5.5 |
| Hydrolyzed Wheat Protein | 0.3 |
| Argania Spinosa Kernel Oil | 0.1 |
| Laureth-4 | 0.5 |
| Potassium Sorbate | 0.2 |
| Parfum, Dyes | q.s. |

Example Formulation 6: Moisturising Shampoo

| Ingredient | % |
|---|---|
| Aqua | ad 100 |
| Sodium Laureth Sulfate | 8.0 |
| Cocamidopropyl Betaine | 3.0 |
| Sodium Chloride | 2.2 |
| Glucolipid | 2.0 |
| Hydrolyzed Keratin | 2.0 |

-continued

| Ingredient | % |
|---|---|
| Water Lily (*Nymphaea Odorata*) Root Extract | 1.8 |
| Aloe Barbadensis Leaf Juice | 1.5 |
| Glyceryl Glucoside | 1.0 |
| Panthenol | 1.0 |
| Sophorolipid | 1.0 |
| Polyquaternium-10 | 0.2 |
| Guar Hydroxypropyltrimonium Chloride | 0.3 |
| PEG-40 Hydrogenated Castor Oil | 0.7 |
| Glycerin | 0.5 |
| Citric Acid | ad pH 5.0 |
| Sodium Benzoate | 1.2 |
| Propylene Glycol | 1.0 |
| Citronellol | 0.1 |
| Limonene | 0.1 |
| alpha-Isomethyl Ionone | 0.1 |
| Benzyl Alcohol | 0.2 |
| Dyes | q.s. |

Example Formulation 7: Shampoo

| Ingredient | % |
|---|---|
| Aqua | ad 100 |
| Decyl Glucoside | 6.0 |
| Sodium Myreth Sulfate | 5.5 |
| Glucolipid | 3.0 |
| PEG-200 Hydrogenated Glyceryl Palmate | 2.5 |
| PEG-80 Sorbitan Laurate | 2.0 |
| PEG-90 Glycol Isostearate | 2.0 |
| Disodium PEG-5 Laurylcitrate Sulfosuccinate | 1.5 |
| Polyquaternium-10 | 1.2 |
| Hydrolyzed Silk | 1.2 |
| Laureth-2 | 1.2 |
| Citric Acid | ad pH 5.5 |
| Sodium Laureth Sulfate | 1.0 |
| PEG-40 Hydrogenated Castor Oil | 0.9 |
| Sodium Benzoate | 0.5 |
| Parfum, Dyes | q.s. |

Example Formulation 8: Cleansing Oil Shampoo

| Ingredient | % |
|---|---|
| Aqua | ad 100 |
| Sodium Laureth Sulfate | 7.0 |
| MIPA-Laureth Sulfate | 4.0 |
| Sodium Chloride | 3.2 |
| Cocamidopropyl Betaine | 3.0 |
| Glucolipid | 3.0 |
| Glycerin | 2.5 |
| PEG-18 Castor Oil Dioleate | 2.0 |
| Propylene Glycol | 2.0 |
| PEG-55 Propylene Glycol Oleate | 1.7 |
| Laureth-5 Carboxylic Acid | 1.0 |
| *Persea Gratissima* (Avocado) Oil | 1.0 |
| PPG-5-Ceteth-20 | 1.0 |
| Sodium Benzoate | 0.7 |
| Laureth-2 | 0.5 |
| Salicylic Acid | 0.3 |
| Linalool | 0.2 |
| alpha-Isomethyl Ionone | 0.1 |
| Limonene | 0.1 |
| *Zea Mays* (Corn) Germ Oil | 0.2 |
| Argania Spinosa Oil Kernel Oil | 0.1 |
| Camellia Oleifera Seed Oil | 0.1 |
| Sodium Hydroxide | 0.3 |
| Citric Acid | ad pH 5.0 |
| Parfum, Dyes | q.s. |

Example Formulation 9: Shine Shampoo

| Ingredient | % |
|---|---|
| Aqua | ad 100 |
| Ammonium Lauryl Sulfate | 5.5 |
| Glucolipid | 2.0 |
| Cocamidopropyl Betaine | 2.0 |
| Glycolipids | 2.0 |
| Sodium Chloride | 2.0 |
| Cocamide MEA | 2.0 |
| Nacre Powder | 1.0 |
| Sodium Benzoate | 0.7 |
| Hydroxypropyl Guar Hydroxypropyltrimonium Chloride | 0.7 |
| Hydroxypropyltrimonium Hydrolyzed Wheat Protein | 0.7 |
| Sodium Hydroxide | 0.2 |
| Salicylic Acid | 0.5 |
| Limonene | 0.1 |
| Benzoic Acid | 0.5 |
| Linalool | 0.3 |
| Benzyl Alcohol | 0.5 |
| Tin Oxide | 0.2 |
| alpha-Isomethyl Ionone | 0.1 |
| Acrylates Copolymer | 0.1 |
| Citric Acid | ad pH 5.5 |
| Citronellol | 0.1 |
| Hexyl Cinnamal | 0.1 |
| Dyes | q.s. |

Example Formulation 10: Shampoo

| Ingredient | % |
|---|---|
| Aqua | ad 100 |
| Sodium Cocoyl Isethionate | 3.5 |
| Sodium Lauryl Sulfoacetate | 3.5 |
| Di sodium Laureth Sulfosuccinate | 3.5 |
| Cocamidopropyl Betaine | 3.0 |
| Glucolipid | 3.0 |
| Sodium Lauroyl Sarcosinate | 1.0 |
| Glycol Distearate | 1.0 |
| C11-15 Pareth-7 | 1.0 |
| C12-13 Pareth-23 | 1.0 |
| C12-13 Pareth-3 | 1.0 |
| Decyl Glucoside | 1.0 |
| Tocopherol | 1.0 |
| Hydrogenated Coconut Acid | 1.0 |
| Sodium Chloride | 0.8 |
| Sodium Isethionate | 0.7 |
| Sodium Benzoate | 0.7 |
| Sodium Hydroxide | 0.3 |
| Phenoxyethanol | 0.6 |
| PPG-5 Ceteth-20 | 0.5 |
| PEG-55 Propylene Glycol Oleate | 0.5 |
| Trideceth-12 | 0.5 |
| Polyquaternium-7 | 0.5 |
| Polyquaternium-10 | 0.3 |
| Limonene | 0.1 |
| Benzoic Acid | 0.3 |
| Benzophenone-4 | 0.3 |
| Benzyl Salicylate | 0.2 |
| Linalool | 0.6 |
| Benzyl Alcohol | 0.6 |
| Amodimethicone | 0.5 |
| Propylene Glycol | 0.5 |
| Carbomer | 0.7 |
| *Rosmarinus Officinalis* (Rosemary) Leaf Oil | 0.7 |
| Methylparaben | 0.3 |
| Methylchloroisothiazolinone | 0.1 |
| Methylisothiazolinone | 0.1 |
| Citric Acid | ad pH 5.0 |
| Laureth-9 | 0.5 |
| Divinyldimethicone/Dimethicone Copolymer | 0.2 |
| Glycerin | 0.2 |
| Parfum, Dyes | q.s. |

Example Formulation 11: Reinforcing Shampoo

| Ingredient | % |
|---|---|
| Aqua | ad 100 |
| Sodium Laureth Sulfate | 6.0 |
| Dimethicone | 3.0 |
| Sodium Chloride | 3.0 |
| Coco-Betaine | 3.0 |
| Glucolipid | 2.0 |
| Sophorolipid | 1.0 |
| Glycol Distearate | 1.0 |
| Guar Hydroxypropyltrimonium Chloride | 0.3 |
| Cocamide MIPA | 0.5 |
| Sodium Benzoate | 0.7 |
| Hydroxypropyltrimonium Hydrolyzed Wheat Protein | 0.3 |
| Sodium Cocoate | 0.7 |
| Sodium Hydroxide | 0.6 |
| Arginine | 0.7 |
| Salicylic Acid | 0.5 |
| Limonene | 0.2 |
| Linalool | 0.2 |
| 2-Oleamido-1.3-Octadecanediol | 0.1 |
| Carbomer | 0.5 |
| Methyl Cocoate | 0.5 |
| Citric Acid | ad pH 5.0 |
| Hexylene Glycol | 0.2 |
| Hexyl Cinnamal | 0.1 |
| Glyceryl Linoleate | 0.1 |
| Glyceryl Oleate | 0.2 |
| Glyceryl Linolenate | 0.2 |
| Dyes | q.s. |

Example Formulation 12: Shampoo

| Ingredient | % |
|---|---|
| Aqua | ad 100 |
| Sodium Laureth Sulfate | 9.0 |
| Dimethicone | 3.5 |
| Sodium Chloride | 3.2 |
| Coco-Betaine | 3.0 |
| Glycol Distearate | 3.0 |
| Glucolipid | 2.0 |
| Guar Hydroxypropyltrimonium Chloride | 0.3 |
| Niacinamide | 0.1 |
| Cocamide MIPA | 2.0 |
| *Saccharum Officinarum* (Sugar Cane) Extract | 2.0 |
| Sodium Benzoate | 1.0 |
| Sodium Cocoate | 1.5 |
| Sodium Hydroxide | 0.6 |
| Salicylic Acid | 0.5 |
| Camellia Sinensis Extract/Camellia Sinensis Leaf Extract | 0.5 |
| Linalool | 0.2 |
| Benzyl Salicylate | 0.2 |
| *Pyrus Malus* (Apple) Fruit Extract | 0.3 |
| Carbomer | 0.5 |
| Pyridoxine HCl | 0.3 |
| *Persea Gratissima* (Avocado) Oil | 0.2 |
| Citric Acid | ad pH 5.5 |
| Butylphenyl Methylpropional | 0.1 |
| Methyl Cocoate | 0.3 |
| Hexylene Glycol | 0.1 |
| Hexyl Cinnamal | 0.1 |
| Dyes | q.s. |

Example Formulation 13: Fortifying Shampoo

| Ingredient | % |
|---|---|
| Aqua | ad 100 |
| Ammonium Lauryl Sulfate | 6.0 |
| Cocamidopropyl Betaine | 3.0 |
| Sodium Chloride | 2.7 |
| Glucolipid | 2.0 |

-continued

| Ingredient | % |
|---|---|
| Niacinamide | 0.1 |
| *Saccharum Officinarum* (Sugar Cane) Extract | 0.9 |
| *Cocos Nucifera* (Coconut) Oil | 0.9 |
| Sodium Benzoate | 0.9 |
| Hydroxypropyl Guar Hydroxypropyltrimonium Chloride | 0.1 |
| Sodium Hydroxide | ad pH |
| Salicylic Acid | 0.4 |
| Limonene | 0.1 |
| Benzoic Acid | 0.4 |
| Linalool | 0.3 |
| Cinnamyl Alcohol | 0.2 |
| *Pyrus Malus* (Apple) Fruit Extract | 0.5 |
| Pyridoxine HCl | 0.2 |
| Bisabolol | 0.2 |
| Citric Acid | ad pH 5.0 |
| Citronellol | 0.1 |
| Hexylene Glycol | 0.2 |
| Dyes | q.s. |

Example Formulation 14: Shampoo

| Ingredient | % |
|---|---|
| Aqua | ad 100 |
| Sodium Laureth Sulfate | 9.0 |
| Cocamidopropyl Betaine | 2.5 |
| Glucolipid | 2.5 |
| Sodium Chloride | 2.5 |
| Camellia Sinensis Leaf Extract | 2.0 |
| Guar Hydroxypropyltrimonium Chloride | 0.3 |
| Maltodextrin | 1.2 |
| Disodium EDTA | 1.0 |
| PPG-12 | 0.7 |
| Citric Acid | ad pH 5.0 |
| Sodium Hydroxide | 0.3 |
| Sodium Benzoate | 0.7 |
| Butylphenyl Methylpropional | 0.2 |
| Geraniol | 0.2 |
| Hexyl Cinnamal | 0.1 |
| Limonene | 0.1 |
| Linalool | 0.1 |
| Dyes | q.s. |

Example Formulation 15: Brunette Shampoo

| Ingredient | % |
|---|---|
| Aqua | ad 100 |
| Sodium Laureth Sulfate | 8.5 |
| Cocamidopropyl Betaine | 4.0 |
| Sodium Chloride | 3.5 |
| Glucolipid | 2.0 |
| Selaginella Lepidophylla Aerial Extract | 2.0 |
| Gluconolactone | 1.8 |
| Glycerin | 1.8 |
| Dimethiconol | 1.0 |
| Guar Hydroxypropyltrimonium Chloride | 0.5 |
| TEA-Dodecylbenzenesulfonate | 1.0 |
| Maltodextrin | 1.0 |
| Disodium EDTA | 0.7 |
| Carbomer | 0.9 |
| PPG-12 | 0.7 |
| Citric Acid | ad pH 5.5 |
| Sodium Hydroxide | 0.9 |
| TEA-Sulfate | 0.7 |
| Triethanolamine | 0.5 |
| DMDM Hydantoin | 0.1 |
| Sodium Benzoate | 0.7 |
| Methylchloroisothiazolinone | 0.1 |
| Methylisothiazolinone | 0.1 |
| alpha-Isomethyl Ionone | 0.1 |
| Butylphenyl Methylpropional | 0.2 |
| Hexyl Cinnamal | 0.1 |

-continued

| Ingredient | % |
|---|---|
| Limonene | 0.1 |
| Linalool | 0.1 |
| Dyes | q.s. |

Example Formulation 16: 2 in 1 Shampoo

| Ingredient | % |
|---|---|
| Aqua | ad 100 |
| Sodium Laureth Sulfate | 8.0 |
| PEG-200 Hydrogenated Glyceryl Palmate | 3.0 |
| Glucolipid | 3.0 |
| Di sodium Cocoamphodiacetate | 3.0 |
| Polysorbate 20 | 2.5 |
| Glycerin | 2.5 |
| Sodium Chloride | 2.0 |
| PEG-7 Glyceryl Cocoate | 2.0 |
| Sodium Benzoate | 1.0 |
| Sodium Laureth-8 Sulfate | 1.0 |
| Sodium Oleth Sulfate | 1.0 |
| Sodium Hydroxide | 0.3 |
| PPG-5 Ceteth-20 | 1.0 |
| PEG-55 Propylene Glycol Oleate | 0.5 |
| Polyquaternium-10 | 0.2 |
| Salicylic Acid | 0.3 |
| Maltodextrin | 0.2 |
| Propylene Glycol | 0.2 |
| Disodium Ricinoleamido MEA-Sulfosuccinate | 0.1 |
| Citric Acid | ad pH 5.5 |
| *Prunus Armeniaca* (Apricot) Kernel Oil | 0.1 |
| Parfum, Dyes | q.s. |

Example Formulation 17: Shampoo

| Ingredient | % |
|---|---|
| Aqua | ad 100 |
| Sodium Laureth Sulfate | 9.0 |
| Cocamidopropyl Betaine | 3.0 |
| Sodium Chloride | 2.5 |
| Glycol Distearate | 2.5 |
| Hydrolyzed Keratin | 2.0 |
| *Simmondsia Chinensis* (Jojoba) Seed Oil | 2.0 |
| Glucolipid | 2.0 |
| Argania Spinosa Kernel Oil | 0.5 |
| *Persea Gratissima* (Avocado) Oil | 0.5 |
| *Rosmarinus Officinalis* (Rosemary) Leaf Extract | 0.3 |
| *Helianthus Annuus* (Sunflower) Seed Oil | 0.3 |
| Cocamide MEA | 0.4 |
| Guar Hydroxypropyltrimonium Chloride | 0.2 |
| Polyquaternium-47 | 0.2 |
| PEG-20 Castor Oil | 0.5 |
| Phenethyl Benzoate | 0.7 |
| Disodium EDTA | 0.2 |
| Methylchloroisothiazolinone | 0.3 |
| Methylisothiazolinone | 0.3 |
| Benzyl Salicylate | 0.1 |
| Hexyl Cinnamal | 0.1 |
| Citronellol | 0.1 |
| Dyes | q.s. |

Example Formulation 18: Foam Shampoo

| Ingredient | % |
|---|---|
| Aqua | ad 100 |
| Sodium Laureth Sulfate | 5.0 |
| Isobutane | 5.0 |
| Decyl Glucoside | 5.0 |
| Propane | 3.5 |

-continued

| Ingredient | % |
|---|---|
| Sodium Cocoamphoacetate | 3.5 |
| Glucolipid | 3.5 |
| Glycolipids | 1.0 |
| Sophorolipid | 1.0 |
| Panthenol | 0.2 |
| Polyquaternium-10 | 0.2 |
| Hydroxypropyl Guar Hydroxypropyltrimonium Chloride | 0.1 |
| Sodium PCA | 0.5 |
| Octyldodecyl PCA | 0.5 |
| Maltodextrin | 0.5 |
| Tilia Cordata Flower Extract | 0.7 |
| Sodium Chloride | 0.9 |
| Citric Acid | ad pH 5.0 |
| Glycerin | 0.9 |
| Propylene Glycol | 0.3 |
| Butane | 0.7 |
| Sodium Acetate | 0.7 |
| Sorbitol | 0.5 |
| Isopropyl Alcohol | 0.5 |
| Dyes | q.s. |

Example Formulation 19: Anti-Dandruff Shampoo

| Ingredient | % |
|---|---|
| Aqua | ad 100 |
| Sodium Laureth Sulfate | 10.0 |
| Cocamidopropyl Betaine | 3.0 |
| Acrylates Copolymer | 2.5 |
| Sodium Lauroyl Glutamate | 2.5 |
| Zinc Pyrithione | 2.0 |
| Glucolipid | 2.0 |
| Piroctone Olamine | 0.7 |
| Hydroxypropyl Guar Hydroxypropyltrimonium Chloride | 0.2 |
| Propylene Glycol | 0.5 |
| Sodium PCA | 0.2 |
| *Citrus Medica Limonum* (Lemon) Peel Extract | 0.5 |
| Citric Acid | ad pH 5.0 |
| Glycol Distearate | 0.8 |
| PPG-9 | 0.2 |
| Laureth-4 | 0.2 |
| Sodium Chloride | 0.9 |
| Sodium Hydroxide | 0.3 |
| Sodium Naphthalenesulfonate | 0.7 |
| Sorbitol | 0.7 |
| DMDM Hydantoin | 0.1 |
| Sodium Benzoate | 0.8 |
| Limonene | 0.1 |
| Linalool | 0.1 |
| Butylphenyl Methylpropional | 0.1 |
| alpha-Isomethyl Ionone | 0.1 |
| Parfum, Dyes | q.s. |

Example Formulation 20: Shampoo

| Ingredient | % |
|---|---|
| Aqua | ad 100 |
| Sodium Laureth Sulfate | 5.0 |
| Disodium Cocoamphodiacetate | 2.0 |
| Glucolipid | 2.0 |
| Laureth-2 | 0.3 |
| Panthenol | 0.2 |
| Niacinamide | 0.1 |
| Sodium Chloride | 0.7 |
| Citric Acid | ad pH 5.0 |
| PEG-7 Glyceryl Cocoate | 0.5 |
| Sodium Benzoate | 0.5 |
| Polyquaternium-10 | 0.7 |
| Salicylic Acid | 0.5 |
| Hexyl Salicylate | 0.2 |
| Benzyl Salicylate | 0.1 |
| Hexyl Cinnamal | 0.1 |

-continued

| Ingredient | % |
|---|---|
| Linalool | 0.1 |
| Limonene | 0.1 |
| Propylene Glycol | 0.2 |
| Dyes | q.s. |

Example Formulation 21: Intensive Care Oil-Shampoo

| Ingredient | % |
|---|---|
| Aqua | ad 100 |
| Sodium Laureth Sulfate | 8.0 |
| Disodium Cocoamphodiacetate | 3.0 |
| Glucolipid | 2.5 |
| *Prunus Armeniaca* (Apricot) Kernel Oil | 2.5 |
| Hydrolyzed Keratin | 2.5 |
| Panthenol | 2.4 |
| Sodium Chloride | 2.2 |
| Citric Acid | ad pH 5.5 |
| Polyquaternium-10 | 0.5 |
| Sodium Benzoate | 0.5 |
| PEG-7 Glyceryl Cocoate | 0.7 |
| Laureth-2 | 0.4 |
| PEG-40 Hydrogenated Castor Oil | 0.4 |
| Propylene Glycol | 0.8 |
| PEG-55 Propylene Glycol Oleate | 0.7 |
| Hexyl Cinnamal | 0.1 |
| Butylphenyl Methylpropional | 0.2 |
| Benzyl Salicylate | 0.1 |
| Linalool | 0.2 |
| Benzyl Alcohol | 0.5 |
| Limonene | 0.1 |
| Sodium Acetate | 0.2 |
| Dyes | q.s. |

Example Formulation 22: Shampoo

| Ingredient | % |
|---|---|
| Aqua | ad 100 |
| Sodium Laureth Sulfate | 8.5 |
| Disodium Cocoamphodiacetate | 3.5 |
| Sodium Chloride | 3.5 |
| Glucolipid | 3.0 |
| Hydrolyzed Collagen | 1.0 |
| Panthenol | 0.4 |
| Cocodimonium Hydroxypropyl Hydrolyzed Keratin | 0.3 |
| Hydrolyzed Keratin | 0.3 |
| Citric Acid | ad pH 5.5 |
| Sodium Benzoate | 0.7 |
| Polyquaternium-10 | 0.2 |
| Hexyl Cinnamal | 0.1 |
| Limonene | 0.1 |
| Linalool | 0.1 |
| Benzyl Salicylate | 0.1 |
| Benzyl Alcohol | 0.2 |
| Propylene Glycol | 0.2 |
| Dyes | q.s. |

Example Formulation 23: Shampoo

| Ingredient | % |
|---|---|
| Aqua | ad 100 |
| Sodium Laureth Sulfate | 8.0 |
| Cocamidopropyl Betaine | 3.0 |
| Glucolipid | 3.0 |
| PEG-7 Glyceryl Cocoate | 2.5 |
| Dimethicone | 2.5 |
| *Prunus Armeniaca* (Apricot) Kernel Oil | 2.5 |
| Panthenol | 0.3 |

-continued

| Ingredient | % |
|---|---|
| Cocodimonium Hydroxypropyl Hydrolyzed Keratin | 0.7 |
| Hydrolyzed Keratin | 0.7 |
| Sodium Chloride | 0.8 |
| Cocamide MEA | 0.5 |
| Glycol Distearate | 0.2 |
| Sodium Benzoate | 0.7 |
| Citric Acid | ad pH 5.5 |
| Polyquaternium-10 | 0.5 |
| Laureth-4 | 0.4 |
| PEG-40 Hydrogenated Castor Oil | 0.2 |
| Hydrogenated Castor Oil | 0.7 |
| Laureth-7 | 0.5 |
| Hexyl Cinnamal | 0.1 |
| Propylene Glycol | 0.8 |
| Hexyl Salicylate | 0.3 |
| Glycerin | 0.5 |
| Linalool | 0.2 |
| Limonene | 0.1 |
| Dyes | q.s. |

Example Formulation 24: Shampoo

| Ingredient | % |
|---|---|
| Aqua | ad 100 |
| Sodium Coco Sulfate | 6.0 |
| Lauryl Glucoside | 4.0 |
| Glycerin | 3.5 |
| Sodium Lactate | 2.5 |
| Glucolipid | 2.0 |
| Betaine | 0.8 |
| Sodium Chloride | 0.9 |
| *Simmondsia Chinensis* Seed Oil | 0.8 |
| Sodium Cocoyl Glutamate | 0.7 |
| Disodium Cocoyl Glutamate | 0.5 |
| Xanthan Gum | 0.5 |
| Hydrated Silica | 0.5 |
| Parfum, Dyes | q.s. |

Example Formulation 25: Shampoo for Children

| Ingredient | % |
|---|---|
| Aqua | ad 100 |
| Sodium Coco Sulfate | 7.0 |
| Decyl Glucoside | 5.0 |
| Lactis Proteinum | 3.5 |
| Sorbitan Caprylate | 3.0 |
| Glucolipid | 3.0 |
| Glycerin | 2.5 |
| Sodium Lactate | 2.5 |
| Alcohol | 2.0 |
| Hydrolyzed Wheat Protein | 0.7 |
| Hydrolyzed Wheat Starch | 0.7 |
| Sodium Chloride | 0.9 |
| Limonene | 0.1 |
| Citral | 0.1 |
| Phenethyl Alcohol | 0.1 |
| Dyes | q.s. |

Example Formulation 26: Intensive Cream Shampoo

| Ingredient | % |
|---|---|
| Aqua | ad 100 |
| Sodium Laureth Sulfate | 8.5 |
| Cocamidopropyl Betaine | 3.0 |
| Glucolipid | 2.5 |
| Sodium Chloride | 2.5 |
| Panthenol | 0.5 |

-continued

| Ingredient | % |
|---|---|
| Hydrolyzed Keratin | 0.8 |
| Argania Spinosa Kernel Oil | 0.5 |
| Cocamide MEA | 0.5 |
| Glycol Distearate | 0.5 |
| PEG-7 Glyceryl Cocoate | 0.4 |
| Sodium Benzoate | 0.7 |
| Citric Acid | ad pH 5.0 |
| Laureth-4 | 0.3 |
| PEG-40 Hydrogenated Castor Oil | 0.4 |
| Hydrogenated Castor Oil | 0.4 |
| Styrene/Acrylates Copolymer | 0.5 |
| Dimethicone | 0.8 |
| Polyquaternium-7 | 0.9 |
| PEG-12 Dimethicone | 0.5 |
| Guar Hydroxypropyltrimonium Chloride | 0.3 |
| Benzyl Salicylate | 0.1 |
| Propylene Glycol | 0.8 |
| Glycerin | 0.5 |
| Limonene | 0.1 |
| Linalool | 0.1 |
| PEG-14m | 0.1 |
| Dyes | q.s. |

Example Formulation 27: Shampoo

| Ingredient | % |
|---|---|
| Aqua | ad 100 |
| Sodium Laureth Sulfate | 7.5 |
| Cocamidopropyl Betaine | 3.0 |
| Glucolipid | 2.5 |
| Sodium Chloride | 2.0 |
| Sodium Xylenesulfonate | 1.7 |
| Cocamide MEA | 1.5 |
| Sodium Citrate | 1.5 |
| Citric Acid | ad pH 5.0 |
| Dimethiconol | 1.0 |
| Cassia Hydroxypropyltrimonium Chloride | 0.3 |
| Sodium Benzoate | 0.9 |
| Disodium EDTA | 0.7 |
| Panthenol | 0.7 |
| Panthenyl Ethyl Ether | 0.3 |
| *Persea Gratissima* (Avocado) Oil | 0.2 |
| Methylchloroisothiazolinone | 0.1 |
| Methylisothiazolinone | 0.1 |
| Parfum, Dyes | q.s. |

Example Formulation 28: Caffeine Shampoo

| Ingredient | % |
|---|---|
| Aqua | ad 100 |
| Sodium Laureth Sulfate | 6.0 |
| Laureth-2 | 4.0 |
| Disodium Laureth Sulfosuccinate | 2.5 |
| Sodium Lauroyl Glutamate | 2.5 |
| Glucolipid | 2.0 |
| Sodium Chloride | 2.0 |
| Caffeine | 1.5 |
| Panthenol | 0.2 |
| PEG-120 Methyl Glucose Dioleate | 0.5 |
| Hydrolysed Wheat Protein | 0.7 |
| Citric Acid | ad pH 5.5 |
| Sodium Citrate | 0.5 |
| Menthol | 0.7 |
| PEG-40 Hydrogenated Castor Oil | 0.4 |
| Potassium Sorbate | 0.3 |
| Polyquaternium-7 | 0.4 |
| Disodium EDTA | 0.5 |
| Sodium Benzoate | 0.7 |
| Zinc PCA | 0.3 |
| Niacinamide | 0.1 |
| Limonene | 0.1 |

-continued

| Ingredient | % |
|---|---|
| Tocopherol | 0.1 |
| Phenoxyethanol | 0.5 |
| Methylparaben | 0.3 |
| Propylparaben | 0.3 |
| Dyes | q.s. |

Example Formulation 29: Power Grey Shampoo

| Ingredient | % |
|---|---|
| Aqua | ad 100 |
| Sodium Laureth Sulfate | 6.5 |
| Sodium Cocoamphoacetate | 4.5 |
| PEG-3 Distearate | 3.0 |
| Cocamidopropyl Betaine | 3.0 |
| Glucolipid | 2.5 |
| Sodium Chloride | 2.5 |
| Caffeine | 1.5 |
| Panthenol | 0.2 |
| Phenoxyethanol | 0.7 |
| Coco Glucoside | 0.9 |
| Glyceryl Oleate | 0.4 |
| Phosphoric Acid | 0.2 |
| PEG-120 Methyl Glucose Dioleate | 0.9 |
| Menthol | 0.9 |
| Polyquaternium-7 | 0.7 |
| Sodium Hydroxide | 0.3 |
| Citric Acid | ad pH 5.5 |
| Niacinamide | 0.1 |
| Zinc PCA | 0.5 |
| Limonene | 0.1 |
| Sodium Benzoate | 0.2 |
| Methylparaben | 0.3 |
| Propylparaben | 0.3 |
| Dyes | q.s. |

Example Formulation 30: Shampoo

| Ingredient | % |
|---|---|
| Aqua | ad 100 |
| Lauryl Glucoside | 6.5 |
| Cocamidopropyl Betaine | 3.0 |
| Coco Glucoside | 2.5 |
| Glucolipid | 2.0 |
| Glyceryl Oleate | 1.5 |
| Sodium Cocoyl Glutamate | 1.0 |
| Panthenol | 0.5 |
| Polyquaternium-10 | 0.3 |
| Chamomilla Recutita Extract | 0.5 |
| Glyceryl Caprylate | 0.3 |
| p-Anisic Acid | 0.05 |
| Citric Acid | ad pH 5.0 |
| Parfum, Dyes | q.s. |

Example Formulation 31: Caffeine Shampoo

| Ingredient | % |
|---|---|
| Aqua | ad 100 |
| Sodium Coco Sulfate | 6.0 |
| Glycerin | 5.5 |
| Lauryl Glucoside | 4.5 |
| Cocamidopropyl Betaine | 3.0 |
| Glucolipid | 2.5 |
| Lauroyl Sarcosine | 2.0 |
| Caffeine | 1.0 |
| Xanthan Gum | 1.0 |
| Hydroxypropyl Guar Hydroxypropyltrimonium Chloride | 0.3 |
| Alcohol | 0.8 |

-continued

| Ingredient | % |
|---|---|
| Coffea Arabica Bean Extract | 0.3 |
| Panthenyl Ethyl Ether | 0.4 |
| Panthenol | 0.2 |
| Limonene | 0.1 |
| Linalool | 0.1 |
| Dyes | q.s. |

Example Formulation 32: Shampoo

| Ingredient | % |
|---|---|
| Aqua | ad 100 |
| Sodium Laureth Sulfate | 6.5 |
| Cocamidopropyl Betaine | 3.0 |
| Sodium Chloride | 3.0 |
| Glucolipid | 2.0 |
| Panthenol | 0.2 |
| Benzophenone-4 | 0.9 |
| Glycol Distearate | 0.7 |
| Laureth-4 | 0.8 |
| Glycerin | 0.9 |
| Formic Acid | 0.2 |
| Decyl Glucoside | 0.9 |
| Polyquaternium-10 | 0.4 |
| Niacinamide | 0.1 |
| Sodium Benzoate | 0.1 |
| Potassium Sorbate | 0.2 |
| Citric Acid | ad pH 5.0 |
| Parfum, Dyes | q.s. |

Example Formulation 33: Shampoo

| Ingredient | % |
|---|---|
| Aqua | ad 100 |
| Sodium Laureth Sulfate | 8.5 |
| Cocamidopropyl Betaine | 3.0 |
| Sodium Chloride | 2.0 |
| Disodium Cocoamphodiacetate | 2.0 |
| Glucolipid | 2.0 |
| Sodium Benzoate | 0.7 |
| Panthenol | 0.2 |
| Sodium Laureth-8 Sulfate | 0.7 |
| Citric Acid | ad pH 5.0 |
| Sodium Cocoyl Glutamate | 0.8 |
| Glycol Distearate | 0.9 |
| Styrene/Acrylates Copolymer | 0.5 |
| Sodium Oleth Sulfate | 0.7 |
| Coco Glucoside | 0.9 |
| Cocamide MEA | 0.7 |
| Isopropyl Alcohol | 0.2 |
| Parfum, Dyes | q.s. |

Example Formulation 34: Volume Shampoo

| Ingredient | % |
|---|---|
| Aqua | ad 100 |
| Sodium Laureth Sulfate | 7.0 |
| Cocamidopropyl Betaine | 3.0 |
| Coco Glucoside | 3.0 |
| Glucolipid | 2.0 |
| Nymphaea Coerulea Flower Extract | 2.0 |
| Hydrolyzed Rice Protein | 2.0 |
| Cocamide MEA | 2.0 |
| Polyquaternium-10 | 0.5 |
| Malic Acid | ad pH 5.5 |
| Disodium EDTA | 0.5 |
| Propylene Glycol | 0.5 |
| Benzophenone-4 | 0.3 |

-continued

| Ingredient | % |
|---|---|
| Ethylhexyl Methoxycinnamate | 0.3 |
| Sodium Chloride | 0.9 |
| Benzyl Alcohol | 0.9 |
| PPG-9 | 0.2 |
| Methylisothiazolinone | 0.1 |
| Methylparaben | 0.1 |
| Propylparaben | 0.1 |
| Parfum, Dyes | q.s. |

Example Formulation 35: Shampoo

| Ingredient | % |
|---|---|
| Aqua | ad 100 |
| Sodium Laureth Sulfate | 6.5 |
| Coco Glucoside | 5.0 |
| Cocamidopropyl Betaine | 3.0 |
| Glucolipid | 3.0 |
| Glycol Distearate | 2.8 |
| Dimethicone | 1.7 |
| Laureth-23 | 1.5 |
| Laureth-4 | 1.5 |
| Polyquaternium-7 | 0.5 |
| Cocamide MEA | 0.7 |
| Cetyl Alcohol | 0.4 |
| Simmondsia Chinensis Seed Oil | 0.8 |
| Panthenol | 0.3 |
| Malic Acid | ad pH 5.5 |
| Glycine | 0.7 |
| Benzyl Alcohol | 0.7 |
| Disodium EDTA | 0.5 |
| Sodium Hydroxide | 0.2 |
| Guar Hydroxypropyltrimonium Chloride | 0.5 |
| Ethylhexyl Methoxycinnamate | 0.7 |
| Methylparaben | 0.3 |
| Propylparaben | 0.3 |
| PPG-9 | 0.2 |
| Benzophenone-4 | 0.3 |
| Sodium Chloride | 0.8 |
| DMDM Hydantoin | 0.1 |
| Hexyl Cinnamal | 0.1 |
| Limonene | 0.1 |
| Dyes | q.s. |

Example Formulation 36: Shampoo

| Ingredient | % |
|---|---|
| Aqua | ad 100 |
| Sodium Laureth Sulfate | 5.0 |
| Sodium Lauryl Sulfate | 5.0 |
| Cocamidopropyl Betaine | 3.0 |
| Glucolipid | 2.5 |
| Olea Europaea Fruit Oil | 2.0 |
| Cocamide MEA | 2.0 |
| Sodium Chloride | 1.9 |
| Glycol Distearate | 1.7 |
| Glycolipids | 1.0 |
| Sophorolipid | 1.0 |
| Benzyl Alcohol | 1.0 |
| Polyquaternium-10 | 0.5 |
| Hydroxypropyl Methylcellulose | 0.5 |
| Silicone Quaternium-18 | 0.9 |
| Malic Acid | ad pH 5.5 |
| Disodium EDTA | 0.5 |
| Sodium Xylenesulfonate | 0.7 |
| Trideceth-6 | 0.7 |
| Trideceth-12 | 0.5 |
| DMDM Hydantoin | 0.2 |
| Methylparaben | 0.3 |
| Propylparaben | 0.3 |
| Linalool | 0.1 |
| Hexyl Cinnamal | 0.1 |

-continued

| Ingredient | % |
|---|---|
| Butylphenyl Methylpropional | 0.1 |
| Limonene | 0.1 |
| Dyes | q.s. |

Example Formulation 37: Shampoo

| Ingredient | % |
|---|---|
| Aqua | ad 100 |
| Sodium Laureth Sulfate | 3.0 |
| Sodium Lauryl Sulfate | 3.5 |
| Glycol Distearate | 3.3 |
| Dimethicone | 3.0 |
| Cocamidopropyl Betaine | 2.5 |
| Glucolipid | 2.0 |
| Benzyl Alcohol | 0.7 |
| Betaine | 0.4 |
| Cetyl Alcohol | 0.7 |
| Cocamide MEA | 0.7 |
| Glyceryl Oleate | 0.5 |
| Propylene Glycol | 0.6 |
| Menthol | 0.7 |
| Guar Hydroxypropyltrimonium Chloride | 0.4 |
| Butylene Glycol | 0.5 |
| Menthyl Lactate | 0.2 |
| Disodium EDTA | 0.5 |
| Tocopheryl Acetate | 0.1 |
| Laureth-4 | 0.7 |
| Niacinamide | 0.1 |
| Maltodextrin | 0.2 |
| Sodium Ascorbyl Phosphate | 0.1 |
| PPG-9 | 0.2 |
| Salicylic Acid | 0.7 |
| Pyridoxine HCl | 0.1 |
| Malic Acid | ad pH 5.0 |
| Laureth-23 | 0.5 |
| Silica | 0.7 |
| Sodium Chloride | 0.7 |
| Sodium Hydroxide | 0.3 |
| Methylchloroisothiazolinone | 0.1 |
| Methylisothiazolinone | 0.1 |
| Parfum, Dyes | q.s. |

Example Formulation 38: Shampoo

| Ingredient | % |
|---|---|
| Aqua | ad 100 |
| Cocamidopropyl Betaine | 7.0 |
| Sodium Methyl Cocoyl Taurate | 4.0 |
| Glycolipids | 2.0 |
| Glucolipid | 1.0 |
| Sodium Chloride | 2.0 |
| Sodium C14-16 Olefin Sulfonate | 1.0 |
| PEG-120 Methyl Glucose Dioleate | 1.0 |
| Glycol Distearate | 1.0 |
| Sodium Benzoate | 1.0 |
| Caprylyl/Capryl Glucoside | 0.7 |
| PEG-7 Glyceryl Cocoate | 0.7 |
| Citric Acid | ad pH 5.3 |
| Parfum | 0.2 |
| Polyquaternium-10 | 0.2 |
| Coconut Acid | 0.1 |
| Laureth-4 | 0.1 |
| Hydrogenated Castor Oil | 0.1 |
| Glycerin | 0.1 |
| Lactic Acid | 0.1 |
| Propylene Glycol | 0.1 |
| Hydrolyzed Keratin | 0.1 |
| Ceramide NP | 0.05 |
| Panthenol | 0.05 |

Example Formulation 39: Conditioning Shampoo

| Ingredient | % |
|---|---|
| Aqua | ad 100 |
| Sodium Cocoamphoacetate | 5.0 |
| Cocamidopropyl Betaine | 4.0 |
| Glycolipids | 1.5 |
| Glucolipid | 1.5 |
| Isostearamide MIPA; Glyceryl Laurate | 1.2 |
| Bis-(Isostearoyl/Oleoyl Isopropyl) Dimonium Methosulfate | 0.5 |
| Citric Acid | 3.0 |
| Perfume, Preservative, Dyes | q.s. |

Example Formulation 40: Conditioning Shampoo

| Ingredient | % |
|---|---|
| Aqua | ad 100 |
| Sodium Laureth Sulfate | 7.0 |
| Cocamidopropyl Betaine | 1.5 |
| Glucolipid | 1.5 |
| Palmitamidopropyltrimonium Chloride | 1.0 |
| Polysilicone-19 | 1.0 |
| PEG-18 Glyceryl Oleate/Cocoate | 2.5 |
| Citric Acid | ad pH 5.5 |
| Perfume, Preservative | q.s. |

Example Formulation 41: Conditioning Shampoo

| Ingredient | % |
|---|---|
| Aqua | ad 100 |
| Sodium Cocoamphoacetate | 5.0 |
| Cocamidopropyl Betaine | 3.0 |
| Disodium Lauryl Sulfosuccinate | 3.0 |
| Glycolipids | 1.5 |
| Glucolipid | 1.5 |
| Palmitamidopropyltrimonium Chloride | 2.0 |
| Isostearamide MIPA, Glyceryl Laurate | 1.0 |
| PEG-200 Hydrogenated Glyceryl Palmate; PEG-7 Glyceryl Cocoate | 1.0 |
| Methoxy PEG/PPG-7/3 Aminopropyl Dimethicone | 0.5 |
| Polyquaternium-10 | 0.2 |
| Citric Acid | ad pH 5.5 |
| Perfume, Preservative | q.s. |

Example Formulation 42: Conditioning Shampoo

| Ingredient | % |
|---|---|
| Aqua | ad 100 |
| Sodium Laureth Sulfate | 6.0 |
| Cocamidopropyl Betaine | 3.0 |
| Glucolipid | 3.0 |
| Glycol Distearate, Laureth-4, Cocamidopropyl Betaine | 2.0 |
| PEG-120 Methyl Glucose Dioleate | 1.7 |
| Glucolipid | 1.5 |
| Sorbitan Sesquicaprylate | 1.0 |
| Sodium Chloride | 1.0 |
| Silicone-Quatemium-22 | 0.8 |
| Glycolipids | 0.5 |
| Hydroxypropyl Guar Hydroxypropyltrimonium Chloride | 0.5 |
| Creatine | 0.5 |
| Citric Acid | ad pH 5.5 |
| Perfume, Preservative | q.s. |

Example Formulation 43: Natural Shampoo

| Ingredient | % |
|---|---|
| Aqua | ad 100 |
| Sodium Coco-Sulfate | 9.0 |
| Glycerin | 5.0 |
| Lauryl Glucoside | 2.5 |
| Glucolipid | 2.5 |
| Sodium Lactate | 1.0 |
| Betaine | 1.0 |
| Hamamelis Virginiana Leaf Extract | 1.0 |
| Alcohol Denat. | 1.0 |
| Sodium/Disodium Cocoyl Glutamate | 0.8 |
| Maris Sal | 0.5 |
| Dipotassium Glycyrrhizate | 0.5 |
| Glycerophosphocholine | 0.1 |
| Parfum, Preservative | q.s. |

Example Formulation 44: Natural Shampoo

| Ingredient | % |
|---|---|
| Aqua | ad 100 |
| Sodium Coco-sulfate | 6.0 |
| Glycerin | 5.0 |
| Coco-glucoside | 4.0 |
| Lauryl Glucoside | 3.0 |
| Glucolipid | 2.0 |
| Glyceryl Oleate | 1.5 |
| Sodium Chloride | 1.0 |
| Calendula Officinalis Flower Extract | 0.5 |
| Parfum | 0.5 |
| Polyglyceryl-4 Caprate | 0.3 |
| Xanthan Gum | 0.3 |
| Locust bean Gum | |
| Lysolecithin | 0.2 |
| Coco-Caprylate | 0.1 |
| Magnolia Officinalis Bark Extract | 0.1 |
| Tocopherol | 0.1 |
| Squalene | 0.1 |

Example Formulation 45: Natural Shampoo

| Ingredient | % |
|---|---|
| Aqua | ad 100 |
| Sodium Lauroyl Methyl Isethionate | 5.0 |
| Disodium Cocoamphodipropionate | 4.0 |
| Acrylates Copolymer | 2.0 |
| Hydroxyethylcellulose | 2.0 |
| Glucolipid | 2.0 |
| Cocos Nucifera Oil | 0.8 |
| Panthenol | 0.4 |
| Tocopherol | 0.4 |
| Tocopheryl Acetate | 0.2 |
| Cetyl Triethylmonium Dimethicone PEG-8 Succinate | 0.2 |
| Glycol Distearate | 0.2 |
| Laureth-4 | 0.2 |
| Cocamidopropyl Betaine | 0.2 |
| Ethylhexyl Salicylate | 0.1 |
| Disodium EDTA | 0.1 |
| Ethylhexylglycerin | 0.1 |
| Glycerin | 0.1 |
| Hexylene Glycol | 0.1 |
| Sodium Coco PG-dimonium Chloride Phosphate | 0.1 |
| BHT | 0.1 |
| Citric Acid | 0.1 |
| Phenoxyethanol | 0.1 |
| Formic Acid | 0.1 |
| Parfum | q.s. |

Example Formulation 46: Natural Shampoo

| Ingredient | % |
|---|---|
| Aqua | ad 100 |
| Moroccan Lava Clay | 5.0 |
| Behenyl Alcohol | 3.0 |
| Glycerin | 2.5 |
| Glyceryl Stearate Citrate | 2.0 |
| Lauryl Glucoside | 2.0 |
| Coco-glucoside | 2.0 |
| Helianthus Annuus Hybrid Oil | 1.5 |
| *Prunus Armeniaca* Kernel Oil | 1.5 |
| Glucolipid | 1.0 |
| Glycolipids | 1.0 |
| Argania Spinosa Kernel Oil | 1.0 |
| Magnolia Officinalis Bark Extract | 1.0 |
| Triethyl Citrate, Glyceryl Caprylate Benzoic Acid | 1.0 |
| Xanthan Gum | 0.8 |
| Sodium Lactate | 0.5 |
| Benzyl Alcohol | 0.3 |
| Lactic Acid | 0.2 |
| Parfum | q.s. |

Example Formulation 47: Natural Shampoo

| Ingredient | % |
|---|---|
| Aqua | ad 100 |
| Cocamidopropyl Betaine | 7.0 |
| Cetrimonium Chloride | 5.0 |
| Decyl Glucoside | 5.0 |
| Sodium Chloride | 2.0 |
| Glucolipid | 1.0 |
| Sorbitan Caprylate | 0.8 |
| Cocos Nucifera Oil | 0.8 |
| Inulin | 0.5 |
| Benzyl Alcohol | 0.2 |
| Cetearyl Alcohol | 0.2 |
| Xanthan Gum | 0.2 |
| Sodium Cocoyl Glutamate | 0.1 |
| Parfum | 0.1 |
| Glycerin | 0.2 |
| Argania Spinosa Kernel Oil | 0.1 |
| Titanium Dioxide | 0.1 |
| Hydroxypropyl Guar Hydroxypropyltrimonium Chloride | 0.1 |
| Lactic Acid | 0.1 |
| Hexyl Cinnamal | 0.1 |
| Sodium Hydroxide | 0.1 |
| Ascorbyl Palmitate | 0.1 |
| Tocopherol | 0.1 |

Example Formulation 48: Natural Shampoo

| Ingredient | % |
|---|---|
| Aqua | ad 100 |
| Glycerin | 5.0 |
| Sodium Coco-sulfate | 5.0 |
| Lauryl Glucoside | 4.0 |
| Glucolipid | 4.0 |
| Betaine | 3.0 |
| Maris Sal | 2.0 |
| Camellia Oleifera Leaf Extract | 1.5 |
| Pisum Sativum Peptide | 1.5 |
| Oryza Sativa Extract | 1.0 |
| Pisum Sativum Seed Extract | 0.5 |
| Disodium Cocoyl Glutamate | 0.4 |
| Sodium Cocoyl Glutamate | 0.4 |
| PCA Glyceryl Oleate | 0.2 |
| Alcohols | 0.1 |
| Parfum | q.s. |

Example Formulation 49: Anti-Hair Loss Tonic

| Ingredient | % |
|---|---|
| Aqua | ad 100 |
| Alcohol Denat. | 50.0 |
| PEG-40 Hydrogenated Castor Oil | 2.5 |
| Glucolipid | 1.5 |
| PEG-7 Glyceryl Cocoate | 2.0 |
| Sphinganine | 0.1 |
| Parfum, Preservative | q.s. |

Example Formulation 50: Shower Oil

| Ingredient | % |
|---|---|
| Aqua | ad 100 |
| Magnesium Laureth Sulfate | 6.0 |
| PEG-7 Glyceryl Cocoate | 5.0 |
| Hydrogenated Starch Hydrolysate | 3.0 |
| Cocamidopropyl Betaine | 3.0 |
| Glucolipid | 3.0 |
| Decyl Glucoside | 1.0 |
| *Prunus Amygdalus Dulcis* (Sweet Almond) Oil | 1.0 |
| Olive Oil | 0.5 |
| PEG-7 Esters | 0.2 |
| Parfum | 0.1 |
| Polysorbate 20 | 0.1 |
| Sodium Benzoate | 0.2 |
| Citric Acid | 0.1 |
| PEG-6 Caprylic/Capric Glycerides | 0.1 |
| PEG-120 Methyl Glucose Dioleate | 0.1 |
| Disodium EDTA | 0.1 |

Example Formulation 51: Shower Mousse

| Ingredient | % |
|---|---|
| Aqua | ad 100 |
| Sodium Lauroyl Glutamate | 15.0 |
| Isobutane | 6.0 |
| Cocamidopropyl Betaine | 4.0 |
| Glycerin | 3.0 |
| Glucolipid | 3.0 |
| Sodium Chloride | 2.6 |
| Sodium Lauroyl Glycinate | 1.5 |
| Propane | 1.0 |
| Butane | 0.6 |
| Citric Acid | 0.4 |
| Iodopropynyl Butylcarbamate | 0.3 |
| Lauric Acid | 0.3 |
| Parfum | 0.1 |
| Polysorbate 20 | 0.1 |
| Sodium Benzoate | 0.1 |
| Sodium Hydroxide | 0.1 |
| Stearic Acid | 0.1 |
| Tetrasodium EDTA | 0.1 |

Example Formulation 52: Shower Jelly

| Ingredient | % |
|---|---|
| Glycerin | 3.5 |
| Sodium Laureth Sulfate | 3.5 |
| Glucolipid | 3.0 |
| Propylene Glycol | 2.0 |
| Chondrus Crispus Extract | 2.0 |
| Pyrus Malus Juice | 1.0 |
| Vitis Vinifera Juice | 0.5 |
| Parfum | 0.2 |
| Butylphenyl Methylpropional | 0.1 |

Example Formulation 53: Shower Jelly

| Ingredient | % |
| --- | --- |
| Aqua | ad 100 |
| Glycerin | 9.0 |
| Coco-Glucoside | 5.0 |
| Decyl Glucoside | 5.0 |
| Glucolipid | 2.0 |
| Chondrus crispus extract | 1.0 |
| Parfum | 0.2 |
| Citric Acid | 0.2 |
| Sodium Anisate | 0.1 |
| Sodium Levulinate | 0.1 |

Example Formulation 54: Shower Scrub

| Ingredient | % |
| --- | --- |
| Aqua | ad 100 |
| Maris Sal | 15.0 |
| Sodium Laureth Sulfate | 9.0 |
| Glucolipid | 2.0 |
| Sodium Cocoamphoacetate | 1.0 |
| Betaine | 1.0 |
| *Citrus Limon* (Lemon) Peel Powder | 0.5 |
| Lactic Acid | ad pH 5.5 |
| Parfum, Dyes | qs. |

Example Formulation 55: Cellulose Scrub

| Ingredient | % |
| --- | --- |
| Aqua | ad 100 |
| Glucolipid | 7.0 |
| Coco Glucoside | 6.0 |
| Glycerin | 5.0 |
| Glyceryl Stearate | 5.0 |
| Citrus Aurantium Dulcis Fruit Water | 4.5 |
| Helianthus Annuus Hybrid Oil | 4.0 |
| Cellulose | 2.0 |
| Jojoba Esters | 2.0 |
| Cetyl Alcohol | 2.0 |
| *Simmondsia Chinensis* (Jojoba) Seed Oil | 2.0 |
| *Olea Europaea* (Olive) Fruit Oil | 2.0 |
| Hydrogenated Castor Oil | 0.8 |
| *Prunus Armeniaca* (Apricot) Kernel Oil | 0.5 |
| Leontopodium Alpinum Extract | 0.1 |
| Xanthan Gum | 0.3 |
| Benzyl Alcohol | 0.2 |
| Parfum | 0.1 |
| Dehydroacetic Acid | 0.1 |
| Citric acid | ad pH 5.0 |
| Lactic acid | 0.1 |
| Sodium Hydroxide | 0.1 |
| Parfum, Dyes | q.s. |

Example Formulation 56: Exfoliating Body Scrub

| Ingredient | % |
| --- | --- |
| Aqua | ad 100 |
| Coco-Glucoside | 7.0 |
| Alcohol | 6.0 |
| Glycerin | 5.0 |
| Glycine Soja Oil | 5.0 |
| Hydrated Silica | 4.0 |
| Xanthan Gum | 3.0 |
| Glucolipid | 3.0 |
| Disodium/Sodium Cocoyl Glutamate | 1.0 |
| *Coffea Arabica* (Coffee) Seed Powder | 1.0 |
| *Cocos Nucifera* (Coconut) Shell Powder | 1.0 |
| Citric Acid | ad pH 5.2 |
| Glyceryl Oleate | 0.5 |
| Parfum | 0.1 |
| Preservative, Dyes | q.s. |

Example Formulation 57: Dry Shampoo

| Ingredient | % |
| --- | --- |
| Butane, Propane | 53.0 |
| Alcohol Denat. | 36.0 |
| Aluminum Starch Octenyl succinate | 3.0 |
| Panthenol | 1.5 |
| Tocopherol | 1.0 |
| *Cocos Nucifera* Oil | 1.0 |
| *Curcuma Longa* (Turmeric) Root Extract | 0.6 |
| Silica | 0.5 |
| Sodium Bicarbonate | 0.5 |
| Charcoal Powder | 0.4 |
| Hydrolyzed Rice Protein | 0.4 |
| Aminopropyl Phenyl Trimethicone | 0.4 |
| Benzophenone-4 | 0.3 |
| Polysorbate 20 | 0.3 |
| Glucolipid | 0.3 |
| Cyclopentasiloxane | 0.2 |
| Cyclohexasiloxane | 0.2 |
| Glycerin | 0.2 |
| Aqua | 0.2 |
| Parfum | q.s. |

Example Formulation 58: Dry Shampoo

| | % |
| --- | --- |
| Butane, Isobutane, Propane | 55.0 |
| *Oryza Sativa* (Rice) Starch | 25.0 |
| Alcohol denat. | 18.0 |
| Parfum | 1.0 |
| Glucolipid | 0.5 |
| Distearyldimonium Chloride | 0.3 |
| Cetrimonium Chloride | 0.2 |

Shower

Example Formulation 59: Shower Gel

| Ingredient | % |
| --- | --- |
| Aqua | ad 100 |
| Sodium Laureth Sulfate | 8.5 |
| Cocamidopropyl Betaine | 3.0 |
| Sodium Chloride | 2.7 |
| Glucolipid | 2.5 |
| Guar Gum | 0.5 |
| Polyquaternium-7 | 0.5 |
| Bisabolol | 0.2 |
| Trideceth-9 | 0.5 |
| Sodium Sulfate | 0.9 |
| Tetrasodium EDTA | 0.2 |
| Citric Acid | ad pH 5.5 |
| Sodium Benzoate | 0.7 |
| Benzyl Alcohol | 0.7 |
| Benzyl Salicylate | 0.1 |
| Geraniol | 0.2 |
| Hexyl Cinnamal | 0.1 |
| Limonene | 0.1 |
| Linalool | 0.1 |
| Dyes | q.s. |

Example Formulation 60: Body Wash

| Ingredient | % |
|---|---|
| Water | ad 100 |
| Sodium Laureth Sulfate | 4.0 |
| Sodium Lauryl Sulfate | 4.0 |
| Sodium Chloride | 3.3 |
| Cocamidopropyl Betaine | 3.0 |
| Glucolipid | 3.0 |
| Sodium Benzoate | 1.5 |
| Citric Acid | ad pH 5.5 |
| Disodium EDTA | 0.5 |
| *Zea Mays* (Corn) Silk Extract | 0.5 |
| Methylchloroisothiazolinone | 0.1 |
| Methylisothiazolinone | 0.1 |
| Potassium Sorbate | 0.2 |
| Parfum, Dyes | q.s. |

Example Formulation 61: Cool Down Shower Gel

| Ingredient | % |
|---|---|
| Aqua | ad 100 |
| Sodium Laureth Sulfate | 8.0 |
| Cocamidopropyl Betaine | 3.0 |
| Glucolipid | 3.0 |
| Glycerin | 2.7 |
| Acrylates Copolymer | 2.5 |
| Sodium Chloride | 2.2 |
| Phenoxyethanol | 1.5 |
| Taurine | 1.5 |
| Benzyl Alcohol | 1.0 |
| Sodium Hydroxide | 0.5 |
| PEG-40 Hydrogenated Castor Oil | 0.7 |
| Citric Acid | ad pH 5.0 |
| Mannitol | 0.7 |
| Benzophenone-4 | 0.3 |
| Ethylhexyl Salicylate | 0.5 |
| Cellulose | 0.5 |
| Linalool | 0.1 |
| Butyl Methoxydibenzoylmethane | 0.2 |
| Hydroxypropyl Methylcellulose | 0.2 |
| Dyes | q.s. |

Example Formulation 62: Shower Gel

| Ingredient | % |
|---|---|
| Aqua | ad 100 |
| Cocamidopropyl Betaine | 5.0 |
| Sodium Myreth Sulfate | 4.5 |
| Sodium Laureth Sulfate | 4.0 |
| Glucolipid | 3.5 |
| PEG-7 Glyceryl Cocoate | 3.2 |
| Glycerin | 3.0 |
| Glyceryl Glucoside | 2.5 |
| Bisabolol | 2.0 |
| *Chamomilla Recutita* (Matricaria) Flower Extract | 2.2 |
| Sodium Chloride | 2.2 |
| PEG-40 Hydrogenated Castor Oil | 2.0 |
| Citric Acid | ad pH 5.0 |
| Glycolipids | 1.5 |
| PEG-90 Glyceryl Isostearate | 1.2 |
| PEG-200 Hydrogenated Glyceryl Palmate | 1.2 |
| Sophorolipid | 1.0 |
| Benzophenone-4 | 1.0 |
| Laureth-2 | 0.7 |
| Polyquaternium-7 | 0.5 |
| BHT | 0.2 |
| Sodium Benzoate | 0.2 |
| Methylparaben | 0.2 |
| Benzyl Alcohol | 0.2 |
| Citronellol | 0.1 |
| Limonene | 0.1 |
| Dyes | q.s. |

Example Formulation 63: Shower Gel

| Ingredient | % |
|---|---|
| Aqua | ad 100 |
| Sodium Laureth Sulfate | 8.0 |
| Cocamidopropyl Betaine | 3.0 |
| Acrylates Copolymer | 3.0 |
| PEG-7 Glyceryl Cocoate | 2.7 |
| Glucolipid | 2.5 |
| Helianthus Annuus Seed Oil | 1.5 |
| Glycerin | 1.5 |
| Glycolipids | 1.5 |
| Sodium Chloride | 1.0 |
| PEG-40 Hydrogenated Castor Oil | 1.0 |
| Disodium Cocoyl Glutamate | 1.0 |
| Trisodium EDTA | 1.0 |
| Propylene Glycol | 1.0 |
| Microcrystalline Cellulose | 0.9 |
| Benzophenone-4 | 0.5 |
| Sodium Sulfate | 0.7 |
| Phenoxyethanol | 0.7 |
| Acacia Gum | |
| Propylparaben | 0.1 |
| Methylparaben | 0.1 |
| Benzyl Alcohol | 0.2 |
| Parfum, Dyes | q.s. |

Example Formulation 64: Body Wash

| Ingredient | % |
|---|---|
| Aqua | ad 100 |
| Sodium Hydroxypropyl Starch Phosphate | 6.0 |
| Sodium Laureth Sulfate | 5.5 |
| Cocamidopropyl Betaine | 3.0 |
| Glucolipid | 3.0 |
| Lauric Acid | 2.5 |
| Petrolatum | 2.0 |
| Sodium Cocoyl Glycinate | 2.0 |
| Glycerin | 1.7 |
| Sodium Lauroyl Isethionate | 1.5 |
| *Glycine Soja* (Soybean) Oil | 1.0 |
| *Helianthus Annuus* (Sunflower) Oil | 1.0 |
| Sodium Chloride | 1.0 |
| Stearic Acid | 0.7 |
| Guar Hydroxypropyltrimonium Chloride | 0.3 |
| DMDM Hydantoin | 0.1 |
| Tallow Acid | 0.2 |
| Palmitic Acid | 0.1 |
| Sodium Isethionate | 0.2 |
| BHT | 0.1 |
| Tetrasodium EDTA | 0.2 |
| Methylisothiazolinone | 0.3 |
| Iodopropynyl Butylcarbamate | 0.1 |
| Titanium Dioxide | 0.1 |
| Parfum, Dyes | q.s. |

Example Formulation 65: Anti-Aging Body Wash

| Ingredient | % |
|---|---|
| Aqua | ad 100 |
| Petrolatum | 5.0 |
| Mineral (Paraffinum Liquidum) Oil | 4.0 |
| Sodium Trideceth Sulfate | 3.5 |

-continued

| Ingredient | % |
|---|---|
| Sodium Lauryl Sulfate | 3.0 |
| Sodium Lauroamphoacetate | 3.0 |
| Sodium Chloride | 2.3 |
| Glucolipid | 2.0 |
| Trideceth-3 | 1.0 |
| *Simmondsia Chinensis* (Jojoba) Butter | 0.7 |
| Niacinamide | 0.1 |
| Panthenol | 0.3 |
| Soluble Collagen | 0.5 |
| Citric Acid | ad pH 5.5 |
| Disodium EDTA | 0.3 |
| Guar Hydroxypropyltrimonium Chloride | 0.3 |
| Methylchloroisothiazolinone | 0.1 |
| Methylisothiazolinone | 0.1 |
| PEG-90m | 0.7 |
| Sodium Benzoate | 0.3 |
| Sodium Hydroxide | 0.1 |
| Xanthan Gum | 0.5 |
| Calcium Alginate | .1 |
| Parfum, Dyes | q.s. |

Example Formulation 66: Shower Gel

| Ingredient | % |
|---|---|
| Aqua | ad 100 |
| Sodium Laureth Sulfate | 9.0 |
| Cocamidopropyl Betaine | 3.0 |
| Glucolipid | 3.0 |
| Glycerin | 3.0 |
| Sodium Chloride | 2.8 |
| PEG-7 Glyceryl Cocoate | 2.5 |
| PEG-40 Hydrogenated Castor Oil | 2.5 |
| Citric Acid | ad pH 5.5 |
| Sodium Benzoate | 1.0 |
| Potassium Sorbate | 0.7 |
| Alcohol | 0.5 |
| Citronellol | 0.2 |
| Benzyl Alcohol | 0.7 |
| Limonene | 0.1 |
| Linalool | 0.2 |
| Geraniol | 0.2 |
| Hexyl Cinnamal | 0.1 |
| Ethylhexyl Salicylate | 0.1 |
| Octocrylene | 0.3 |
| Butyl Methoxydibenzoylmethane | 0.2 |
| Dyes | q.s. |

Example Formulation 67: Shower Gel

| Ingredient | % |
|---|---|
| Aqua | ad 100 |
| Alcohol | 6.0 |
| Coco Glucoside | 6.0 |
| Glycerin | 3.0 |
| Glucolipid | 3.0 |
| Xanthan Gum | 1.5 |
| Disodium Cocoyl Glutamate | 2.0 |
| Citric Acid | ad pH 5.5 |
| *Citrus Aurantifolia* (Lime) Oil | 0.5 |
| Sodium Cocoyl Glutamate | 0.7 |
| Glyceryl Oleate | 0.3 |
| Sodium Lauroyl Lactylate | 0.8 |
| Limonene | 0.1 |
| Linalool | 0.1 |
| Dyes | q.s. |

Example Formulation 68: Shower Gel for Men

| Ingredient | % |
|---|---|
| Aqua | ad 100 |
| Sodium Laureth Sulfate | 9.5 |
| Cocamidopropyl Betaine | 3.0 |
| Cocamide MEA | 3.0 |
| Glucolipid | 3.0 |
| Glycerin | 2.5 |
| PPG-12 | 2.0 |
| Sodium Chloride | 2.0 |
| Citric Acid | ad pH 5.5 |
| Sodium Benzoate | 1.0 |
| Phenoxyethanol | 0.7 |
| Benzyl Alcohol | 0.7 |
| Butylphenyl Methylpropional | 0.1 |
| Citronellol | 0.1 |
| Geraniol | 0.2 |
| Hexyl Cinnamal | 0.1 |
| Limonene | 0.1 |
| Linalool | 0.1 |
| Dyes | q.s. |

Example Formulation 69: Moisturising Shower Cream

| Ingredient | % |
|---|---|
| Aqua | ad 100 |
| Sodium Laureth Sulfate | 8.5 |
| Cocamidopropyl Betaine | 3.0 |
| Glycerin | 2.5 |
| Glucolipid | 2.0 |
| Sodium Chloride | 1.7 |
| Cocamide MEA | 1.5 |
| Styrene/Acrylates Copolymer | 1.5 |
| Sodium Salicylate | 1.0 |
| Sodium Benzoate | 1.0 |
| Polyquaternium-7 | 1.0 |
| Citric Acid | ad pH 5.0 |
| Tetrasodium EDTA | 1.0 |
| Glycol Distearate | 0.9 |
| Laureth-4 | 0.5 |
| Magnolia Officinalis Flower Extract | 0.2 |
| Butyrospermum Parkii Butter Extract | 0.2 |
| *Prunus Amygdalus Dulcis* (Sweet Almond) Extract | 0.1 |
| Tapioca Starch polymethylsilsesquioxane | 0.5 |
| Benzyl Benzoate | 0.1 |
| Cinnamyl Alcohol | 0.1 |
| Hexyl Cinnamal | 0.1 |
| Parfum, Dyes | q.s. |

Example Formulation 70: Shower Cream

| | |
|---|---|
| Aqua | ad 100 |
| Ammonium Lauryl Sulfate | 6.0 |
| Coco Glucoside | 3.5 |
| Cocamidopropyl Betaine | 2.0 |
| Sodium Cocoamphoacetate | 2.0 |
| Glucolipid | 1.5 |
| Argania Spinosa Kernel Oil | 1.0 |
| Butyrospermum Parkii Butter | 1.0 |
| Glycerin | 1.0 |
| Polyquaternium-7 | 1.0 |
| Styrene/Acrylates Copolymer | 1.0 |
| Gelatin Crosspolymer | 0.5 |
| Sodium Chloride | 0.5 |
| Citric Acid | ad pH 5.0 |
| Sodium Benzoate | 0.3 |
| Sodium Salicylate | 0.1 |
| Linalool | 0.1 |
| Dyes | q.s. |

Example Formulation 71: Shower Cream

| Ingredient | % |
|---|---|
| Aqua | ad 100 |
| Sodium Laureth Sulfate | 7.0 |
| Cocamidopropyl Betaine | 3.0 |
| Glucolipid | 2.0 |
| Sodium Chloride | 1.9 |
| Polyquaternium-7 | 1.5 |
| Cocamide MEA | 1.5 |
| PEG-7 Glyceryl Cocoate | 1.0 |
| Laureth-10 | 1.0 |
| Glycol Distearate | 0.8 |
| Citric Acid | ad pH 5.0 |
| Linalool | 0.1 |
| Limonene | 0.1 |
| Benzyl Salicylate | 0.1 |
| Butylphenyl Methylpropional | 0.1 |
| alpha-Isomethyl Ionone | 0.1 |
| Hexyl Cinnamal | 0.1 |
| Citronellol | 0.1 |
| Sodium Benzoate | 0.7 |
| Sodium Salicylate | 0.1 |
| Dyes | q.s. |

Example Formulation 72: Shower Cream

| Ingredient | % |
|---|---|
| Aqua | ad 100 |
| Glycerin | 7.5 |
| Glycine Soja Oil | 3.0 |
| Lauryl Glucoside | 3.0 |
| Sodium Coco Sulfate | 3.0 |
| Glucolipid | 2.5 |
| Alcohol | 1.5 |
| Xanthan Gum | 1.5 |
| Butyrospermum Parkii Butter | 1.2 |
| Sodium Cetearyl Sulfate | 1.0 |
| Sodium Cocoyl Glutamate | 1.0 |
| Disodium Cocoyl Glutamate | 1.0 |
| Tocopherol | 0.1 |
| Helianthus Annuus Seed Oil | 0.3 |
| Limonene | 0.1 |
| Benzyl Salicylate | 0.1 |
| Linalool | 0.1 |
| Dyes | q.s. |

Example Formulation 73: Shower Gel

| Ingredient | % |
|---|---|
| Aqua | ad 100 |
| Sodium Coco Sulfate | 5.0 |
| Glycerin | 5.0 |
| Lauryl Glucoside | 4.0 |
| Sodium Lactate | 2.5 |
| Glucolipid | 2.0 |
| Sodium Cocoyl Glutamate | 2.0 |
| Disodium Cocoyl Glutamate | 2.0 |
| Alcohol | 1.0 |
| Prunus Cerasus Fruit Extract | 1.0 |
| Limonene | 0.1 |
| Coumarin | 0.2 |
| Linalool | 0.1 |
| Citral | 0.1 |
| Dyes | q.s. |

Example Formulation 74: Shower Gel

| Ingredient | % |
|---|---|
| Aqua | ad 100 |
| Alcohol | 5.0 |
| Coco-Glucoside | 5.0 |
| Glycerin | 5.0 |
| Glucolipid | 2.5 |
| Xanthan Gum | 2.5 |
| Disodium Cocoyl Glutamate | 2.0 |
| Citric Acid | ad pH 5.0 |
| *Citrus Aurantifolia* (Lime) Oil | 1.0 |
| Sodium Cocoyl Glutamate | 1.0 |
| Glyceryl Oleate | 1.0 |
| Sodium Lauroyl Lactylate | 0.7 |
| Limonene | 0.1 |
| Citral | 0.1 |
| Linalool | 0.1 |
| Dyes | q.s. |

Example Formulation 75: Oil Shower

| Ingredient | % |
|---|---|
| Aqua | ad 100 |
| Sodium Laureth Sulfate | 8.0 |
| Cocamidopropyl Betaine | 3.0 |
| Glucolipid | 2.0 |
| Acrylates Copolymer | 2.0 |
| Glycolipids | 2.0 |
| Tocopheryl Acetate | 0.5 |
| PEG-7 Glyceryl Cocoate | 0.5 |
| Disodium EDTA | 0.4 |
| Benzophenone-4 | 0.3 |
| PEG-40 Hydrogenated Castor Oil | 0.7 |
| Cellulose | 0.7 |
| Hydroxypropyl Methylcellulose | 0.7 |
| Sodium Chloride | 0.9 |
| Ethylhexylglycerin | 0.2 |
| Phenoxyethanol | 0.7 |
| Methylisothiazolinone | 0.3 |
| Sodium Benzoate | 0.3 |
| Sodium Hydroxide | 0.3 |
| Citric Acid | ad pH 5.5 |
| Parfum, Dyes | q.s. |

Example Formulation 76: Shower Gel

| Ingredient | % |
|---|---|
| Aqua | ad 100 |
| Ammonium Lauryl Sulfate | 6.0 |
| Coco-Betaine | 3.0 |
| Glucolipid | 3.0 |
| Lauroyl/Myristoyl Methyl Glucamide | 1.5 |
| Citric Acid | ad pH 5.0 |
| Benzyl Alcohol, Glycerin, Benzoic Acid, Sorbic Acid | 1.0 |
| Parfum | 0.8 |
| Aloe Vera Leaf Extract | 0.1 |

Example Formulation 77: Shower 1

| Ingredient | % |
|---|---|
| Aqua | ad 100 |
| Glucolipid | 7.0 |
| *Sesamum Indicum* (Sesame) Seed Oil | 4.0 |
| Sophorolipid | 3.0 |
| Sucrose. Alcohol | 2.0 |
| Amino Acids | 1.0 |
| Glycerin | 1.0 |
| Carrageenan | 0.3 |

-continued

| Ingredient | % |
| --- | --- |
| Lavandula Officinalis Flower Oil | 0.3 |
| Xanthan Gum | 0.3 |
| Lactic Acid | 0.1 |

Example Formulation 78: Shower Scrub

| Ingredient | % |
| --- | --- |
| Aqua | ad 100 |
| Maris Sal | 15.0 |
| Sodium Laureth Sulfate | 9.0 |
| Glucolipid | 2.0 |
| Sodium Cocoamphoacetate | 1.0 |
| Betaine | 1.0 |
| *Citrus Limon* (Lemon) Peel Powder | 0.5 |
| Lactic Acid | ad pH 5.5 |
| Parfum, Dyes | qs. |

Example Formulation 79: Cellulose Scrub

| Ingredient | % |
| --- | --- |
| Aqua | ad 100 |
| Glucolipid | 7.0 |
| Coco Glucoside | 6.0 |
| Glycerin | 5.0 |
| Glyceryl Stearate | 5.0 |
| Citrus Aurantium Dulcis Fruit Water | 4.5 |
| Helianthus Annuus Hybrid Oil | 4.0 |
| Cellulose | 2.0 |
| Jojoba Esters | 2.0 |
| Cetyl Alcohol | 2.0 |
| *Simmondsia Chinensis* (Jojoba) Seed Oil | 2.0 |
| *Olea Europaea* (Olive) Fruit Oil | 2.0 |
| Hydrogenated Castor Oil | 0.8 |
| *Prunus Armeniaca* (Apricot) Kernel Oil | 0.5 |
| Leontopodium Alpinum Extract | 0.1 |
| Xanthan Gum | 0.3 |
| Benzyl Alcohol | 0.2 |
| Parfum | 0.1 |
| Dehydroacetic Acid | 0.1 |
| Citric acid | ad pH 5.0 |
| Lactic acid | 0.1 |
| Sodium Hydroxide | 0.1 |
| Parfum, Dyes | q.s. |

Example Formulation 80: Exfoliating Body Scrub

| Ingredient | % |
| --- | --- |
| Aqua | ad 100 |
| Coco-Glucoside | 7.0 |
| Alcohol | 6.0 |
| Glycerin | 5.0 |
| Glycine Soja Oil | 5.0 |
| Hydrated Silica | 4.0 |
| Xanthan Gum | 3.0 |
| Glucolipid | 3.0 |
| Disodium/Sodium Cocoyl Glutamate | 1.0 |
| *Coffea Arabica* (Coffee) Seed Powder | 1.0 |
| *Cocos Nucifera* (Coconut) Shell Powder | 1.0 |
| Citric Acid | ad pH 5.2 |
| Glyceryl Oleate | 0.5 |
| Parfum | 0.1 |
| Preservative, Dyes | q.s. |

Example Formulation 81: Washing Powder

| Ingredient | % |
| --- | --- |
| Talc | 60.0 |
| Sodium Cocoyl Isethionate | 15.0 |
| Sodium C14-16 Olefin Sulfonate | 10.0 |
| Sodium Lauroyl Glutamate | 4.0 |
| Glucolipid | 3.0 |
| Potassium Laurate | 2.0 |
| Sodium Myristoyl Glutamate | 1.5 |
| Chondrus Crispus | 1.5 |
| Isostearyl Alcohol | 1.0 |
| Glycerin | 1.0 |
| BHT | 0.4 |
| Butylene Glycol | 0.3 |
| Protease | 0.2 |
| Salicylic Acid | 0.1 |

Example Formulation 82: Washing Powder

| Ingredient | % |
| --- | --- |
| Hydrates Silica | ad 100 |
| *Zea Mays* Starch | 30.0 |
| Sodium Cocoyl Isethionate | 6.0 |
| Amylopektin | 5.0 |
| Sodium Lauryl Sulfate | 2.5 |
| Sodium Bicarbonate | 2.0 |
| Citric Acid | 1.5 |
| Sodium Lauroyl Glutamate | 1.0 |
| Sodium Palmitate | 1.0 |
| Glucolipid | 1.0 |
| Diglycerin | 0.9 |
| Sodium Lauroyl Aspartate | 0.8 |
| Titanium Dioxide | 0.5 |
| Maltodextrin | 0.5 |
| Allantoin | 0.4 |
| Aqua | 0.3 |
| Butylene Glycol | 0.3 |
| Aloe Vera Leaf Extract | 0.1 |
| *Citrus Limon* (Lemon) Peel Powder | 0.1 |
| Parfum, Preservatives, Dyes | q.s. |

Example Formulation 83: Powder Cleanser

| Ingredient | % |
| --- | --- |
| Hydrated Silica | ad 100 |
| Tapioca Flour | 10.0 |
| Capryl/Capramidopropyl Betaine | 5.0 |
| Sodium Cocoamphoacetate | 5.0 |
| *Helianthus Annuus* (Sunflower) Seed Oil | 4.0 |
| Oleyl Erucate | 2.0 |
| Sucrose Cocoate | 2.0 |
| Glucolipid | 2.0 |
| Coconut Acid | 1.0 |
| Citric Acid | ad pH 6.0 |
| Preservatives, parfum | q.s. |

Example Formulation 84: Powder Cleanser

| Ingredient | % |
| --- | --- |
| Talc | ad 100 |
| Distarch Phosphate | 10.0 |
| Disodium Lauryl Sulfosuccinate | 8.0 |
| Magnesium Aluminum Silicate | 5.0 |
| Oryza Sativa Powder | 5.0 |
| Sodium Lauroyl Glutamate | 2.0 |
| Glucolipid | 2.0 |
| Glucose | 2.0 |
| Magnesium Oxide | 2.0 |

-continued

| Ingredient | % |
|---|---|
| Maltodextrin | 2.0 |
| Titanium Dioxide | 1.0 |
| Pumice | 0.5 |
| Chlorella Vulgaris Powder | 0.1 |

Soap

Example Formulation 85: Gentle Liquid Soap

| Ingredient | % |
|---|---|
| Aqua | ad 100 |
| Sodium Laureth Sulfate | 8.5 |
| Cocamidopropyl Betaine | 3.0 |
| Glucolipid | 2.5 |
| PEG-7 Glyceryl Cocoate | 2.5 |
| Cocamide DEA | 2.5 |
| Glycerin | 2.0 |
| Sorbitan Sesquicaprylate | 1.5 |
| C12-15 Pareth-12 | 1.2 |
| Sodium Benzoate | 1.0 |
| Potassium Sorbate | 1.0 |
| Citric Acid | ad pH 5.5 |
| PEG-200 Hydrogenated Glyceryl Palmate | 1.0 |
| Sodium Lactate | 1.0 |
| Sodium Chloride | 0.7 |
| Tetrasodium Glutamate Diacetate | 0.2 |
| Linalool | 0.1 |
| Limonene | 0.1 |
| Citronellol | 0.1 |
| Dyes | q.s. |

Example Formulation 86: Soap

| Ingredient | % |
|---|---|
| Aqua | ad 100 |
| Cocamidopropyl Betaine | 5.0 |
| Glycolipids | 2.5 |
| Glucolipid | 4.0 |
| Glycerin | 2.7 |
| PEG-7 Glyceryl Cocoate | 2.5 |
| *Simmondsia Chinensis* (Jojoba) Seed Oil | 2.5 |
| Glyceryl Glucoside | 2.3 |
| Mel | 2.0 |
| Sodium Laureth Sulfate | 3.0 |
| Sodium Chloride | 2.1 |
| Citric Acid | ad pH 5.0 |
| PEG-40 Hydrogenated Castor Oil | 1.8 |
| PEG-120 Methyl Glucose Dioleate | 1.7 |
| Trisodium EDTA | 1.0 |
| Glycol Distearate | 1.0 |
| Polyquaternium-10 | 0.3 |
| Laureth-10 | 0.7 |
| Benzophenone-4 | 0.5 |
| Cocamide MEA | 0.8 |
| Maltodextrin | 0.5 |
| Sodium Benzoate | 0.7 |
| Sodium Salicylate | 0.6 |
| Benzoic Acid | 0.4 |
| Linalool | 0.1 |
| Parfum, Dyes | q.s. |

Example Formulation 87: Caring Liquid Soap

| Ingredient | % |
|---|---|
| Aqua | ad 100 |
| Aloe Barbadensis Leaf Juice | 5.0 |
| Ammonium Lauryl Sulfate | 5.0 |
| Coco Glucoside | 4.0 |

-continued

| Ingredient | % |
|---|---|
| Cocamidopropyl Betaine | 4.0 |
| Sodium Cocoamphoacetate | 1.5 |
| Glucolipid | 1.5 |
| Glycerin | 1.5 |
| Sodium Chloride | 1.5 |
| Citric Acid | ad pH 5.5 |
| Sodium Benzoate | 1.0 |
| Sodium Salicylate | 0.5 |
| Methylisothiazolinone | 0.3 |
| Linalool | 0.1 |
| Butylphenyl Methylpropional | 0.2 |
| Limonene | 0.1 |
| Dyes | q.s. |

Example Formulation 88: Cream Soap

| Ingredient | % |
|---|---|
| Aqua | ad 100 |
| Alcohol | 5.0 |
| Coco Glucoside | 5.0 |
| Glycerin | 5.0 |
| Glucolipid | 2.5 |
| Disodium Cocoyl Glutamate | 2.0 |
| Xanthan Gum | 1.5 |
| Citric Acid | ad pH 5.5 |
| Malva Sylvestris Leaf Extract | 1.0 |
| Sodium Lauroyl Lactylate | 1.0 |
| Glyceryl Oleate | 1.0 |
| Sodium Cocoyl Glutamate | 0.7 |
| Linalool | 0.1 |
| Limonene | 0.1 |
| Dyes | q.s. |

Example Formulation 89: Liquid Soap

| Ingredient | % |
|---|---|
| Aqua | ad 100 |
| Sodium Laureth Sulfate | 5.0 |
| Sodium Chloride | 3.5 |
| Cocamidopropyl Betaine | 3.5 |
| Coco Glucoside | 3.0 |
| Glucolipid | 2.0 |
| Glyceryl Oleate | 1.0 |
| Hibiscus Sabdariffa Flower Extract | 1.0 |
| Alcohol | 1.0 |
| Sodium Lactate | 1.0 |
| Citric Acid | ad pH 5.0 |
| Sodium Benzoate | 0.7 |
| Potassium Sorbate | 0.1 |
| Parfum, Dyes | q.s. |

Example Formulation 90: Liquid Soap

| Ingredient | % |
|---|---|
| Aqua | ad 100 |
| Glycerin | 7.0 |
| Alcohol | 4.0 |
| Sodium Coco Sulfate | 3.0 |
| Lauryl Glucoside | 2.5 |
| Glucolipid | 2.0 |
| Xanthan Gum | 1.5 |
| *Mangifera Indica* (Mango) Fruit Extract | 0.7 |
| Limonene | 0.1 |
| Linalool | 0.1 |
| Dyes | q.s. |

Example Formulation 91: Liquid Soap

| Ingredient | % |
|---|---|
| Aqua | ad 100 |
| Sodium Lauryl Sulfate | 6.0 |
| Cocamidopropyl Betaine | 3.0 |
| Glucolipid | 3.0 |
| Triethylcitrate; Caprylyl Glycol; Benzoic Acid | 1.0 |
| Lactic Acid | ad pH 5.0 |
| Chamomilla Recutita Extract | 0.5 |
| Sodium Chloride | 0.9 |
| Sodium Lactate | 0.7 |
| Styrene/Acrylates Copolymer | 0.5 |
| Glycerin | 0.5 |
| Polyquaternium-7 | 0.3 |
| Hexyl Cinnamal | 0.1 |
| Sorbitol | 0.2 |
| Trisodium Ethylenediamine Disuccinate | 0.2 |
| Propylene Glycol | 0.3 |
| PEG-40 Hydrogenated Castor Oil | 0.9 |
| 1,2-Hexandiol | 0.5 |
| Parfum, Dyes | q.s. |

Example Formulation 92: Cream Soap

| Ingredient | % |
|---|---|
| Aqua | ad 100 |
| Sodium Laureth Sulfate | 8.0 |
| Cocamidopropyl Betaine | 3.0 |
| Sodium Chloride | 2.6 |
| Glucolipid | 2.5 |
| Polyquaternium-7 | 0.4 |
| Glycerin | 0.9 |
| Glycol Distearate | 0.7 |
| Laureth-4 | 0.5 |
| Laureth-2 | 0.8 |
| PEG-55 Propylene Glycol Oleate | 0.4 |
| Propylene Glycol | 0.5 |
| Citric Acid | ad pH 5.5 |
| Hexyl Cinnamal | 0.1 |
| Benzyl Salicylate | 0.1 |
| Linalool | 0.1 |
| Limonene | 0.1 |
| Butylphenyl Methylpropional | 0.1 |
| Sodium Benzoate | 0.1 |
| Dyes | q.s. |

Example Formulation 93: Jelly Soap

| Ingredient | % |
|---|---|
| Glycerin | 50.0 |
| Decyl Glucoside | 5.0 |
| Sophorolipid | 3.0 |
| Glucolipid | 2.5 |
| Chondrus Crispus Powder | 2.0 |
| Methylpropanediol | 1.0 |
| Caprylyl Glycol | 1.0 |
| Phenylpropanol | 0.5 |
| Parfum | 0.2 |
| *Helianthus Annuus* (Sunflower) Seed Oil | 0.2 |
| Hydrogenated Coconut Oil | 0.2 |
| *Olea Europea* (Olive) Fruti Oil | 0.2 |
| *Oryza Sativa* (Rice) Bran Oil | 0.2 |
| *Vitis Vinifera* (Grape) Seed Oil | 0.1 |
| *Prunus Amygdalus Dulcis* (Sweet Almond) Oil | 0.1 |
| Aqua | ad 100 |
| Sodium Benzoate | 0.1 |
| Citric Acid | 0.1 |

Example Formulation 94: Soap

| Ingredient | % |
|---|---|
| Talc | 65.0 |
| Glucolipid | 10.0 |
| Corn (*Zea Mays*) Flour | 9.0 |
| Glycerin | 7.0 |
| Sodium Laureth Sulfate | 4.5 |
| Citrus Aurantium Bergamia Fruit Oil | 3.5 |
| Benzyl Benzoate | 0.5 |
| Butylphenyl Methylpropional | 0.2 |
| Parfum | 0.2 |

Example Formulation 95: Soap

| Ingredient | % |
|---|---|
| Aqua | ad 100 |
| Glucolipid | 6.0 |
| Glycolipids | 5.0 |
| Propylene Glycol | 5.0 |
| Helianthus Annuus Seed Oil | 4.0 |
| Cocos Nucifera Oil | 4.0 |
| Titanium Dioxide | 0.2 |
| Sodium Hydroxide | 0.2 |
| Sodium Coco-sulfate | 0.2 |
| Parfum | 0.1 |
| Sodium Chloride | 0.1 |
| L-limonene | 0.1 |

Example Formulation 96: Painting Soap

| Ingredient | % |
|---|---|
| Aqua | ad 100 |
| Mica | 7.0 |
| Glycine Soja Oil | 5.0 |
| Glycerin | 4.0 |
| Alcohol | 3.0 |
| Cocamidopropyl Betaine | 3.0 |
| Glucolipid | 2.0 |
| Cetearyl Alcohol | 1.5 |
| Myristyl Alcohol | 1.0 |
| Glyceryl Stearate Citrate | 1.0 |
| Parfum | 0.4 |
| Xanthan Gum | 0.3 |
| Helianthus Annuus Seed Oil | 0.2 |
| Simmondsia Chinensis Seed Oil | 0.2 |
| Rubus Idaeus Fruit Extract | 0.2 |
| Tocopherol | 0.1 |

Example Formulation 97: Painting Soap

| Ingredient | % |
|---|---|
| Aqua | ad 100 |
| Glycerin | 10.0 |
| *Zea* Starch | 9.0 |
| Lauryl Glucoside | 4.0 |
| Methylpropanediol | 3.0 |
| Stearyl Alcohol | 3.0 |
| Cocamidopropyl Betaine | 2.0 |
| Glucolipid | 2.0 |
| Glycine Soja Oil | 1.0 |
| Tocopherol | 0.5 |
| Coco-Glucoside | 0.4 |
| Panthenol | 0.2 |
| Glycerin Oleate | 0.2 |
| Caprylyl Glycol | 0.2 |
| Phenlypropanol | 0.2 |
| Sodium Hydroxide | 0.1 |
| Sodium Chloride | 0.1 |

-continued

| Ingredient | % |
| --- | --- |
| Xanthan Gum | 0.1 |
| Citric Acid | 0.1 |
| Parfum | 0.1 |
| Beta Carotene | 0.1 |
| Dyes | q.s. |

Bath

Example Formulation 98: Bath

| Ingredient | % |
| --- | --- |
| Aqua | ad 100 |
| PEG-80 Sorbitan Laurate | 4.0 |
| Cocamidopropyl Betaine | 4.0 |
| Sodium Laureth Sulfate | 4.0 |
| Glucolipid | 2.0 |
| Polysorbate 20 | 2.0 |
| Sodium Chloride | 1.5 |
| Citric Acid | ad pH 5.0 |
| Sodium Lauroamphoacetate | 1.0 |
| PEG-150 Distearate | 1.0 |
| Disodium Lauroamphodiacetate | 1.0 |
| Sodium Benzoate | 0.5 |
| Parfum, Dyes | q.s. |

Example Formulation 99: Creme Oil Bath

| Ingredient | % |
| --- | --- |
| Aqua | ad 100 |
| Sodium Laureth Sulfate | 5.0 |
| Cocamidopropyl Betaine | 3.0 |
| Decyl Glucoside | 2.8 |
| Glucolipid | 2.5 |
| Glycerin | 2.5 |
| Glyceryl Glucoside | 2.0 |
| Diamond Powder | 2.0 |
| *Helianthus Annuus* (Sunflower) Seed Oil | 1.7 |
| Sodium Chloride | 1.5 |
| Glycol Distearate | 1.5 |
| PEG-40 Hydrogenated Castor Oil | 1.5 |
| Citric Acid | ad pH 5.5 |
| PEG-90 Glyceryl Isostearate | 1.2 |
| Laureth-4 | 1.0 |
| PEG-200 Hydrogenated Glyceryl Palmate | 1.0 |
| PEG-7 Glyceryl Cocoate | 1.0 |
| Benzophenone-4 | 0.9 |
| Laureth-2 | 0.7 |
| Sodium Benzoate | 0.7 |
| Butylphenyl Methylpropional | 0.1 |
| Linalool | 0.1 |
| Limonene | 0.1 |
| alpha-Isomethyl Ionone | 0.1 |
| Dyes | q.s. |

Example Formulation 100: Relaxing Good Sleep Bath

| Ingredient | % |
| --- | --- |
| Aqua | ad 100 |
| Cocamidopropyl Betaine | 3.0 |
| Coco Glucoside | 2.5 |
| Sodium Chloride | 2.5 |
| Disodium Lauryl Sulfosuccinate | 2.0 |
| Glucolipid | 2.0 |
| Glycerin | 1.7 |
| Sodium PCA | 0.5 |
| Glyceryl Oleate | 0.4 |
| Sodium Hydroxide | 0.3 |
| Citric Acid | ad pH 5.5 |

-continued

| Ingredient | % |
| --- | --- |
| Linalool | 0.1 |
| Limonene | 0.1 |
| Geraniol | 0.1 |
| Dyes | q.s. |

Example Formulation 51: Pampering Oil Bath

| Ingredient | % |
| --- | --- |
| Aqua | ad 100 |
| Glycine Soja Oil | 20.0 |
| Glucolipid | 5.0 |
| Polyglyceryl-3 Palmitate | 4.5 |
| Glyceryl Caprylate | 1.5 |
| Simmondsia Chinensis Oil | 1.5 |
| *Prunus Amygdalus Dulcis* (Sweet Almond) Oil | 1.0 |
| Triticum Vulgare Germ Oil | 1.0 |
| Tocopherol | 0.2 |
| Limonene | 0.1 |
| Linalool | 0.1 |
| p-Anisic Acid | 0.1 |
| Dyes | q.s. |

Example Formulation 101: Aroma Bath

| Ingredient | % |
| --- | --- |
| Aqua | ad 100 |
| Alcohol | 5.0 |
| Coco Glucoside | 5.0 |
| Sodium Coco Sulfate | 4.0 |
| Glucolipid | 2.5 |
| Xanthan Gum | 1.9 |
| Glycerin | 1.8 |
| Sodium Cocoyl Glutamate | 1.5 |
| Disodium Cocoyl Glutamate | 1.5 |
| Melissa Officinalis Extract | 1.0 |
| Lavandula Angustifolia Oil | 1.0 |
| Linalool | 0.1 |
| Limonene | 0.1 |
| Geraniol | 0.1 |
| Dyes | q.s. |

Example Formulation 102: Bath Bomb

| Ingredient | % |
| --- | --- |
| Sodium Bicarbonate | 70.0 |
| Citric Acid | 8.0 |
| Citrus Nobilis Oil | 6.0 |
| Potassium Tartrate | 6.0 |
| Sodium Laureth Sulfate | 4.0 |
| Glucolipid | 4.0 |
| Betaine | 1.5 |
| Parfum | 0.5 |
| Dyes | q.s. |

Example Formulation 103: Bath Bomb

| Ingredient | % |
| --- | --- |
| Sodium Bicarbonate | 67.0 |
| Citric Acid | 9.0 |
| *Zea Mays* Starch | 8.0 |
| Butyrospermum Parkii Butter | 5.0 |
| Sodium Lauryl Sulfoacetate | 4.0 |
| Glucolipid | 4.0 |
| *Theobroma Cacao* Seed Butter | 2.0 |

-continued

| Ingredient | % |
| --- | --- |
| *Theobroma Cacao* (Cocoa) Fruit Powder | 1.0 |
| Parfum, Dyes | q.s. |

Example Formulation 104: Bath Salt

| Ingredient | % |
| --- | --- |
| Maris Sal | ad 100 |
| Parfum | 2.0 |
| Glycolipids | 1.0 |
| Glucolipid | 1.0 |
| Silica | 0.5 |
| Simmondsia Chinensis Seed Oil | 0.1 |
| Preservative, Dyes | q.s. |

Example Formulation 105: Bath Salt

| Ingredient | % |
| --- | --- |
| Maris Sal | ad 100 |
| Rosmarinus Officinalis Leaf Oil | 3.0 |
| Parfum | 1.5 |
| Polysorbate 20 | 1.5 |
| Glucolipid | 1.5 |
| Preservative, Dyes | q.s. |

x-in-1

Example Formulation 106: Shower Gel and Shampoo

| Ingredient | % |
| --- | --- |
| Aqua | ad 100 |
| Coco Glucoside | 5.0 |
| Sodium Coco Sulfate | 3.0 |
| Cocamidopropyl Hydroxysultaine | 2.5 |
| Glucolipid | 2.0 |
| Sophorolipid | 2.0 |
| Glyceryl Oleate | 1.8 |
| Inulin | 1.5 |
| Lecithin | 1.5 |
| Polyquaternium-39 | 1.5 |
| Citric Acid | ad pH 5.0 |
| Styrene/Acrylates Copolymer | 1.0 |
| Sodium Chloride | 1.0 |
| Denatonium Benzoate | 0.5 |
| Hydrogenated Palm Glycerides Citrate | 0.7 |
| Tocopherol | 0.3 |
| Sodium Benzoate | 0.7 |
| Phenoxyethanol | 0.3 |
| Parfum, Dyes | q.s. |

Example Formulation 107: Shower, Shampoo and Shave

| Ingredient | % |
| --- | --- |
| Aqua | ad 100 |
| Cocamidopropyl Betaine | 5.0 |
| Sodium Laureth Sulfate | 4.0 |
| PEG-7 Glyceryl Cocoate | 4.0 |
| Sodium Chloride | 3.5 |
| Glucolipid | 2.0 |
| PEG-3 Distearate | 3.0 |
| Glycerin | 2.5 |
| Glyceryl Glucoside | 1.2 |
| *Helianthus Annuus* (Sunflower) Seed Oil | 1.0 |
| *Persea Gratissima* (Avocado) Oil | 1.0 |
| Polyquaternium-7 | 1.0 |

-continued

| Ingredient | % |
| --- | --- |
| PEG-90m | 1.0 |
| PEG-40 Hydrogenated Castor Oil | 1.0 |
| Citric Acid | ad pH 5.0 |
| Benzophenone-4 | 0.5 |
| PEG-200 Hydrogenated Glyceryl Palmate | 0.5 |
| Silica | 0.7 |
| Sodium Benzoate | 0.6 |
| Methylparaben | 0.4 |
| Propylparaben | 0.4 |
| Limonene | 0.1 |
| Butylphenyl Methylpropional | 0.1 |
| Benzyl Alcohol | 0.1 |
| Dyes | q.s. |

Example Formulation 108: 2-in-1 Body Wash and Shampoo

| Ingredient | % |
| --- | --- |
| Aqua | ad 100 |
| Sodium Laureth Sulfate | 8.5 |
| Glycerin | 2.5 |
| Sodium Cocoyl Isethionate | 2.5 |
| Ammonium Lauryl Sulfate | 2.5 |
| Lauryl Betaine | 2.5 |
| Lauryl Glucoside | 1.5 |
| Sodium Chloride | 1.0 |
| Glucolipid | 1.0 |
| Polyquaternium-39 | 0.5 |
| Polyquaternium-7 | 0.5 |
| Panthenol | 0.1 |
| Citric Acid | ad pH 5.5 |
| Sodium Citrate | 0.2 |
| Propylene Glycol | 0.3 |
| PEG-55 Propylene Glycol Oleate | 0.7 |
| Styrene/Acrylates Copolymer | 0.2 |
| Phenoxyethanol | 0.7 |
| Sodium Benzoate | 0.3 |
| Tetrasodium EDTA | 0.1 |
| Parfum, Dyes | q.s. |

Example Formulation 109: 2-in-1 Bubble Bath and Wash

| Ingredient | % |
| --- | --- |
| Aqua | ad 100 |
| Cocamidopropyl Betaine | 4.0 |
| Glycerin | 4.0 |
| Sodium Lauroamphodiacetate | 2.0 |
| Sodium Chloride | 2.0 |
| Coco Glucoside | 1.5 |
| Hydroxypropyl Starch Phosphate | 1.0 |
| Disodium Lauroamphodiacetate | 1.0 |
| Glucolipid | 1.0 |
| Lauric Acid | 1.0 |
| Acrylates/C10-30 Alkyl Acrylate Crosspolymer | 1.0 |
| Polyquaternium-7 | 1.0 |
| Styrene/Acrylates Copolymer | 0.5 |
| Citric Acid | ad pH 5.5 |
| Sodium Hydroxide | 0.3 |
| Sodium Benzoate | 0.2 |
| Benzoic Acid | 0.1 |
| Parfum, Dyes | q.s. |

Example Formulation 110: Body and Face Wash

| Ingredient | % |
| --- | --- |
| Aqua | ad 100 |
| Sodium Laureth Sulfate | 4.5 |
| Petrolatum | 3.0 |

-continued

| Ingredient | % |
|---|---|
| Acrylates Copolymer | 2.5 |
| Cocamide MEA | 2.5 |
| Sophorolipid | 2.5 |
| Glucolipid | 2.0 |
| PPG-9 | 2.0 |
| Menthol | 0.2 |
| DMDM Hydantoin | 0.1 |
| Tetrasodium EDTA | 0.2 |
| Methylisothiazolinone | 0.1 |
| BHT | 0.1 |
| Parfum, Dyes | q.s. |

Example Formulation 111: Hair and Body Shampoo

| Ingredient | % |
|---|---|
| Aqua | ad 100 |
| Sodium Laureth Sulfate | 10.0 |
| Sodium Chloride | 4.0 |
| Glycerin | 3.5 |
| Coco-Betaine | 2.0 |
| Glucolipid | 2.0 |
| Niacinamide | 0.1 |
| *Saccharum Officinarum* (Sugar Cane) Extract | 1.0 |
| Sodium Benzoate | 1.0 |
| Sodium Hydroxide | 0.3 |
| PPG-5-Ceteth-20 | 1.0 |
| Polyquaternium-10 | 0.7 |
| Salicylic Acid | 0.5 |
| Limonene | 0.1 |
| Linalool | 0.2 |
| Benzyl Salicylate | 0.1 |
| *Pyrus Malus* (Apple Fruit) Extract | 0.3 |
| Pyridoxine HCl | 0.2 |
| Citric Acid | ad pH 5.0 |
| Taurine | 0.1 |
| Dyes | q.s. |

Example Formulation 112: After-Sun Hair and Body Shampoo

| Ingredient | % |
|---|---|
| Aqua | ad 100 |
| Sodium Laureth Sulfate | 7.0 |
| Cocamidopropyl Betaine | 5.0 |
| PEG-18 Glyceryl Oleate/Cocoate | 2.5 |
| Glucolipid | 2.0 |
| Glycol Distearate | 2.0 |
| Coco Glucoside | 2.0 |
| Laureth-4 | 1.5 |
| Sodium Chloride | 0.9 |
| Panthenol | 0.1 |
| Sodium PCA | 0.7 |
| Polyquaternium-10 | 0.3 |
| Octyldodecyl PCA | 0.2 |
| Glycerin | 0.9 |
| PPG-9 | 0.7 |
| Citric Acid | ad pH 5.5 |
| Tetrasodium EDTA | 0.3 |
| Quaternium-80 | 0.2 |
| Propylene Glycol | 0.3 |
| Isopropyl Alcohol | 0.3 |
| Sodium Benzoate | 0.7 |
| Limonene | 0.1 |
| Linalool | 0.1 |
| Benzyl Salicylate | 0.1 |
| Butylphenyl Methylpropional | 0.1 |
| Ceramide NP | 0.05 |
| Dyes | q.s. |

Example Formulation 113: Hair and Body Shampoo & Shower Gel

| Ingredient | % |
|---|---|
| Aqua | ad 100 |
| Sodium Laureth Sulfate | 7.0 |
| Sodium Chloride | 3.8 |
| Cocamidopropyl Betaine | 3.5 |
| Glucolipid | 3.0 |
| Panthenol | 0.3 |
| Hydrolyzed Keratin | 0.7 |
| Taurine | 0.5 |
| Simmondsia Chinensis Seed Oil | 0.5 |
| Disodium Cocoamphodiacetate | 0.5 |
| Citric Acid | ad pH 5.0 |
| Sodium Benzoate | 0.7 |
| Cocamide MEA | 0.4 |
| PEG-7 Glyceryl Cocoate | 0.3 |
| Polyquaternium-10 | 0.2 |
| Propylene Glycol | 0.3 |
| PEG-40 Hydrogenated Castor Oil | 0.4 |
| Linalool | 0.2 |
| Geraniol | 0.1 |
| Butylphenyl Methylpropional | 0.1 |
| Dyes | q.s. |

Facial Cleansing—Example Formulations

Example Formulation 114: Eye Make-Up Remover

| Ingredient | % |
|---|---|
| Aqua | ad 100 |
| Butylene Glycol | 6.0 |
| Propanediol | 2.0 |
| Decyl Glucoside | 1.0 |
| Glucolipid | 1.0 |
| Glycerin | 1.0 |
| Aloe Barbadensis Leaf Extract | 0.5 |
| Citric Acid | ad pH 7 |
| Bioflavonoids | 0.1 |
| Pantolactone | 0.1 |

Example Formulation 115: Eye Make-Up Remover

| Ingredient | % |
|---|---|
| Aqua | ad 100 |
| Cyclopentasiloxane | 8.0 |
| Glycerin | 6.0 |
| Isohexadecane | 6.0 |
| Butylene Glycol | 4.0 |
| Panthenol | 3.0 |
| Glucolipid | 3.0 |
| Sodium Chloride | 2.0 |
| Disodium EDTA | 1.0 |
| Sodium Hydroxide | 0.2 |
| Citric Acid | ad pH 7 |
| Phenoxyethanol | 0.2 |
| Methylparaben | 0.1 |

Example Formulation 116: Micellar Lotion

| Ingredient | % |
|---|---|
| Aqua | ad 100 |
| Poloxamer 124 | 2.0 |
| Glucolipid | 2.0 |
| Glyceryl Glucoside | 1.5 |
| Glycerin | 1.0 |
| Polyglyceryl-10 Laurate | 1.0 |
| 1,2-Hexandiol | 1.0 |
| Decyl Glucoside | 0.5 |

-continued

| Ingredient | % |
|---|---|
| Arginine HCl | 0.3 |
| Sodium Cocoamphoacetate | 0.5 |
| Trisodium EDTA | 0.2 |
| Citric Acid | ad pH 6.5 |
| Phenoxyethanol | 0.1 |
| Sodium Hyaluronate | 0.05 |

Example Formulation 117: Waterproof Eye Make-Up Removal

| Ingredient | % |
|---|---|
| Aqua | ad 100 |
| Aloe Barbadensis Leaf Juice | 5.0 |
| Sorbitol | 3.0 |
| Glycerin | 3.0 |
| Panthenol | 2.2 |
| Sodium Lauryl Glucose Carboxylate | 2.0 |
| Biosaccharide Gum-1 | 1.5 |
| Lauryl Glucoside | 1.0 |
| Glucolipid | 0.5 |
| Allantoin | 0.2 |
| Phenoxyethanol | 0.2 |
| Sodium Benzoate | 0.2 |
| Sorbic Acid | q.s. |
| Citric Acid | ad pH 6 |

Example Formulation 118: Waterproof Eye Make-Up Removal

| Ingredient | % |
|---|---|
| Aqua | ad 100 |
| Isododecane | 6.0 |
| Isopropyl Palmitate | 4.0 |
| Dimethicone | 3.0 |
| Sodium Ascorbyl Phosphate | 2.0 |
| Sodium Chloride | 2.0 |
| Glucolipid | 1.5 |
| Caprylyl/Capryl Glucoside | 1.5 |
| Trisodium EDTA | 1.0 |
| Citric Acid | ad pH 7 |
| Sodium Hydroxide | 0.2 |
| Phenoxyethanol | 0.2 |
| Benzethonium Chloride | 0.2 |

Example Formulation 119: Micellar Gel

| Ingredient | % |
|---|---|
| Aqua | ad 100 |
| Propanediol | 5.0 |
| Glucolipid | 3.0 |
| Glycerin, Aqua, Sodium Levulinate, Sodium Anisate | 3.0 |
| Polyglyceryl-4 Caprate | 2.0 |
| Xanthan Gum | 1.5 |
| Lactobacillus Ferment | 0.05 |
| Lactic Acid | ad pH 5.5 |

Example Formulation 120: Micellar Gel

| Ingredient | % |
|---|---|
| Aqua | ad 100 |
| Propylene Glycol | 4.0 |
| Glycerin | 4.0 |
| Poloxamer 124 | 2.5 |

-continued

| Ingredient | % |
|---|---|
| Glucolipid | 2.5 |
| 1,2-Hexandiol | 2.0 |
| Pentylene Glycol | 1.0 |
| Acrylates/C10-30 Alkyl Acrylate Crosspolymer | 0.5 |
| Sodium Hyaluronate | 0.2 |
| Trisodium EDTA | 0.1 |
| Sodium Hydroxide | ad pH 6 |
| Cetrimonium Chloride | 0.1 |
| Phenoxyethanol | 0.1 |

Example Formulation 121: Micellar Make-Up Remover

| Ingredient | % |
|---|---|
| Aqua | ad 100 |
| Aloe Barbadensis Leaf Juice | 4.0 |
| Caprylyl/Capryl Glucoside | 2.0 |
| Glycolipids | 1.5 |
| Glucolipid | 1.5 |
| Betaine | 1.0 |
| Glycerin | 1.0 |
| Benzyl Alcohol, Caprylyl Glycol, Benzoic Acid | 1.0 |
| Decyl Glucoside | 0.5 |
| Parfum | q.s. |
| Citric Acid | ad pH 7.0 |

Example Formulation 122: Facial Cleansing Foam

| Ingredient | % |
|---|---|
| Aqua | ad 100 |
| Glycine Soja Oil | 5.0 |
| Coco-Glucoside | 4.0 |
| Glycerin | 3.5 |
| Glucolipid | 3.0 |
| Alcohol Denat. | 2.0 |
| Sodium Coco-Sulfate | 1.5 |
| Sodium/Disodium Cocoyl Glutamate | 1.0 |
| Sophorolipid | 0.8 |
| Glyceryl Oleate | 0.5 |
| Hamamelis Virginiana Leaf Extract | 0.5 |
| Tocopherol | 0.1 |
| Helianthus Annuus Seed Oil | 0.1 |
| Lactic Acid | ad pH 6.5 |
| Preservative | q.s. |

Example Formulation 123: Facial Cleansing Foam

| Ingredient | % |
|---|---|
| Aqua | ad 100 |
| Sodium/Disodium Cocoyl Glutamate | 4.0 |
| Glucolipid | 4.0 |
| Sodium Lauryl Sulfate | 3.0 |
| Parfum | 1.0 |
| Benzyl Alcohol, Caprylyl Glycol, Benzoic Acid | 1.0 |
| Glycerin | 0.8 |
| Sodium Lauryl Glucose Carboxylate | 0.7 |
| Sodium Cottonseedamphoacetate | 0.7 |
| Lauryl Glucoside | 0.5 |
| Citric Acid | ad pH 7.0 |
| Capryloyl Glycine | 0.2 |
| Sodium Hydroxide | 0.2 |
| 1,2-Hexandiol | 0.2 |
| Allantoin | 0.1 |
| Hydroxypropyl Guar Hydroxypropyltrimonium Chloride | 0.1 |
| Tetrasodium EDTA | 0.1 |
| Dehydroacetic Acid | 0.1 |

-continued

| Ingredient | % |
| --- | --- |
| Sorbic Acid | 0.1 |
| Tropolone | 0.1 |

Example Formulation 124: Cleansing Foam

| Ingredient | % |
| --- | --- |
| Aqua | ad 100 |
| Coco-Glucoside | 2.0 |
| Glycerin | 1.5 |
| Sodium Coco-Sulfate | 1.5 |
| Glyceryl Oleate | 1.0 |
| Decyl Glucoside | 0.5 |
| Sodium Benzoate | 0.5 |
| Citric Acid | ad pH 5.0 |
| Panthenol | 0.4 |
| Glucolipid | 0.2 |
| Albumen | 0.1 |
| Potassium Sorbate | 0.1 |
| Tocopherol | 0.1 |
| Hydrogenated Palm Glycerides Citrate | 0.1 |

Example Formulation 125: Cleansing Foam

| Ingredient | % |
| --- | --- |
| Aqua | ad 100 |
| Aloe Barbadensis Leaf Juice | 28.0 |
| Glycerin | 7.0 |
| Decyl Glucoside | 5.0 |
| Ammonium Lauryl Sulfate | 2.0 |
| Benzyl Alcohol, Caprylyl Glocol, Benzoic Acid | 2.0 |
| Parfum | 0.8 |
| Glucolipid | 0.1 |
| Phytic Acid | 0.1 |
| Sodium Hydroxide | ad pH 7.0 |
| Gluconolactone | 0.1 |

Example Formulation 126: Cleansing Foam

| Ingredient | % |
| --- | --- |
| Aqua | ad 100 |
| Glycerin | 3.0 |
| Decyl Glucoside | 3.0 |
| Glycolipids | 2.0 |
| Pentylene Glycol | 2.0 |
| Glucolipid | 1.0 |
| Citric Acid | ad pH 6.0 |
| Papain | 0.1 |

Example Formulation 127: Pump Foam for Facial Cleansing

| Ingredient | % |
| --- | --- |
| Aqua | ad 100 |
| Sorbitol | 9.0 |
| Glycerin | 5.0 |
| Decyl Glucoside | 4.0 |
| Disodium Cocoyl Glutamate | 4.0 |
| Glyceryl Glucoside | 2.0 |
| Glucolipid | 2.0 |
| Propylene Glycol | 2.0 |
| Prunus Amygdalus Dulcis Oil | 2.0 |
| PEG-40 Hydrogenated Castor Oil | 1.5 |
| Sodium Sulfate | 0.5 |
| Citric Acid | ad pH |
| Polyquaternium-10 | 0.5 |

-continued

| Ingredient | % |
| --- | --- |
| Sodium Benzoate | 0.2 |
| Aminopeptidase | 0.1 |
| Panthenol | 0.1 |

Example Formulation 128: Pump Foam for Facial Cleansing

| Ingredient | % |
| --- | --- |
| Aqua | ad 100 |
| Sucrose | 12.0 |
| Glycerin | 6.0 |
| Rosa Damascena Flower Water | 5.0 |
| Coco-Glucoside | 4.5 |
| Glucolipid | 2.5 |
| Aqua, Sodium Levulinate, Potassium Sorbate | 2.0 |
| Sodium Cocoyl Glutamate | 3.0 |
| Polyglyceryl-4 Caprate | 3.0 |
| Betaine | 1.0 |
| Citric Acid | ad pH 5.0 |
| Parfum | 0.8 |
| Sodium Chloride | 0.5 |

Example Formulation 129: Micellar Water

| Ingredient | % |
| --- | --- |
| Aqua | ad 100 |
| PEG-6 Caprylic/capric Glycerides | 3.0 |
| Polysorbate 20 | 2.0 |
| Glucolipid | 0.8 |
| Butylene Glycol | 0.5 |
| PEG-8 | 0.4 |
| Poloxamer 407 | 0.4 |
| Disodium EDTA | 0.3 |
| Citric Acid | ad pH 6.5 |
| BHT | 0.2 |
| Sodium Benzoate | 0.2 |

Example Formulation 130: Refreshing Micellar Water

| Ingredient | % |
| --- | --- |
| Aqua | ad 100 |
| Methylpropanediol | 3.0 |
| Propylene Glycol | 2.5 |
| Glycerin | 2.5 |
| Sodium Cocoamphoacetate | 2.0 |
| Glycolipids | 1.5 |
| Parfum | 0.8 |
| Glucolipid | 0.5 |
| Sodium Salicylate | 0.5 |
| Sodium Benzoate | 0.5 |
| Citric Acid | ad pH |
| Sodium Chloride | 0.2 |
| Tetrasodium EDTA | 0.1 |

Example Formulation 131: Oil-Infused Micellar Water

| Ingredient | % |
| --- | --- |
| Aqua | ad 100 |
| Isododecane | 7.5 |
| Dimethicone | 7.5 |
| Dicaprylyl Ether | 5.0 |
| Hexylene Glycol | 1.4 |
| Propanediol | 1.0 |
| Glucolipid | 1.0 |
| Sophorolipid | 1.0 |

-continued

| Ingredient | % |
|---|---|
| Sodium Chloride | 1.0 |
| Trisiloxane | 0.8 |
| Alcohol Denat. | 0.8 |
| Glycerin | 0.8 |
| Propylene Glycol Dicaprylate/Dicaprate | 0.8 |
| Disodium EDTA | 0.5 |
| Hydroxyethylcellulose | 0.5 |
| Phenoxyethanol, Benzoic Acid | 0.5 |
| Decyl Glucoside | 0.5 |
| Caprylyl Glycol | 0.5 |
| Sodium Citrate | 0.3 |
| Citric Acid | ad pH 6 |
| Panthenol | 0.2 |
| Benzophenone-3 | 0.1 |
| Tocopheryl Acetate | 0.1 |
| Tocopherol | 0.1 |
| *Zea Mays* Oil | 0.1 |
| Chlorphenesin | 0.1 |

Example Formulation 132: Facial Tonic

| Ingredient | % |
|---|---|
| Aqua | ad 100 |
| Glycerin. | 2.5 |
| Propanediol | 2.0 |
| Arginine | 1.0 |
| Glucolipid | 1.0 |
| Salicylic Acid | 1.0 |
| Coco-Betaine | 1.0 |
| Caprylyl/Capryl Glucoside | 0.8 |
| Disodium Cocoyl Glutamate | 0.8 |
| Xanthan Gum | 0.5 |
| Phytic Acid | 0.5 |
| Sodium Chloride | 0.5 |
| Sodium Cocoyl Glutamate | 0.4 |
| Citric Acid | ad pH 5.5 |

Example Formulation 133: Facial Tonic

| Ingredient | % |
|---|---|
| Aqua | ad 100 |
| Glycerin | 5.0 |
| Caprylyl/Capryl Glucoside | 2.0 |
| Glucolipid | 1.5 |
| Glyceryl Caprylate | 1.5 |
| Parfum | 1.0 |
| Sodium Levulinate | 1.0 |
| Sodium Anisate | 1.0 |
| Sodium Salicylate | 1.0 |
| Sodium Cocoyl Glutamate | 0.1 |
| Polyglyceryl-6 Oleate | 0.1 |
| Disodium Cocoyl Glutamate | 0.1 |
| Citric Acid | ad pH 5.5 |
| Sodium Surfactin | 0.05 |

Example Formulation 134: Facial Tonic

| Ingredient | % |
|---|---|
| Aqua | ad 100 |
| PEG-6 Caprylic/Capric Glycerides | 4.0 |
| Glucolipid | 3.0 |
| Fructooligosaccharides | 1.0 |
| Mannitol | 1.0 |
| Xylitol | 1.0 |
| Propylene Glycol | 1.0 |
| Cetrimonium Bromide | 1.0 |

-continued

| Ingredient | % |
|---|---|
| Disodium EDTA | 0.4 |
| Rhamnose | 0.1 |

Example Formulation 135: Micellar Water

| Ingredient | % |
|---|---|
| Aqua | ad 100 |
| Glycerin | 5.0 |
| Polyglyceryl-4 Caprate | 5.0 |
| Betaine | 3.0 |
| Glucolipid | 2.0 |
| Sodium Levulinate | 2.0 |
| Lactobacillus Ferment | 0.2 |
| Sodium Benzoate | 0.2 |
| Sodium Hydroxide | 0.2 |
| Parfum | 0.1 |
| Lactic Acid | ad pH 5.8 |

Example Formulation 136: Micellar Water

| Ingredient | % |
|---|---|
| Aqua | ad 100 |
| Glycerin | 6.0 |
| Poloxamer 184 | 2.5 |
| Phenoxyethanol | 1.0 |
| PEG-40 Hydrogenated Castor Oil | 1.0 |
| Lactobacillus Extract, Propylene Glycol | 0.8 |
| Glucolipid | 0.5 |
| Parfum | 0.5 |
| Citric Acid | ad pH 6.4 |
| Sodium Hydroxide | 0.2 |
| Disodium EDTA | 0.1 |

Example Formulation 137: Micellar Water

| Ingredient | % |
|---|---|
| Aqua | ad 100 |
| Glucolipid | 5.0 |
| PEG-40 Hydrogenated Castor Oil | 2.5 |
| Glycerin | 2.5 |
| Prunus Amygdalus Dulcis Oil | 1.0 |
| Sorbitol | 1.0 |
| Decyl Glucoside | 1.0 |
| 1,2-Hexandiol | 0.1 |
| Glyceryl Glucoside | 0.5 |
| Poloxamer 124 | 0.5 |
| Propylene Glycol | 0.5 |
| Disodium Cocoyl Glutamate | 0.5 |
| Sodium Chloride | 0.2 |
| Trisodium EDTA | 0.2 |
| Polyquaternium-10 | 0.2 |
| Citric Acid | ad pH 6.2 |
| Sodium Acetate | 0.1 |
| Phenoxyethanol | 0.1 |

Example Formulation 138: Micellar Water

| Ingredient | % |
|---|---|
| Aqua | ad 100 |
| Glucolipid | 5.0 |
| Glycerin | 4.0 |
| Coco-Glucoside | 2.0 |
| Polysorbate 80 | 0.2 |
| Calendula Officinalis Flower Extract | 2.0 |

-continued

| Ingredient | % |
| --- | --- |
| Caprylyl Glycol | 1.5 |
| Citric Acid | ad pH |
| Sodium Benzoate | 0.9 |
| Parfum | 0.6 |
| Isoleucine | 0.2 |
| Panthenol | 0.2 |
| PPG-1-PEG-9 Lauryl Glycol Ether | 0.2 |
| Propylene Glycol | 0.2 |
| Phytosphingosine | 0.1 |
| Sodium Chloride | 0.2 |

Example Formulation 139: Micellar Water

| Ingredient | % |
| --- | --- |
| Aqua | ad 100 |
| Hexylene Glycol | 1.4 |
| Glycerin | 1.2 |
| Glucolipid | 1.0 |
| Poloxamer 184 | 1.0 |
| Disodium Cocoamphodiacetate | 1.0 |
| Disodium EDTA | 0.5 |
| Polyaminopropyl Biguanide | 0.2 |
| Lactic Acid | ad pH 5.4 |

Example Formulation 140: Micellar Water

| Ingredient | % |
| --- | --- |
| Aqua | ad 100 |
| Glycerin | 5.0 |
| Alcohol Denat. | 2.0 |
| Sodium Lactate | 2.0 |
| Sodium PCA | 1.0 |
| Glucolipid | 0.5 |
| Parfum | 0.3 |
| Aloe Barbadensis Leaf Juice | 0.3 |
| Cocoyl Glutamic Acid | 0.2 |
| Sodium Cocoyl Glutamate | 0.2 |
| Glycolipids | 0.1 |
| Citric Acid | 0.1 |
| Lactic Acid | 0.1 |
| Sodium Hyaluronate | 0.1 |
| Phytosphingosine HCl | 0.1 |
| Benzyl Alcohol | 0.1 |

Example Formulation 141: Face Cleanser and Scrub

| Ingredient | % |
| --- | --- |
| Aqua | ad 100 |
| Sodium Coco-Sulfate | 4.0 |
| Glucolipid | 2.0 |
| Glycerin | 2.0 |
| Sodium Cocoyl Glycinate | 1.5 |
| Silica | 1.5 |
| Acrylates Copolymer | 0.8 |
| PEG-7 Glyceryl Cocoate | 0.7 |
| Sodium Chloride | 0.5 |
| Polysorbate 20 | 0.5 |
| Cocamidopropyl Betaine | 0.5 |
| Panthenol | 0.2 |
| Parfum | 0.2 |
| Charcoal Powder | 0.2 |
| *Salix Alba* (Willow) Bark Extract | 0.2 |
| Glycol Distearate | 0.1 |
| Lecithin | 0.1 |
| Laureth-4 | 0.1 |
| Citric Acid | ad pH 5.6 |
| Lactic Acid | 0.1 |

-continued

| Ingredient | % |
| --- | --- |
| Tocopherol | 0.1 |
| Ascorbyl Palmitate | 0.1 |
| Disodium EDTA | 0.1 |
| Phenoxyethanol | 0.1 |
| Ethylhexylglycerin | 0.1 |
| Sodium Benzoate | 0.1 |
| Benzyl Alcohol | 0.1 |
| Potassium Sorbate | 0.1 |

Microemulsionen

Example Formulation 142: Microemulsion for Make-Up Removal

| Ingredient | % |
| --- | --- |
| Water | ad 100 |
| 1,3-Butanediol | 15.0 |
| Polyglyceryl-4 Caprate | 6.0 |
| Polyglyceryl-3 Caprate | 6.0 |
| Glucolipid | 6.0 |
| Glycerin | 6.0 |
| Isohexadecane | 3.0 |
| Sodium Benzoate | 0.8 |
| Citric Acid | ad pH 5.0 |

Example Formulation 143: Microemulsion for Make-Up Removal

| Ingredient | % |
| --- | --- |
| Water | ad 100 |
| 1,3-Butanediol | 7.5 |
| Polyglyceryl-4 Caprate | 5.5 |
| Glycolipids | 3.0 |
| Glucolipid | 1.5 |
| Glycerin | 5.0 |
| Sodium Benzoate | 0.8 |
| Citric Acid | Ad pH 5.0 |

Toothpaste

Example Formulation 144: Toothpaste

| Ingredient | % |
| --- | --- |
| Aqua | ad 100 |
| Glycerin | 29.0 |
| Sodium Metaphosphate | 12.0 |
| Hydrated Silica (Hydrated) | 10.0 |
| Xylitol | 10.0 |
| Glucolipid | 1.0 |
| Olaflur | 0.13 |
| Cocamidopropyl Betaine | 0.5 |
| Propylene Glycol | 1.0 |
| Chamomilla Recutita Flower Extract | 0.4 |
| Alcohol Denat | 0.5 |
| Panthenol | 0.1 |
| Sodium Fluoride | 0.1 |
| Hydroxyethylcellulose | 1.0 |
| Titanium Dioxide | 0.4 |
| Aroma | 1.0 |
| Citronellol | 0.0 |
| Eucalyptol | 0.2 |
| Eugenol | 0.1 |
| Menthol | 0.15 |
| Dyes, pH adjuster, preservative | q.s. |

Example Formulation 145: Toothpaste

| Ingredient | % |
|---|---|
| Aqua | ad 100 |
| Hydrated Silica (Hydrated) | 22.0 |
| Sorbitol | 30.0 |
| Hydroxyethylcellulose | 1.5 |
| Glucolipid | 1.0 |
| Olaflur | 0.19 |
| Aroma | 1.0 |
| Limonene | 0.1 |
| Titanium Dioxide | 0.3 |
| Saccharin | 0.2 |
| Dyes, pH adjuster, preservative | q.s. |

Example Formulation 146: Toothpaste

| Ingredient | % |
|---|---|
| Sorbitol | 45.0 |
| Aqua | ad 100 |
| Hydrated Silica (Hydrated) | 18.0 |
| Sodium Lauryl Sulfate | 1.05 |
| Glucolipid | 0.75 |
| PEG-32 | 1.0 |
| Flavor | 1.0 |
| Cellulose Gum | 0.8 |
| Cocamidopropyl Betaine | 0.35 |
| Sodium Saccharin | 0.2 |
| Sodium Fluoride | 0.23 |
| Zinc Sulfate | 0.3 |
| Mica | 0.5 |
| Dyes solution (1% FD&C Blue No. 1) | 0.02 |
| Titanium Dioxide | 0.3 |
| Eugenol | 0.2 |
| pH adjuster, preservative | q.s. |

Example Formulation 147: Toothpaste

| Ingredient | % |
|---|---|
| Glycerin | 35.0 |
| Hydrated Silica (Hydrated) | 22.0 |
| Aqua | ad 100 |
| Sodium Bicarbonate | 20.0 |
| PEG-12 | 3.0 |
| Glucolipid | 1.5 |
| Sodium Lauryl Sulfate | 1.0 |
| Flavor | 1.0 |
| Sodium Hydroxide | 0.9 |
| Cellulose Gum | 0.9 |
| Chondrus Crispus | 0.5 |
| Sodium Saccharin | 0.1 |
| Calcium Peroxide | 0.1 |
| Titanium Dioxide | 0.4 |
| Sodium monofluorophosphate | 0.76 |
| PH adjuster, preservative | q.s. |

Example Formulation 148: Toothpaste

| Ingredient | % |
|---|---|
| Aqua | ad 100 |
| Glycerin | 33.0 |
| Hydrated Silica (Hydrated) | 24.0 |
| Glucolipid | 1.5 |
| Cellulose Gum | 0.8 |
| Aroma | 0.9 |
| Sodium Fluoride | 0.23 |
| Sodium Saccharin | 0.2 |
| Commiphora Myrrha Oil | 0.05 |
| Salvia Officinalis Oil | 0.05 |
| Mentha Piperita Oil | 0.2 |
| Chamomilla Recutita Flower Extract | 0.2 |
| Limonene | 0.1 |
| Titanium Dioxide | 0.3 |
| Dyes solution (1% FD&C Blue No. 1) | 0.05 |
| pH adjuster, preservative | q.s. |

Example Formulation 149: Toothpaste

| Ingredient | % |
|---|---|
| Glycerin | 27.0 |
| Hydrated Silica (Hydrated) | 21.0 |
| Sodium Hexametaphosphate | 13.0 |
| Aqua | ad 100 |
| PEG-6 | 5.0 |
| Flavor | 1.0 |
| Trisodium Phosphate | 1.0 |
| Sodium Lauryl Sulfate | 1.05 |
| Glucolipid | 0.35 |
| Chondrus Crispus | 0.7 |
| Cocamidopropyl Betaine | 0.1 |
| Sodium Saccharin | 0.2 |
| Polyethylene Glycol | 0.5 |
| Xanthan Gum | 0.7 |
| Sucralose | 0.5 |
| Mica | 0.3 |
| Titanium Dioxide | 0.5 |
| Sodium Fluoride | 0.32 |
| Dyes, pH adjuster, preservative | q.s. |

Example Formulation 150: Toothpaste

| Ingredient | % |
|---|---|
| Aqua | ad 100 |
| Sorbitol | 29.0 |
| Hydrated Silica (Hydrated) | 22.0 |
| Disodium Pyrophosphate | 5.0 |
| Glucolipid | 1.0 |
| Glycolipids | 1.0 |
| Cellulose Gum | 1.0 |
| Aroma | 0.9 |
| Sodium Bicarbonate | 0.8 |
| Carbomer | 0.8 |
| Sodium Fluoride | 0.32 |
| Sodium Saccharin | 0.1 |
| Xanthan Gum | 0.5 |
| Titanium Dioxide | 0.5 |
| Limonene | 0.2 |
| Dyes, pH adjuster, preservative | q.s. |

Example Formulation 151: Toothpaste

| Ingredient | % |
|---|---|
| Aqua | ad 100 |
| Hydrated Silica (Hydrated) | 21.0 |
| Sorbitol | 19.0 |
| Glycerin | 15.0 |
| Propylene Glycol | 5.0 |
| Tetrapotassium Pyrophosphate | 5.0 |
| Pentasodium Triphosphate | 5.0 |
| Sodium C14-16 Olefin Sulfonate | 0.5 |
| Glycolipids | 0.5 |
| Sophorolipid | 0.5 |
| Glucolipid | 0.5 |
| Disodium Pyrophosphate | 0.7 |
| Aroma | 0.3 |
| Titanium Dioxide | 0.4 |

-continued

| Ingredient | % |
|---|---|
| Xanthan Gum | 0.7 |
| Sodium Fluoride | 0.32 |
| Sodium Saccharin | 0.15 |
| Allantoin | 0.2 |
| Chamomilla Recutita Flower Extract | 0.1 |
| Salvia Officinalis Leaf Extract | 0.2 |
| Zinc Chloride | 0.3 |
| Dyes solution (1% FD&C Blue No. 1) | 0.05 |
| pH adjuster, preservative | q.s. |

Example Formulation 152: Toothpaste

| Ingredient | % |
|---|---|
| Aqua | ad 100 |
| Hydrated Silica (Hydrated) | 21.0 |
| Xylitol | 10.0 |
| Sorbitol | 10.0 |
| Glucolipid | 1.5 |
| Betaine | 0.5 |
| Aloe Barbadensis Leaf Juice Powder | 0.3 |
| Xanthan Gum | 0.5 |
| Zinc Gluconate | 0.5 |
| Sodium Coco-sulfate | 0.5 |
| Mentha Spicata Crispa Herb Oil | 0.1 |
| Calendula Officinalis Flower Extract | 0.2 |
| Chamomilla Recutita Flower Extract | 0.2 |
| L-limonene | 0.1 |
| Mentha Arvensis Leaf Oil | 0.1 |
| Sodium Fluoride | 0.32 |
| Titanium Dioxide | 0.4 |
| PH adjuster, preservative | q.s. |

Example Formulation 153: Toothpaste

| Ingredient | % |
|---|---|
| Aqua | ad 100 |
| Hydroxyapatite | 20.0 |
| Propylene Glycol | 10.0 |
| Glycerin | 10.0 |
| Sorbitol | 10.0 |
| Tetrapotassium Pyrophosphate | 7.0 |
| Silica | 7.0 |
| Glucolipid | 1.0 |
| Aroma | 1.0 |
| Cellulose Gum | 1.0 |
| Sodium C14-16 Olefin Sulfonate | 1.0 |
| Sodium Fluoride | 0.32 |
| Sodium Cocoyl Isethionate | 0.5 |
| Sodium Saccharin | 0.15 |
| Limonene | 0.2 |
| Titanium Dioxide | 0.4 |
| Dyes, pH adjuster, preservative | q.s. |

Example Formulation 154: Toothpaste

| Ingredient | % |
|---|---|
| Aqua | ad 100 |
| Hydrogenated Starch Hydrolysate (Hydrogenated, Hydrolysed) | 20.0 |
| Hydrated Silica (Hydrated), | 15.0 |
| Glycerin | 15.0 |
| Alumina | 10.0 |
| Sodium Lauryl Sulfate | 1.05 |
| PEG-12 | 1.0 |
| Glucolipid | 0.75 |
| Perlite | 0.5 |
| Pentapotassium Triphosphate | 0.8 |
| Pentasodium Triphosphate | 0.8 |

-continued

| Ingredient | % |
|---|---|
| Sodium Monofluorophosphate | 0.76 |
| Cellulose Gum | 0.9 |
| Sodium Saccharin | 0.2 |
| Cocamidopropyl Betaine | 0.35 |
| Aroma | 1.0 |
| Limonene | 0.1 |
| Dyes solution (1% FD&C Blue No. 1) | 0.05 |
| Titanium Dioxide | 0.3 |
| pH adjuster, preservative | q.s. |

Example Formulation 155: Toothpaste

| Ingredient | % |
|---|---|
| Dicalcium Phosphate Dihydrate (Dihydrate) | 25.0 |
| Aqua | ad 100 |
| Sorbitol | 20.0 |
| Glycerin | 20.0 |
| Methyl Salicylate | 1.0 |
| Sodium Lauryl Sulfate | 0.9 |
| Glucolipid | 0.9 |
| Titanium Dioxide | 0.5 |
| Chondrus Crispus | 0.8 |
| Cellulose Gum | 0.5 |
| Sodium Silicate | 0.3 |
| Hydrated Silica (Hydrated) | 1.0 |
| Thymol | 0.1 |
| Sodium Saccharin | 0.2 |
| Sodium Hydroxide | 0.5 |
| Menthol | 0.3 |
| Dyes solution (1% FD&C Blue No. 1) | 0.02 |
| pH adjuster, preservative | q.s. |

Example Formulation 156: Toothpaste

| Ingredient | % |
|---|---|
| Aqua | ad 100 |
| Hydrated Silica (Hydrated) | 21.0 |
| Sorbitol | 21.0 |
| Glycerin | 18.0 |
| PEG-6 | 5.0 |
| Glucolipid | 1.5 |
| Xanthan Gum | 0.8 |
| Flavor | 0.7 |
| Titanium Dioxide | 0.5 |
| Sodium Citrate | 0.4 |
| Sodium Fluoride | 0.32 |
| Zinc Chloride | 0.5 |
| Sodium Saccharin | 0.2 |
| Chondrus Crispus | 0.7 |
| Limonene | 0.1 |
| Dyes solution (1% FD&C Blue No. 1) | 0.04 |
| pH adjuster, preservative | q.s. |

Example Formulation 157: Toothpaste

| Ingredient | % |
|---|---|
| Aqua | ad 100 |
| Sorbitol | 36.0 |
| Hydrated Silica (Hydrated), | 18.0 |
| Glycerin | 18.0 |
| Potassium Nitrate | 1.0 |
| Aroma | 1.0 |
| Cocamidopropyl Betaine | 1.0 |
| Glucolipid | 1.0 |
| Xanthan Gum | 0.7 |
| Sodium Saccharin | 0.2 |
| Sodium Fluoride | 0.32 |

-continued

| Ingredient | % |
|---|---|
| Mica | 0.4 |
| Titanium Dioxide | 0.4 |
| Sodium Hydroxide | 0.5 |
| Limonene | 0.1 |
| Eugenol | 0.1 |
| Dyes, pH adjuster, preservative | q.s. |

Example Formulation 158: Toothpaste

| Ingredient | % |
|---|---|
| Glycerin | 33.0 |
| PEG-8 | 5.0 |
| Hydrated Silica (Hydrated), | 5.0 |
| Calcium Sodium Phosphosilicate | 3.0 |
| Cocamidopropyl Betaine | 1.0 |
| Glucolipid | 1.0 |
| Sodium Methyl Cocoyl Taurate | 0.3 |
| Aroma | 0.8 |
| Titanium Dioxide | 0.5 |
| Carbomer | 0.5 |
| Sodium Saccharin | 0.2 |
| Sodium Fluoride | 0.32 |
| Limonene | 0.2 |
| Dyes, pH adjuster, preservative | q.s. |

Example Formulation 159: Toothpaste

| Ingredient | % |
|---|---|
| Aqua | ad 100 |
| Sorbitol | 63.0 |
| Hydrated Silica (Hydrated) | 14.0 |
| Silica | 7.0 |
| Glucolipid | 1.0 |
| Titanium Dioxide | 0.6 |
| Maris Sal | 0.5 |
| Sophorolipid | 0.5 |
| Sodium Cocoyl Glutamate | 0.5 |
| Di sodium Cocoyl Glutamate | 0.5 |
| Xanthan Gum | 0.7 |
| Sodium Fluoride | 0.32 |
| Echinacea Purpurea Extract (Extract) | 0.1 |
| Arnica Montana Flower Extract | 0.1 |
| Mentha Piperita Leaf Water | 0.1 |
| Myrtus Communis Leaf Water | 0.1 |
| Glycerin | 1.0 |
| Menthol | 0.2 |
| Aroma | 1.0 |
| L-limonene | 0.2 |
| Dyes, pH adjuster, preservative | q.s. |

Example Formulation 160: Toothpaste

| Ingredient | % |
|---|---|
| Sorbitol | 33.0 |
| Aqua | ad 100 |
| Hydrated Silica (Hydrated) | 18.0 |
| Glycerin | 15.0 |
| PEG-32 | 4.0 |
| Sodium Lauryl Sulfate | 1.5 |
| Cellulose Gum | 1.0 |
| Glucolipid | 1.0 |
| Sodium Saccharin | 0.3 |
| Eucalyptol | 0.2 |
| Methyl Salicylate | 0.5 |
| Thymol | 0.1 |
| Phosphoric Acid | 0.3 |
| Menthol | 0.4 |

-continued

| Ingredient | % |
|---|---|
| Zinc Citrate | 0.5 |
| Sodium Phosphate | 0.2 |
| Xanthan Gum | 0.5 |
| Benzoic Acid | 0.2 |
| Sodium Monofluorophosphate | 0.76 |
| Flavor | 1.0 |
| Dyes solution (1% FD&C Blue No. 1) | 0.05 |
| pH adjuster, preservative | q.s. |

Example Formulation 161: Toothpaste

| Ingredient | % |
|---|---|
| Hydrogenated Starch Hydrolysate (Hydrogenated, Hydrolysed) | 30.0 |
| Aqua | ad 100 |
| Hydrated Silica (Hydrated) | 22.0 |
| PEG-32 | 4.0 |
| Glucolipid | 1.0 |
| Aroma | 1.0 |
| Cellulose Gum | 1.0 |
| Sodium Fluoride | 0.32 |
| Sodium Saccharin | 0.25 |
| PVM/MA Copolymer | 0.7 |
| Trisodium Phosphate | 0.8 |
| Calcium Aluminum Borosilicate | 0.4 |
| Glycerin | 0.9 |
| Lecithin | 0.2 |
| Tin Oxide | 0.2 |
| Limonene | 0.1 |
| Dyes solution (1% FD&C Blue No. 1) | 0.04 |
| Titanium Dioxide | 0.3 |
| pH adjuster, preservative | q.s. |

Example Formulation 162: Toothpaste

| Ingredient | % |
|---|---|
| Aqua | ad 100 |
| Sorbitol | 50.0 |
| Hydrated Silica (Hydrated), | 14.0 |
| Silica Dimethyl Silylate | 3.5 |
| Hydroxyethylcellulose | 3.5 |
| Glucolipid | 1.05 |
| PEG-40 Hydrogenated Castor Oil (Hydrogenated) | 0.8 |
| Aroma | 0.9 |
| Sodium Gluconate | 0.4 |
| Limonene | 0.1 |
| PEG-3 tallow aminopropyl amine | 0.5 |
| Olaflur | 0.06 |
| Stannous Fluoride | 0.4 |
| Sodium Saccharin | 0.2 |
| Potassium Hydroxide | 0.4 |
| Hydrochloric Acid | 0.2 |
| Dyes solution (1% FD&C Blue No. 1) | 0.04 |
| pH adjuster, preservative | q.s. |

Example Formulation 163: Toothpaste

| Ingredient | % |
|---|---|
| Aqua | ad 100 |
| Sorbitol | 45.0 |
| Hydrated Silica (Hydrated) | 21.0 |
| Sodium Lauryl Sulfate | 1.5 |
| Glucolipid | xx |
| Cellulose Gum | 1.0 |
| Aroma | 1.0 |
| Zinc Citrate | 0.5 |
| Chondrus Crispus Powder (Powdered) | 0.8 |
| Sodium Saccharin | 0.2 |

-continued

| Ingredient | % |
| --- | --- |
| Sodium Fluoride | 0.1 |
| Titanium Dioxide | 0.5 |
| Hydroxyethylcellulose | 0.3 |
| Sodium Citrate | 0.2 |
| Stannous Fluoride | 0.4 |
| Dyes, pH adjuster, preservative | q.s. |

Example Formulation 164: Toothpaste

| Ingredient | % |
| --- | --- |
| Sodium Bicarbonate | 35.00 |
| PEG-8 | 5.0 |
| Hydrated Silica (Hydrated | 18.0 |
| Glycerin | 18.0 |
| Glucolipid | 1.0 |
| Sodium Lauryl Sulfate | 0.5 |
| Sodium Saccharin | 0.5 |
| Aroma | 0.9 |
| Dipotassium Phosphate | 0.8 |
| Sodium Carbonate | 0.5 |
| Sodium Fluoride | 0.32 |
| PEG/PPG-116/66 Copolymer | 0.8 |
| Calcium Peroxide | 0.5 |
| Calcium Hydroxide | 0.4 |
| Dyes solution (1% FD&C Blue No. 1) | 0.04 |
| Sodium Silicate | 0.5 |
| Limonene | 0.1 |
| Silica | 0.9 |
| Titanium Dioxide | 0.3 |
| Dyes, pH adjuster, preservative | q.s. |

Example Formulation 165: Toothpaste

| Ingredient | % |
| --- | --- |
| Glycerin | 33.0 |
| Hydrated Silica | 22.0 |
| Aqua | ad 100 |
| Sorbitol | 15.0 |
| Tetrapotassium Pyrophosphate | 3.5 |
| Glucolipid | 1.5 |
| Titanium Dioxide | 0.4 |
| Sodium Lauroyl Sarcosinate | 0.5 |
| Cellulose Gum | 0.8 |
| Lauryl Glucoside | 0.5 |
| PVP | 0.5 |
| Cocamidopropyl Betaine | 0.5 |
| Xanthan Gum | 0.5 |
| Stannous Fluoride | 0.4 |
| Dyes, pH adjuster, preservative | q.s. |

Example Formulation 166: Toothpaste

| Ingredient | % |
| --- | --- |
| Aqua | ad 100 |
| Hydrated Silica (Hydrated) | 20.0 |
| Sorbitol | 18.0 |
| Xylitol | 14.0 |
| Glucolipid | 1.2 |
| Propylene Glycol | 1.0 |
| Glycerin | 1.0 |
| Sodium C14-16 Olefin Sulfonate | 0.3 |
| Aroma | 1.0 |
| Xanthan Gum | 0.5 |
| Disodium Phosphate | 0.4 |
| Sodium Fluoride | 0.32 |
| Zinc Chloride | 0.5 |
| Sodium Saccharin | 0.2 |

-continued

| Ingredient | % |
| --- | --- |
| Citric Acid | 0.2 |
| Titanium Dioxide | 0.4 |
| Dyes, pH adjuster, preservative | q.s. |

Example Formulation 167: Toothpaste

| Ingredient | % |
| --- | --- |
| Aqua | ad 100 |
| Hydrogenated Starch Hydrolysate (Hydrogenated, Hydrolysed) | 25.0 |
| Hydrated Silica (Hydrated) | 21.0 |
| Hydroxyapatite | 4.5 |
| PEG-32 | 4.5 |
| Glucolipid | 1.0 |
| Sodium Lauryl Sulfate | 0.5 |
| Aroma | 0.9 |
| Sodium Monofluorophosphate | 0.76 |
| Trisodium Phosphate | 0.5 |
| Cellulose Gum | 1.0 |
| Sodium Saccharin | 0.2 |
| Sodium Hydroxide | 0.3 |
| Limonene | 0.1 |
| Dyes solution (1% FD&C Blue No. 1) | 0.05 |
| Titanium Dioxide | 0.4 |
| pH adjuster, preservative | q.s. |

Example Formulation 168: Toothpaste

| Ingredient | % |
| --- | --- |
| Glycerin | 32.0 |
| Hydrated Silica (Hydrated) | 21.0 |
| Aqua | ad 100 |
| Sodium Bicarbonate | 30.0 |
| PEG-12 | 3.0 |
| Glucolipid | 1.5 |
| Sodium Lauryl Sulfate | 1.0 |
| Flavor | 1.0 |
| Sodium Hydroxide | 1.0 |
| Cellulose Gum | 1.0 |
| Chondrus Crispus | 0.7 |
| Sodium Saccharin | 0.15 |
| Calcium Peroxide | 0.5 |
| Titanium Dioxide | 0.5 |
| Sodium Monofluorophosphate | 0.76 |
| Dyes, pH adjuster, preservative | q.s. |

Example Formulation 169: Toothpaste

| Ingredient | % |
| --- | --- |
| Aqua | ad 100 |
| Sorbitol | 63.0 |
| Hydrated Silica (Hydrated) | 22.0 |
| Propylene Glycol | 1.5 |
| Cellulose Gum | 1.5 |
| Glucolipid | 1.0 |
| Sodium C 14-16 Olefin Sulfonate | 0.5 |
| Aroma | 0.8 |
| Calcium Glycerophosphate | 0.4 |
| Sodium Fluoride | 0.11 |
| Sodium Saccharin | 0.4 |
| Cocamidopropyl Betaine | 0.5 |
| Citral | 0.1 |
| Geraniol | 0.1 |
| Limonene | 0.1 |
| Linalool | 0.1 |
| Titanium Dioxide | 0.2 |
| Dyes, pH adjuster, preservative | q.s. |

Example Formulation 170: Toothpaste

| Ingredient | % |
|---|---|
| Aqua | ad 100 |
| Calcium Carbonate | 30.0 |
| Silica | 7.0 |
| Glycerin | 5.0 |
| Hydrated Silica | 2.5 |
| Glucolipid | 1.5 |
| Aroma | 1.0 |
| Chondrus Crispus Powder | 0.5 |
| Cellulose Gum | 0.5 |
| Chlorhexidine Gluconate | 0.1 |
| Limonene | 0.15 |
| Sodium Saccharin | 0.15 |
| Titanium Dioxide | 0.1 |
| Sodium Fluoride | 0.32 |
| Dyes, pH adjuster, preservative | q.s. |

Example Formulation 171: Toothpaste

| Ingredient | % |
|---|---|
| Aqua | ad 100 |
| Hydrogenated Starch Hydrolysate | 20.0 |
| Hydrated Silica | 15.0 |
| PEG-32 | 4.0 |
| Glycolipids | 1.5 |
| Glucolipid | 1.0 |
| Propylene Glycol | 0.9 |
| Aroma | 0.9 |
| Sodium Lauryl Sulfat | 0.5 |
| Hydroxyethylcellulose | 0.5 |
| Olaflur | 0.13 |
| Titanium Dioxide | 0.1 |
| Sodium Fluoride | 0.1 |
| Sodium Saccharin | 0.2 |
| Chamomilla Recutita Flower Extract | 0.2 |
| Chlorhexidine Digluconate | 0.1 |
| Limonene | 0.1 |
| Citral | 0.1 |
| Dyes, pH adjuster, preservative | q.s. |

Example Formulation 172: Toothpaste

| Ingredient | % |
|---|---|
| Aqua | ad 100 |
| Sorbitol | 20.0 |
| Hydrated Silica | 15.0 |
| Silica | 2.0 |
| Glucolipid | 1.0 |
| Cocamidopropyl Betaine | 0.75 |
| Titanium Dioxide | 0.15 |
| Flavor | 0.8 |
| Linalool | 0.2 |
| Sodium Monofluorophosphate | 0.76 |
| Sodium Fluoride | 0.1 |
| Sodium Saccharin | 0.25 |
| Cellulose Gum | 0.5 |
| Limonene | 0.1 |
| Chlorhexidine Digluconate | 0.12 |
| Dyes, pH adjuster, preservative | q.s. |

Example Formulation 173: Toothpaste

| Ingredient | % |
|---|---|
| Aqua | ad 100 |
| Hydrated Silica | 15.0 |
| Glycerin | 15.0 |
| Potassium Nitrate | 5.0 |
| Sorbitol | 4.5 |
| Sodium Cocoamphoacetate | 0.5 |
| Glucolipid | 0.5 |
| PEG-40 Hydrogenated Castor Oil | 0.5 |
| Carboxymethyl Cellulose | 0.5 |
| Titanium Dioxide | 0.1 |
| Sodium Fluoride | 0.32 |
| Sodium Saccharin | 0.2 |
| Aroma | 0.2 |
| Chlorhexidine Digluconate | 0.12 |
| Dyes, pH adjuster, preservative | q.s. |

Example Formulation 174: Toothpaste for Kids

| Ingredient | % |
|---|---|
| Aqua | ad 100 |
| Sorbitol | 28.0 |
| Hydrated Silica (Hydrated) | 18.0 |
| Hydroxyethylcellulose | 1.5 |
| Titanium Dioxide | 0.5 |
| Cocamidopropyl Betaine | 0.5 |
| Glucolipid | 0.5 |
| Olaflur | 0.07 |
| Aroma | 0.8 |
| Limonene | 0.1 |
| Sodium Saccharin | 0.2 |
| Hydrochloric Acid | 0.7 |
| Dyes, pH adjuster, preservative | q.s. |

Example Formulation 175: Toothpaste for Children

| Ingredient | % |
|---|---|
| Sorbitol | 33.0 |
| Aqua | ad 100 |
| Hydrated Silica (Hydrated) | 22.0 |
| Glucolipid | 1.0 |
| Sodium Cl4-16 Olefin Sulfonate | 1.0 |
| Aroma | 0.8 |
| Cellulose Gum | 0.8 |
| Calcium Glycerophosphate | 0.5 |
| Olaflur | 0.07 |
| Sodium Fluoride | 0.1 |
| Propylene Glycol | 0.5 |
| Sodium Saccharin | 0.2 |
| Cocamidopropyl Betaine | 0.35 |
| Mica | 0.5 |
| Citral | 0.1 |
| Limonene | 0.1 |
| Linalool | 0.1 |
| Titanium Dioxide | 0.4 |
| Dyes solution (1% FD&C Blue No. 1) | 0.05 |
| Olaflur | 0.07 |
| pH adjuster, preservative | q.s. |

Example Formulation 176: Baby Toothpaste

| Ingredient | % |
|---|---|
| Aqua | ad 100 |
| Hydrogenated Starch Hydrolysate (Hydrogenated, Hydrolysed) | 14.0 |
| Hydrated Silica (Hydrated) | 14.0 |
| PEG-32 | 3.5 |
| Silica | 7.0 |
| Glucolipid | 1.5 |
| Cellulose Gum | 1.0 |
| Aroma | 1.0 |
| Propylene Glycol | 0.7 |
| PEG-40 Hydrogenated Castor Oil (Hydrogenated), | 0.8 |

-continued

| Ingredient | % |
|---|---|
| Olaflur | 0.06 |
| Sodium Chloride | 0.2 |
| Sodium Saccharin | 0.15 |
| Tocopheryl Acetate | 0.1 |
| Glycerin | 1.0 |
| Retinyl Palmitate | 0.1 |
| Dyes solution (1% FD&C Blue No. 1) | 0.02 |
| pH adjuster, preservative | q.s. |

Example Formulation 177: Toothpaste for Children

| Ingredient | % |
|---|---|
| Aqua | ad 100 |
| Hydrated Silica (Hydrated) | 22.0 |
| Glycerin | 20.0 |
| Xylitol | 10.0 |
| Glucolipid | 1.5 |
| Propylene Glycol | 0.7 |
| Xanthan Gum | 0.5 |
| Titanium Dioxide | 0.5 |
| Flavor | 0.9 |
| Sodium Lauroyl Sarcosinate | 0.5 |
| Disodium EDTA | 0.3 |
| Sodium Monofluorophosphate | 0.76 |
| Sodium Chloride | 0.2 |
| Dyes, pH adjuster, preservative | q.s. |

Example Formulation 178: Kids Toothpaste

| Ingredient | % |
|---|---|
| Aqua | ad 100 |
| Sorbitol | 40.0 |
| Hydrated Silica (Hydrated) | 17.0 |
| Glycerin | 26.0 |
| Glucolipid | 1.5 |
| Xanthan Gum | 1.0 |
| Steareth-30 | 1.0 |
| Chondrus Crispus | 1.0 |
| Aroma | 1.0 |
| Disodium Phosphate | 0.5 |
| Sodium Benzoate | 0.2 |
| Amyloglucosidase | 0.1 |
| Citric Acid | 0.3 |
| Zinc Gluconate | 0.5 |
| Glucose Oxidase | 0.1 |
| Sodium Fluoride | 0.22 |
| Sodium Saccharin | 0.15 |
| Potassium Thiocyanate | 0.1 |
| Lactoperoxidase | 0.1 |
| Titanium Dioxide | 0.3 |
| Dyes, pH adjuster, preservative | q.s. |

Example Formulation 179: 2 in 1 Toothpaste+Mouthwash

| Ingredient | % |
|---|---|
| Sorbitol | 38.0 |
| Aqua | ad 100 |
| Hydrated Silica (Hydrated) | 21.0 |
| Pentasodium Triphosphate | 5.0 |
| Sodium Lauryl Sulfate | 0.35 |
| Glucolipid | 1.05 |
| PEG-32 | 1.0 |
| Aroma | 1.0 |
| Alumina | 0.5 |
| Alcohols | 0.7 |
| Xanthan Gum | 0.8 |
| Sodium Fluoride | 0.23 |

-continued

| Ingredient | % |
|---|---|
| Sodium Saccharin | 0.2 |
| Disodium Phosphate | 0.5 |
| Cocamidopropyl Betaine | 0.35 |
| Zinc Sulfate | 0.5 |
| Trisodium Phosphate | 0.3 |
| Sodium Chloride | 0.4 |
| Sodium Sulfate | 0.2 |
| Limonene | 0.1 |
| Titanium Dioxide | 0.5 |
| Dyes, pH adjuster, preservative | q.s. |

Example Formulation 180: 2 in 1 Toothpaste+Mouthwash

| Ingredient | % |
|---|---|
| Sorbitol | 29.0 |
| Aqua | ad 100 |
| Hydrated Silica | 15.0 |
| PEG-32 | 3.0 |
| Sodium Lauryl Sulfate | 0.5 |
| Glucolipid | 0.5 |
| Glycolipids | 0.5 |
| Aroma | 0.9 |
| Alcohols | 0.7 |
| Xanthan Gum | 0.5 |
| PEG-30 Glyceryl Stearate | 0.5 |
| Sodium Fluoride | 0.05 |
| Sodium Saccharin | 0.7 |
| Disodium Phosphate | 0.3 |
| Cocamidopropyl Betaine | 0.5 |
| Zinc Sulfate | 0.3 |
| Trisodium Phosphate | 0.5 |
| Sodium Chloride | 0.1 |
| Sodium Sulfate | 0.2 |
| Limonene | 0.02 |
| Dyes, pH adjuster, Preservative | q.s. |

Mouthwash

Example Formulation 181: Mouthrinse without Alcohol

| Ingredient | % |
|---|---|
| Aqua | ad 100 |
| Glycerin | 11.0 |
| Propylene Glycol | 7.0 |
| Glucolipid | 1.0 |
| Poloxamer 407 | 0.75 |
| Aroma | 0.9 |
| Cetylpyridinium Chloride | 0.04 |
| Sodium Fluoride | 0.05 |
| Sodium Saccharin | 0.07 |
| Menthol | 0.1 |
| Dyes, pH adjuster, Preservative | q.s. |

Example Formulation 182: Mouthrinse without Alcohol

| Ingredient | % |
|---|---|
| Aqua | ad 100 |
| Sorbitol | 15.0 |
| Glycerin | 7.5 |
| Glucolipid | 1.0 |
| Xylitol | 1.0 |
| Cellulose Gum | 0.5 |
| Zinc PCA | 0.5 |
| Zinc Hydroxyapatite | 0.05 |
| Aroma | 0.9 |
| Silica | 0.05 |
| Ricinus Communis Seed Oil | 0.1 |
| Ammonium Acryloyldimethyltaurate/VP Copolymer | 0.05 |

-continued

| Ingredient | % |
|---|---|
| Mentha Arvensis Leaf Oil | 0.01 |
| Sodium Myristoyl Sarcosinate | 0.2 |
| Sodium Methyl Cocoyl Taurate | 0.2 |
| Sodium Saccharin | 0.5 |
| Sodium Fluoride | 0.05 |
| Limonene | 0.1 |
| Dyes, pH adjuster, Preservative | q.s. |

Example Formulation 183: Mouthrinse without Alcohol

| Ingredient | % |
|---|---|
| Aqua | ad 100 |
| Sorbitol | 20.0 |
| PEG-40 | 0.5 |
| Glucolipid | 0.5 |
| Flavor | 0.05 |
| Xanthan Gum | 0.1 |
| Zinc Sulfate | 0.15 |
| Sodium Saccharin | 0.05 |
| Sodium Fluoride | 0.05 |
| Gellan Gum | 0.2 |
| Calcium Aluminum Borosilicate | 0.1 |
| Silica | 0.05 |
| Titanium Dioxide | 0.05 |
| Tin Oxide | 0.07 |
| Eugenol | 0.15 |
| Limonene | 0.05 |
| Linalool | 0.05 |
| Dyes, pH adjuster, Preservative | q.s. |

Example Formulation 184: Mouthrinse without Alcohol

| Ingredient | % |
|---|---|
| Aqua | ad 100 |
| Glycerin | 7.5 |
| Glucolipid | 0.5 |
| Glycolipids | 0.5 |
| Flavor | 0.3 |
| Cetylpyridinium Chloride | 0.04 |
| Sodium Saccharin | 0.05 |
| Sucralose | 0.05 |
| Sodium Fluoride | 0.02 |
| Disodium Phosphate | 0.25 |
| Dyes, pH adjuster, Preservative | q.s. |

Example Formulation 185: Mouthrinse

| Ingredient | % |
|---|---|
| Aqua | ad 100 |
| Glycerin | 10.0 |
| Sorbitol | 10.0 |
| Cocamidopropyl Betaine | 1.0 |
| Glucolipid | 0.5 |
| Potassium Chloride | 0.1 |
| Propylene Glycol | 0.5 |
| Aroma | 0.25 |
| Sodium Fluoride | 0.02 |
| Olaflur | 0.16 |
| Potassium Acesulfame | 0.1 |
| Sodium Chloride | 0.1 |
| Limonene | 0.03 |
| Sodium Sulfate | 0.05 |
| Dyes, pH adjuster, Preservative | q.s. |

Example Formulation 43: Mouthrinse without Alcohol

| Ingredient | % |
|---|---|
| Aqua | ad 100 |
| Sorbitol | 15.0 |
| Glucolipid | 1.0 |
| Aloe Barbadensis Leaf Extract | 0.15 |
| Calendula Officinalis Flower Extract | 0.2 |
| Chamomilla Recutita Flower Extract | 0.2 |
| Sodium Fluoride | 0.02 |
| Calcium Glycerophosphate | 0.05 |
| Zinc Gluconate | 0.8 |
| Mentha Spicata Crispa Herb Oil | 0.05 |
| Mentha Arvensis Leaf Oil | 0.05 |
| Menthol | 0.04 |
| Dyes, pH adjuster, Preservative | q.s. |

Example Formulation 186: Mouthrinse without Alcohol

| Ingredient | % |
|---|---|
| Aqua | ad 100 |
| Glycerin | 15.0 |
| Sodium Gluconate | 1.5 |
| Glucolipid | 0.5 |
| PEG-40 Hydrogenated Castor Oil | 0.5 |
| Olaflur | 0.16 |
| Aroma | 0.25 |
| Stannous Chloride | 0.05 |
| Sodium Fluoride | 0.02 |
| Cocamidopropyl Betaine | 0.35 |
| Sodium Saccharin | 0.07 |
| Dyes, pH adjuster, Preservative | q.s. |

Example Formulation 187: Mouthrinse without Alcohol

| Ingredient | % |
|---|---|
| Aqua | ad 100 |
| Glycerin | 10.0 |
| Sorbitol | 8.0 |
| Glucolipid | 1.0 |
| Sophorolipid | 0.5 |
| Tetrasodium Pyrophosphate | 0.25 |
| Aroma | 0.04 |
| Limonene | 0.1 |
| Sodium Fluoride | 0.02 |
| Sodium Saccharin | 0.08 |
| Dyes, pH adjuster, Preservative | q.s. |

Example Formulation 188: Mouthrinse without Alcohol

| Ingredient | % |
|---|---|
| Aqua | ad 100 |
| Glycerin | 7.5 |
| PEG-60 Hydrogenated Castor Oil | 1.0 |
| Glucolipid | 0.5 |
| Sodium Citrate | 0.45 |
| Aroma | 0.3 |
| Zinc Chloride | 0.15 |
| Cetylpyridinium Chloride | 0.05 |
| Sodium Saccharin | 0.08 |
| Sodium Fluoride | 0.02 |
| Dyes, pH adjuster, Preservative | q.s. |

Example Formulation 189: Mouthrinse without Alcohol

| Ingredient | % |
|---|---|
| Aqua | ad 100 |
| Glycerin | 11.0 |
| Glucolipid | 2.0 |
| Flavor | 1.0 |
| Cetylpyridinium Chloride | 0.5 |
| Poloxamer 407 | 0.1 |
| Sodium Saccharin | 0.1 |
| Sodium Fluoride | 0.02 |
| Sucralose | 0.05 |
| Mentha Viridis Leaf Oil | 0.1 |
| Dyes, pH adjuster, Preservative | q.s. |

Example Formulation 190: Mouthrinse without Alcohol

| Ingredient | % |
|---|---|
| Aqua | ad 100 |
| Glycerin | 12.0 |
| Sorbitol | 8.0 |
| Potassium Nitrate | 0.15 |
| PEG-60 Hydrogenated Castor Oil | 0.5 |
| Glucolipid | 0.25 |
| Poloxamer 407 | 0.25 |
| Aroma | 0.2 |
| Disodium Phosphate, Sodium Phosphate | 0.25 |
| Sodium Fluoride | 0.05 |
| Sodium Saccharin | 0.08 |
| Dyes, pH adjuster, Preservative | q.s. |

Example Formulation 191: Mouthrinse without Alcohol

| Ingredient | % |
|---|---|
| Aqua | ad 100 |
| Sorbitol | 10.0 |
| PEG-40 Hydrogenated Castor Oil | 1.0 |
| Potassium Citrate | 1.0 |
| Glucolipid | 0.25 |
| Glycerin | 0.9 |
| Aroma | 0.4 |
| Zinc Sulfate | 0.15 |
| Sodium Saccharin | 0.1 |
| Propylene Glycol | 0.3 |
| Citrus Limon Juice | 0.05 |
| Aloe Barbadensis Leaf Extract | 0.1 |
| Limonene | 0.05 |
| Sodium Fluoride | 0.02 |
| Dyes, pH adjuster, Preservative | q.s. |

Example Formulation 192: Mouthrinse without Alcohol

| Ingredient | % |
|---|---|
| Aqua | ad 100 |
| Glycerin | 12.0 |
| Glucolipid | 1.2 |
| Gycolipids | 1.0 |
| Hydrogenated Starch Hydrolysate | 1.0 |
| Xylitol | 1.0 |
| Steareth-30 | 0.2 |
| Amyloglucosidase | 0.5 |
| Allantoin | 0.1 |
| Sophorolipid | 0.2 |
| Glucose Oxidase | 0.5 |
| Sodium Fluoride | 0.05 |
| Limonene | 0.1 |
| Dyes, pH adjuster, Preservative | q.s. |

Example Formulation 193: Mouthrinse

| Ingredient | % |
|---|---|
| Aqua | ad 100 |
| Glycerin | 11.0 |
| Propylene Glycol | 7.5 |
| Sorbitol | 7.5 |
| Tetrapotassium Pyrophosphate | 1.5 |
| Polysorbate 20 | 0.5 |
| Glucolipid | 0.5 |
| Tetrasodium Pyrophosphate | 0.75 |
| Zinc Citrate | 0.15 |
| PVM/MA Copolymer | 0.1 |
| Flavor | 0.2 |
| Sodium Fluoride | 0.05 |
| Sodium Saccharin | 0.07 |
| Dyes, pH adjuster, Preservative | q.s. |

Example Formulation 194: Mouthrinse

| Ingredient | % |
|---|---|
| Aqua | ad 100 |
| Glycerin | 11.0 |
| Alcohol | 7.5 |
| Sorbitol | 7.5 |
| Glucolipid | 1.0 |
| Poloxamer 407 | 0.5 |
| Sodium Phosphate, Disodium Phosphate | 0.15 |
| Flavor | 0.9 |
| Cetylpyridinium Chloride | 0.05 |
| Sodium Saccharin | 0.08 |
| Sodium Fluoride | 0.05 |
| Dyes, pH adjuster, Preservative | q.s. |

Example Formulation 195: Mouthrinse

| Ingredient | % |
|---|---|
| Aqua | ad 100 |
| Alcohols | 22.0 |
| Sorbitol | 10.0 |
| Flavor | 1.0 |
| Glucolipid | 1.0 |
| Sodium Saccharin | 0.09 |
| Eucalyptol | 0.1 |
| Thymol | 0.06 |
| Sucralose | 0.06 |
| Sodium Fluoride | 0.05 |
| Menthol | 0.04 |
| Dyes, pH adjuster, Preservative | q.s. |

Example Formulation 196: Mouthrinse

| Ingredient | % |
|---|---|
| Aqua | ad 100 |
| Glycerin | 12.0 |
| Xylitol | 7.0 |
| Disodium Phosphate | 1.5 |
| Glucolipid | 1.0 |
| Cocamidopropyl Betaine | 0.5 |
| Propylene Glycol | 0.5 |
| Stannous Fluoride | 0.09 |
| Aroma | 0.3 |
| Mentha Piperita Leaf Extract | 0.1 |
| Chamomilla Recutita Flower Extract | 0.2 |
| Salvia Officinalis Leaf Extract | 0.25 |
| Commiphora Myrrha Resin Extract | 0.15 |
| Sodium Saccharin | 0.1 |
| Citral | 0.05 |
| Limonene | 0.02 |

-continued

| Ingredient | % |
|---|---|
| Linalool | 0.02 |
| Dyes, pH adjuster, Preservative | q.s. |

Example Formulation 55: Mouthrinse

| Ingredient | % |
|---|---|
| Aqua | ad 100 |
| Glycerin | 11.0 |
| Sorbitol | 11.0 |
| Propylene Glycol | 3.0 |
| Disodium Pyrophosphate | 1.5 |
| PEG-40 Hydrogenated Castor Oil | 1.0 |
| Glucolipid | 0.5 |
| PVM/MA Copolymer | 0.5 |
| Tetrapotassium Pyrophosphate | 0.25 |
| Sodium Levulinate | 0.25 |
| Sodium Anisate | 0.25 |
| Olaflur | 0.16 |
| Aroma | 0.8 |
| Arginine | 0.8 |
| Sodium Saccharin | 0.07 |
| Sodium Fluoride | 0.02 |
| Dyes, pH adjuster, Preservative | q.s. |

Example Formulation 197: Mouthrinse

| Ingredient | % |
|---|---|
| Aqua | ad 100 |
| Alcohol Denat. | 33.0 |
| Glycerin | 10.0 |
| Sorbitol | 8.0 |
| PEG-40 Hydrogenated Castor Oil | 1.0 |
| Glucolipid | 1.0 |
| Glycolipids | 0.5 |
| Aroma | 0.6 |
| Menthol | 0.05 |
| Sodium Saccharin | 0.07 |
| Aluminum Lactate | 0.2 |
| Thymol | 0.06 |
| Curcuma Xanthorrhiza Root Extract | 0.05 |
| Sodium Fluoride | 0.02 |
| Dyes, pH adjuster, Preservative | q.s. |

Example Formulation 198: Mouthrinse

| Ingredient | % |
|---|---|
| Aqua | ad 100 |
| Sorbitol | 12.5 |
| Propylene Glycol | 3.5 |
| Glucolipid | 0.5 |
| Sodium Lauryl Sulfate | 0.5 |
| Poloxamer 407 | 0.5 |
| Flavor | 0.3 |
| Eucalyptol | 0.08 |
| Methyl Salicylate | 0.1 |
| Thymol | 0.05 |
| Stannous Fluoride | 0.09 |
| Menthol | 0.1 |
| Sodium Saccharin | 0.06 |
| Sucralose | 0.7 |
| Camellia Sinensis Leaf Extract | 0.05 |
| Dyes, pH adjuster, Preservative | q.s. |

Example Formulation 199: Mouthrinse

| Ingredient | % |
|---|---|
| Aqua | ad 100 |
| Glucolipid | 1.0 |
| Eucalyptol | 0.9 |
| Zinc Chloride | 0.25 |
| Methyl Salicylate | 0.05 |
| Thymol | 0.05 |
| Levomenthol | 0.07 |
| Stannous Fluoride | 0.09 |
| Dyes, pH adjuster, Preservative | q.s. |

Example Formulation 200: Mouthrinse

| Ingredient | % |
|---|---|
| Aqua | ad 100 |
| Alcohol Denat. | 15.0 |
| Sorbitol | 5.0 |
| Glycine | 1.0 |
| Glucolipid | 1.0 |
| Aroma | 0.2 |
| Zinc Sulfate | 0.2 |
| Sodium Fluoride | 0.02 |
| Sodium Saccharin | 0.07 |
| Dyes, pH adjuster, Preservative | q.s. |

Example Formulation 201: Mouthrinse

| Ingredient | % |
|---|---|
| Aqua | ad 100 |
| Sorbitol | 11.0 |
| Alcohol Denat. | 11.0 |
| Xylitol | 5.0 |
| PEG-40 Hydrogenated Castor Oil | 0.75 |
| Glucolipid | 0.5 |
| Isopropyl Alcohol | 0.5 |
| Menthol | 0.05 |
| Sodium Citrate | 0.15 |
| Mentha Piperita Herb Oil | 0.25 |
| Sodium Saccharin | 0.08 |
| Methyl Diisopropyl Propionamide | 0.05 |
| Thymol | 0.07 |
| Sophorolipid | 0.1 |
| Sodium Fluoride | 0.05 |
| O-cymen-5-ol | 0.05 |
| Cyclodextrin | 0.07 |
| Eugenia Caryophyllus Leaf Oil | 0.1 |
| Propylene Glycol | 0.25 |
| Butylene Glycol | 0.25 |
| Psidium Guajava Leaf Extract | 0.08 |
| Phyllanthus Emblica Fruit Extract | 0.08 |
| Echinacea Purpurea Root Extract | 0.08 |
| Salvia Officinalis Leaf Extract | 0.2 |
| Dyes, pH adjuster, Preservative | q.s. |

Example Formulation 202: Mouthrinse

| Ingredient | % |
|---|---|
| Aqua | ad 100 |
| Alcohols | 15.0 |
| Sorbitol | 7.0 |
| Sodium Lauroyl Sarcosinate | 1.0 |
| Glucolipid | 0.25 |
| PEG-40 Hydrogenated Castor Oil | 0.25 |
| Aroma | 0.4 |
| Cetylpyridinium Chloride | 0.04 |
| Sodium Citrate | 0.15 |
| Sodium Saccharin | 0.08 |

-continued

| Ingredient | % |
|---|---|
| Sodium Fluoride | 0.05 |
| Limonene | 0.05 |
| Dyes, pH adjuster, Preservative | q.s. |

Example Formulation 203: Mouthrinse

| Ingredient | % |
|---|---|
| Aqua | ad 100 |
| Alcohol denat. | 18.0 |
| Sorbitol | 8.0 |
| Aroma | 1.0 |
| Poloxamer 407 | 0.9 |
| Methyl salicylate | 0.2 |
| Sodium Saccharin | 0.2 |
| Sodium Fluoride | 0.05 |
| Glucolipid | 0.9 |
| Chlorhexidine Digluconate | 0.2 |
| PEG-40 Hydrogenated Castor Oil | 0.2 |
| Dyes, pH adjuster, Preservative | q.s. |

Example Formulation 204: Mouthrinse

| Ingredient | % |
|---|---|
| Aqua | ad 100 |
| Glycerin | 10.0 |
| Hydrogenated Starch Hydrolysate | 1.0 |
| PVP | 0.5 |
| Glucolipid | 0.5 |
| Aroma | 0.4 |
| Zinc Acetate | 0.2 |
| Sodium Fluoride | 0.32 |
| Potassium Acesulfame | 0.15 |
| Chlorhexidine Digluconate | 0.2 |
| Dyes, pH adjuster, Preservative | q.s. |

Example Formulation 205: Mouthrinse

| Ingredient | % |
|---|---|
| Aqua | ad 100 |
| Glycerin | 12.0 |
| Sorbitol | 7.0 |
| Glucolipid | 0.75 |
| PEG-40 Hydrogenated Castor Oil | 0.5 |
| Chlorhexidine Gluconate | 0.2 |
| Mentha Piperita Oil | 0.2 |
| Sodium Fluoride | 0.05 |
| Sodium Saccharin | 0.2 |
| Dyes, pH adjuster, Preservative | q.s. |

Example Formulation 206: Mouthrinse

| Ingredient | % |
|---|---|
| Aqua | ad 100 |
| Glycerin | 15.0 |
| Macrogolglycerol Hydroxystearate | 7.0 |
| Sorbitol | 7.0 |
| Glucolipid | 0.5 |
| Cocamidopropyl Betaine | 0.2 |
| Sodium Fluoride | 0.02 |
| Chlorhexidine Digluconate | 0.2 |
| Flavor | 0.5 |
| Dyes, pH adjuster, Preservative | q.s. |

Example Formulation 207: Mouthrinse Concentrate

| Ingredient | % |
|---|---|
| Propylene Glycol | 55.0 |
| Aqua | ad 100 |
| Aroma | 2.0 |
| Sodium Saccharin | 0.4 |
| Glucolipid | 0.75 |
| Polysorbate 20 | 0.25 |
| Commiphora Myrrha Oil | 2.0 |
| Salvia Officinalis Oil | 0.2 |
| Mentha Piperita Oil | 0.2 |
| Chamomilla Recutita Flower Extract | 0.2 |
| Limonene | 0.1 |
| Sodium Fluoride | 0.02 |
| Dyes, pH adjuster, Preservative | q.s. |

Example Formulation 208: Mouthrinse Concentrate

| Ingredient | % |
|---|---|
| Propylene Glycol | 45.0 |
| PEG-6 | 5.0 |
| Aqua | ad 100 |
| Glucolipid | 1.0 |
| Bisabolol | 0.2 |
| Zinc Chloride | 0.25 |
| Cetylpyridinium Chloride | 0.1 |
| Sodium Saccharin | 0.5 |
| Sodium Fluoride | 0.05 |
| Salvia Officinalis Oil | 2.5 |
| Eugenol | 0.2 |
| Limonene | 0.1 |
| Linalool | 0.1 |
| Citronellol | 0.1 |
| Dyes, pH adjuster, Preservative | q.s. |

Example Formulation 209: Mouthrinse Concentrate

| Ingredient | % |
|---|---|
| Alcohols | 55.0 |
| Aqua | ad 100 |
| Aroma | 1.5 |
| Glucolipid | 0.7 |
| Sodium C14-17 Alkyl Sulfonate | 0.7 |
| Mentha Arvensis Leaf Oil | 2.0 |
| Sodium Saccharin | 0.5 |
| Chamomilla Recutita Flower Extract | 0.5 |
| Commiphora Myrrha Resin Extract | 0.2 |
| Salvia Officinalis Leaf Extract | 0.2 |
| Sodium Fluoride | 0.02 |
| Limonene | 0.1 |
| Dyes, pH adjuster, Preservative | q.s. |

Example Formulation 210: Peroxide Mouthrinse

| Ingredient | % |
|---|---|
| Aqua | ad 100 |
| Glycerin | 11.0 |
| Alcohol | 5.0 |
| $H_2O_2$ 35% | 4.30 |
| Polyphosphate | 1.0 |
| Menthol | 0.05 |
| Coolant | 0.02 |
| Flavor | 0.15 |
| Calcium Chloride | 0.03 |
| Glucolipid | 0.50 |

-continued

| Ingredient | % |
| --- | --- |
| Sodium Saccharin | 0.1 |
| Sodium Fluoride | 0.22 |
| Dyes, pH adjuster, Preservative | q.s. |

Example Formulation 211: Fluoride Gel

| Ingredient | % |
| --- | --- |
| Aqua | ad 100 |
| Propylene Glycol | 30.0 |
| Hydroxyethylcellulose | 3.0 |
| Saccharin | 1.0 |
| Glucolipid | 0.5 |
| Pyrus Malus Fruit | 0.2 |
| Mentha Piperita Oil | 0.2 |
| Flavor | 0.5 |
| Aminofluoride Dectafluor | 0.29 |
| Olaflur | 3.03 |
| Sodium Fluoride | 2.21 |
| Dyes, pH adjuster, Preservative | q.s. |

Example Formulation 212: Fluoride Gel

| Ingredient | % |
| --- | --- |
| Aqua | ad 100 |
| Sorbitol | 15.00 |
| Silica | 5.0 |
| PEG 600 | 3.5 |
| Tetrapotassium Pyrophosphate | 1.5 |
| Xanthan Gum | 0.5 |
| Sodium Lauryl Sulfate | 0.75 |
| Glucolipid | 0.75 |
| Aroma | 0.9 |
| Methol | 0.05 |
| Anethol | 0.05 |
| Citronellol | 0.2 |
| Sodium Fluoride | 5.0 |
| Dyes, pH adjuster, Preservative | q.s. |

Example Formulation 213: Dental Floss

| Ingredient | % |
| --- | --- |
| PTFE | ad 100 |
| Aroma | 1.0 |
| Acacia Senegal Gum | 0.7 |
| Cera Alba | 0.7 |
| Potassium Acesulfame | 0.5 |
| Sodium Lauryl Sulfate | 0.25 |
| Glucolipid | 0.25 |
| Glycerin | 0.7 |
| Silica | 0.5 |
| Sodium Fluoride | 0.22 |

Example Formulation 214: Teeth Wipe

| Ingredient | % |
| --- | --- |
| Aqua | q.s. 100 |
| Alcohol Denat. | 30.00 |
| Glycerin | 20.00 |
| Stevia | 1.0 |
| Polysorbate 20 | 0.5 |
| Glucolipid | 0.5 |
| Aroma | 1.0 |
| Dyes, pH adjuster, Preservatives | q.s. |

Example Formulation 215: Chewing Gum

| Ingredient | % |
| --- | --- |
| Gum Base | ad 100 |
| Sorbit | 40.0 |
| Isomalt | 9.0 |
| Xylitol | 2.5 |
| Mannit D | 2.5 |
| Aspartame | 0.1 |
| Acesulfam K | 0.05 |
| Emulgum | 0.2 |
| Sorbitol | 12.00 |
| Glycerin | 1.0 |
| Glucolipid | 1.0 |
| Flavor | 1.0 |
| Sodium Fluoride | 0.05 |
| Dyes, pH adjuster, Preservative | q.s. |

Example Formulation 216: Mouthwash Tabs

| Ingredient | % |
| --- | --- |
| Dicalcium Phosphate Anhydrous | ad 100 |
| Sodium Bicarbonate | 35.0 |
| Silica | 7.0 |
| Citric Acid | 4.0 |
| Glucolipid | 3.0 |
| Sorbitol | 1.0 |
| Glycerin | 1.0 |
| *Stevia Rebaudiana* Extract (Stevia) | 0.2 |
| Xylitol | 0.5 |
| Aroma | 0.1 |
| Mentha Piperita Oil | 0.1 |
| Dyes, pH adjuster, Preservative | q.s. |

Example Formulation 217: Tooth Tab

| Ingredient | % |
| --- | --- |
| Dicalcium Phosphate Anhydrous | ad 100 |
| Potassium Bitartrate | 15.0 |
| Sorbitol | 15.0 |
| Glucolipid | 6.0 |
| Lauroyl Sarcosine | 0.8 |
| Kaolin | 0.5 |
| Sodium Saccharin | 0.5 |
| Aroma | 0.2 |
| Dyes, pH adjuster, Preservative | q.s. |

Example Formulation 218: Powder Toothpaste

| Ingredient | % |
| --- | --- |
| Calcium Carbonate | ad 100 |
| Sorbitol | 15.0 |
| Kaolin | 15.0 |
| Sodium Bicarbonate | 15.0 |
| Glucolipid | 1.5 |
| Aroma | 1.0 |
| Citrus Limon Peel Oil | 1.0 |
| *Stevia Rebaudiana* Extract | 0.5 |
| Xylitol | 0.5 |
| Citral | 0.1 |
| Geraniol | 0.1 |
| Limonene | 0.1 |
| Dyes, pH adjuster, Preservative | q.s. |

Further Example Formulations:

| | I | II | III | IV | V | VI | VII | VIII | IX | X |
|---|---|---|---|---|---|---|---|---|---|---|
| Aqua | | | | | ad 100% | | | | | |
| Glucolipid | 9.0% | 15.0% | 5.5% | 5.0% | 7.0% | 3.0% | 6.0% | 4.0% | 3.5% | 3.0% |
| Sodium Laureth Sulfate | — | — | — | 7.0% | — | — | — | 4.5% | — | — |
| Sodium Lauryl Sulfate | — | — | — | — | 5.0% | — | — | — | 3.5% | 1.0% |
| Cocamidopropyl Betaine | — | — | — | — | — | 6.0% | — | 3.0% | 2.0% | 4.5% |
| Sodium Cocoamphoacetate | — | — | — | — | — | — | 2.0% | — | 3.5% | — |
| Coco-Glucoside | — | — | — | — | — | — | 5.5% | 1.5% | — | — |
| Sodium Cocoyl Glutamate | — | — | — | — | — | — | 0.7% | — | — | — |
| Stearic Acid | — | — | — | — | — | — | — | 1.0% | — | 3.5% |
| Glyceryl Glucoside | — | 0.5% | — | — | 0.3% | — | 0.2% | — | — | — |
| Sucrose Cocoate | 0.5% | — | 1.0% | 1.0% | 1.0% | 0.5% | — | 1.0% | 1.0% | 1.0% |
| Glycerin | — | 1.0% | 0.5% | — | — | 0.3% | 1.5% | 1.0% | — | 1.0% |
| PEG-7 Glyceryl Cocoate | — | 0.7% | — | 0.5% | — | — | — | — | — | 0.5% |
| Trideceth-9 | — | — | — | 0.2% | — | — | — | 0.3% | — | — |
| Polyglyceryl-4 Caprate | — | — | 1.0% | — | 0.4% | — | 0.5% | — | — | — |
| Polyquaternium-10 | — | 0.2% | — | 0.1% | — | — | — | 0.2% | — | — |
| Hydroxypropyl Guar Hydroxypropyltrimonium Chloride | 0.2% | — | 0.3% | 0.2% | 0.2% | 0.2% | 0.3% | 0.1% | 0.2% | — |
| Silicone Quaternium-22 | — | — | — | 0.5% | — | — | — | 0.5% | — | — |
| Dimethicone | — | 0.5% | — | — | — | — | — | 1.0% | — | — |
| Amodimethicone | — | 0.1% | — | — | 1.0% | 0.3% | — | — | 0.5% | — |
| Argania Spinosa Oil | — | — | 0.2% | 0.1% | — | 0.1% | 0.2% | — | — | — |
| Glycol Distearate | 0.5% | 0.5% | — | — | 0.5% | — | 0.3% | 0.5% | 0.5% | 0.5% |
| Acrylates/C10-30 Alkyl Acrylate Crosspolymer | 1.0% | — | — | — | 0.5% | — | — | — | 0.5% | — |
| Sodium Hydroxide, 25% | 1.5% | — | — | — | 0.8% | — | — | — | 0.7% | — |
| Isostearamide MIPA; Glyceryl Laurate | — | — | — | — | — | 2.5% | — | — | 1.0% | 0.5% |
| Cocamide DEA | — | — | — | 1.0% | 0.5% | — | — | — | — | — |
| Sodium Chloride | 0.1% | 1.2% | — | 0.5% | — | 1.5% | — | 2.0% | — | 1.2% |
| PEG-120 Methyl Glucose Dioleate | — | 3.5% | — | 0.2% | — | — | — | 0.6% | — | — |
| Xanthan Gum | — | — | 1.2% | — | — | 0.2% | 1.5% | — | — | — |
| Cellulose | — | — | — | 0.1% | — | 0.1% | 0.1% | — | 0.1% | — |
| Zinc Pyrithione | — | 0.1% | — | 1.1% | — | — | — | 0.5% | — | — |
| Benzophenone-4 | — | 0.1% | — | 0.2% | — | — | — | 0.2% | 0.1% | — |
| Tetrasodium EDTA | 0.1% | 0.1% | — | 0.1% | — | — | — | 0.1% | 0.1% | — |
| Caffeine | — | — | 0.1% | — | — | — | — | 0.1% | 0.1% | — |
| Hydrolyzed Keratin | — | — | 0.1% | 0.1% | — | 0.1% | 0.2% | — | 0.1% | — |
| Panthenol | 0.1% | 0.1% | 0.1% | 0.1% | 0.1% | 0.1% | — | 0.1% | 0.1% | 0.1% |
| Citric Acid | | | | | ad pH | | | | | |
| Parfums, Dyes, Preservatives | | | | | q.s. | | | | | |

| | XI | XII | XIII | XIV | XV | XVI | XVII | XVIII | XIX | XX |
|---|---|---|---|---|---|---|---|---|---|---|
| Aqua | | | | | ad 100% | | | | | |
| Glucolipid | 10.0% | 7.0% | 5.0% | 4.0% | 7.0% | 2.5% | 6.0% | 4.0% | 2.0% | 1.0% |
| Sodium Laureth Sulfate | — | — | 8.0% | — | — | — | — | 3.5% | — | — |
| Coco-Betaine | — | — | — | 5.5% | 5.0% | — | — | 3.0% | — | — |
| Cocamidopropyl Betaine | — | — | — | — | — | 6.0% | — | — | 3.0% | 4.0% |
| Sodium Cocoamphoacetate | — | — | — | — | 2.0% | — | — | — | — | — |
| Coco Glucoside | — | — | — | — | 2.0% | — | 4.0% | 1.5% | 6.0% | — |
| Glycolipids | — | — | — | — | — | — | 2.5% | 0.5% | 2.5% | 0.3% |
| Sophorolipid | 0.5% | | | | | 1.0% | | | | |
| Stearic Acid | — | 8.0% | — | — | — | — | — | — | — | 4.5% |
| Sodium Cocoyl Glycinate | — | — | — | — | — | 3.0% | 0.5% | — | — | 0.3% |
| Sodium Lauroyl Methyl Isethionate | — | — | — | — | — | 1.0% | — | 1.0% | 2.0% | 0.5% |
| Sucrose Cocoate | 0.5% | 1.1% | — | 1.0% | 1.0% | — | — | 0.3% | 1.0% | 0.3% |
| Glycerin | 1.5% | 0.3% | 0.5% | — | 0.3% | 0.5% | 1.0% | 0.5% | — | 1.0% |
| PEG-7 Glyceryl Cocoate | — | — | 0.5% | — | — | 0.8% | — | 0.5% | — | 0.5% |
| PEG-40 Hydrogenated Castor Oil | — | — | 0.5% | — | — | 1.5% | — | 0.3% | — | — |
| Polyglyceryl-4 Caprate | 0.5% | — | — | — | 0.4% | — | 0.5% | — | 1.1% | — |
| Polyquaternium-11 | — | 0.2% | — | — | 0.1% | 0.3% | — | 0.2% | — | — |
| Guar Hydroxypropyltrimonium Chloride | 0.3% | — | 0.3% | 0.2% | 0.2% | — | 0.3% | 0.1% | 0.4% | 0.2% |

-continued

| | | | | | | | | | | |
|---|---|---|---|---|---|---|---|---|---|---|
| Silicone Quaternium-22 | — | — | 0.5% | — | — | — | — | 1.5% | — | — |
| PEG-12 Dimethicone | — | — | — | — | — | 1.5% | — | — | — | — |
| Dimethicone | — | — | 1.0% | — | 0.5% | — | — | — | — | — |
| Aminopropyl Dimethicone | — | — | — | — | 0.3% | — | — | — | — | — |
| Helianthus Annuus Oil | 0.1% | — | 0.2% | 0.1% | — | 0.1% | 0.3% | 0.2% | — | 0.1% |
| PEG-3 Distearate | — | — | 0.5% | — | — | 0.8% | — | 0.5% | — | — |
| Acrylates/C10-30 Alkyl Acrylate Crosspolymer | — | — | 0.2% | — | 0.5% | — | — | — | — | — |
| Sodium Hydroxide, 25% | — | — | 0.3% | — | 0.8% | — | — | — | — | — |
| Cocamide DEA | — | — | — | — | — | 2.5% | — | — | — | 0.5% |
| Cocamide MEA | — | — | — | 1.0% | — | — | — | 1.0% | — | — |
| Sodium Chloride | 0.4% | 0.7% | 0.1% | — | — | 1.5% | — | 2.0% | — | 1.2% |
| Propylene Glycol (and) PEG-55 Propylene Glycol Oleate | — | 2.5% | 2.0% | — | — | 0.3% | — | 0.6% | — | 0.2% |
| Xanthan Gum | 1.2% | — | — | 1.0% | 0.2% | — | 1.5% | 0.1% | 1.1% | — |
| Hydroxyethyl Cellulose | 0.1% | — | — | 0.1% | — | 0.1% | 0.1% | — | — | — |
| Benzophenone-4 | — | 0.1% | 0.2% | — | — | 0.2% | — | 0.2% | — | 0.1% |
| Menthol | 0.1% | — | — | — | — | — | — | — | — | 0.1% |
| Tetrasodium Glutamate Diacetate | — | 0.1% | — | 0.1% | 0.1% | — | 0.1% | 0.1% | — | 0.1% |
| Caffeine | 0.1% | — | 0.1% | — | — | — | — | 0.1% | — | — |
| Coumarin | 0.1% | — | — | 0.1% | 0.1% | — | 0.1% | 0.1% | — | 0.1% |
| Hydrolyzed Wheat Protein | 0.1% | — | 0.1% | 0.1% | — | — | 0.2% | 0.1% | 0.1% | 0.1% |
| Panthenol | 0.1% | 0.1% | — | 0.1% | 0.1% | 0.1% | 0.1% | — | 0.1% | 0.1% |
| Citric Acid | | | | | | ad pH | | | | |
| Parfums, Dyes, Preservatives | | | | | | q.s. | | | | |

| | XXI | XXII | XXIII | XIV | XXV | XXVI | XXVII | XXVIII | XXIX | XXX |
|---|---|---|---|---|---|---|---|---|---|---|
| Aqua | | | | | | ad 100% | | | | |
| Glucolipid | 6.0% | 4.0% | 3.5% | 1.0% | 3.0% | 3.0% | 4.0% | 2.0% | 2.5% | 5.0% |
| Sodium Coco-Sulfate | 3.0% | 1.0% | — | 5.0% | 3.0% | 3.0% | 2.0% | — | 2.5% | 3.0% |
| Glycolipids | 1.0% | | 1.5% | 1.0% | | 2.0% | | — | 2.0% | — |
| Lauryl Glucoside | — | 2.0% | — | — | | — | — | 2.0% | 3.5% | 2.0% |
| Sodium Cocoyl Glutamate | 1.0% | — | — | — | 3.0% | — | — | — | | — |
| Sodium Cocoyl Glycinate | — | — | 1.5% | — | — | — | — | 2.5% | 1.5% | — |
| Sodium C14-16 Olefin Sulfonate | | | | | 3.0% | | 2.0% | — | — | 2.0% |
| Lauroyl/Myristoyl Methyl Glucamide | — | 1.0% | — | 2.0% | — | | — | — | — | — |
| Cocamidopropyl Betaine | — | 2.0% | 1.5% | 4.0% | — | 2.0% | — | 7.5% | — | — |
| Sodium Cocoamphoacetate | — | 2.0% | 5.0% | — | 2.0% | 2.0% | 4.0% | — | — | — |
| Sucrose Cocoate | 1.0% | — | 1.5% | — | 1.5% | 1.0% | — | 1.0% | — | 3.5% |
| Glycerin | 0.5% | 0.5% | — | — | 0.3% | — | 0.2% | — | 0.5%- | — |
| Alcohol Denat. | — | — | 3.0% | — | — | 2.0% | — | — | — | — |
| Sorbitan Sesquicaprylate | 1.0% | — | 0.7% | 1.0% | | 0.5% | — | 0.5% | | 1.0% |
| Isostearamide MIPA; Glyceryl Laurate | — | 1.0% | — | — | — | 2.0% | — | — | — | 0.5% |
| Xanthan Gum | 1.0% | 0.7% | 0.5% | — | 0.7% | 0.3% | 0.7% | 0.5% | — | 0.5% |
| Chondrus Crispus | — | — | 1.5% | | 2.0% | 1.5% | 0.7% | — | — | 0.5% |
| Carrageenan | — | — | — | 1.0% | — | — | — | 0.3% | — | 0.5% |
| Hydroxypropyl Starch Phosphate | — | — | — | — | — | — | — | 4.5% | 5.5% | — |
| Guar Hydroxpropyltrimonium Chloride | 0.2% | — | 0.5% | 0.2% | 0.2% | 0.5% | 0.3% | 0.1% | — | — |
| Bis-(Isostearoyl/Oleyl Isopropyl) Dimonium Methosulfate | 0.5% | 0.5% | — | — | 0.5% | — | — | — | 0.5% | — |
| *Prunus Amygdalus Dulcis* (Almond) Oil | — | 0.1% | — | 0.1% | — | 0.05% | — | — | — | — |
| Lemon Oil | | — | 0.2% | — | 0.1% | | 0.2% | | | |
| Cellulose | 0.5% | — | — | — | 0.7% | — | 0.3% | 0.1% | — | 0.5% |
| Charcoal Powder | 1.0% | — | — | — | — | — | — | — | — | — |
| *Saccharum Officinarum* (Sugar Cane) Extract | — | — | — | 0.1% | — | 0.2% | — | — | — | — |
| Sodium Chloride | 0.7% | — | — | 0.5% | 1.0% | 0.7% | — | 2.0% | — | 1.2% |
| Polyglyceryl-6 Caprylate; Polyglyceryl-3 Cocoate; Polyglyceryl-4 Caprate; Polyglyceryl-6 Ricinoleate | | 3.0% | — | 4.0% | | 2.5% | — | | | |
| Caprylyl/Capryl Glucoside; Aqua, Sodium Cocoyl Glutamate; Glyceryl Caprylate; Ccitric Acid; Polyglyceryl-6 Oleate, Sodium Surfactin | | — | 3.0% | — | 1.0% | | 2.0% | | | |
| Tocopherol | — | 0.1% | — | 0.1% | — | 0.1% | 0.1% | — | 0.1% | — |
| Phytic Acid | 0.1% | 0.1% | — | — | — | — | — | 0.1% | 0.1% | — |
| Citric Acid | | | | | | ad pH | | | | |
| Parfums, Dyes, Preservatives | | | | | | q.s. | | | | |

-continued

| | XXXI | XXXII | XXXIII | XXXIV | XXXV | XXXVI | XXXVII | XXXVIII |
|---|---|---|---|---|---|---|---|---|
| Aqua | | | | ad 100% | | | | |
| Glucolipid | 1.0% | 1.5% | 2.0% | 1.5% | 3.0% | 2.5% | 4.0% | 5.0% |
| Capryl/ Capramidopropyl Betaine | — | 2.0% | — | — | 1.0% | — | 2.0% | |
| Glycolipids | 1.0% | — | — | — | 1.0% | — | — | |
| Decyl Glucoside | 1.0% | — | — | — | — | 2.0% | — | |
| Disodium Cocoamphodiacetate | — | — | 3.0% | 2.0% | — | — | 2.0% | |
| PEG-6 Caprylic/Capric Glycerides | 3.0% | 1.5% | — | — | — | — | — | 2.0% |
| Polyglyceryl-6 Caprylate; Polyglyceryl-4 Caprate | | — | 2.0% | — | — | 3.5% | — | |
| Polyglyceryl-6 Caprylate; Polyglyceryl-3 Cocoate; Polyglyceryl-4 Caprate; Polyglyceryl-6 Ricinoleate | — | 3.0% | | — | 4.0% | — | — | |
| Polyglyceryl-4 Caprate | — | — | | 2.5% | | — | — | |
| *Persea Gratissima* (Avocado) Oil | — | 0.1% | | — | 0.2% | — | 0.1% | 0.05% |
| Rosemary Oil | 0.1% | — | 0.05% | — | 0.1% | — | — | |
| Hydroxypropyl Methylcellulose | — | 0.5% | | — | — | — | 0.5% | |
| Sorbitan Sesquicaprylate | 0.3% | — | | 0.5% | — | 0.3% | 0.5% | 0.1% |
| Betaine | — | 0.5% | | 1.0% | — | 1.0% | — | 1.0% |
| Allantoin | — | — | 0.1% | — | 0.1% | | — | |
| Creatine | — | — | — | 0.1% | 0.05% | | — | 0.1% |
| Glycerin | 3.0% | 1.0% | — | — | — | 1.0% | 1.0% | — |
| Hexylene Glycol | 1.0% | — | 1.0% | — | 1.0% | 1.0% | — | — |
| Methylpropanediol; Caprylyl Glycol; Benzoic Acid | 1.2% | — | — | — | — | — | — | — |
| Benzyl Alcohol, Caprylyl Glycol, Benzoic Acid | — | 1.0% | 1.0% | 1.0% | 1.0% | — | — | — |
| Aqua, Sodium Levulinate, Sodium Benzoate | — | — | — | — | — | 1.0 | 1.0 | 1. |
| pH adjuster (Citric Acid or NaOH) | | | | ad pH | | | | |
| Preservatives, Parfum | | | | q.s. | | | | |

Example Formulations for Use in Household Care:

F1 to F5 Hand Dishwashing Formulations

| Ingredients | F1 | F2 | F3 | F4 | F5 |
|---|---|---|---|---|---|
| SLES | 8.4 | 8.4 | 21.0 | 0 | 0 |
| CAPB | 0 | 1.8 | 3.5 | 3.0 | 0 |
| Glucolipid | 3.6 | 1.8 | 3.5 | 9.0 | 9.0 |
| LAO | 0 | 0 | 0 | 0 | 3.0 |
| Thickener | 0.3 | 0.3 | 0 | 0.4 | 0.4 |
| Perfume | 0.2 | 0.2 | 0.1 | 0.1 | 0.1 |
| Dye | 0.01 | 0.01 | 0.01 | 0.01 | 0.01 |
| Water | to 100 | to 100 | to 100 | to 100 | to 100 |
| pH | 5.9 | 5.8 | 5.9 | 5.7 | 5.8 |

SLES = Texapon ® N 70 (trade name of BASF SE, sodium lauryl ether sulphate with 2 EO)
SL 18: Sophorolipid from Ecover was used, which has an acid to lactone ratio of 70:30 and a lactone form to oleic acid ratio of 60:1.
CAPB = Tego ® Betaine C 60 (trade name of Evonik Industries AG, cocoamidopropyl-betaine)
LAO = cocamine oxide. (OXIDET DM-246, trade name of Kao Chemicals)
Thickener: Keltro ®l T (Xanthan Gum, trade name of CP Kelco)

F6 to F9 Solid Dishwashing Formulations

| Raw materials | F6 | F7 | F8 | F9 |
|---|---|---|---|---|
| Sodium citrate 2 $H_2O$ | 39.4% | 39.7% | 39.7% | 35% |
| Sodium carbonate | 18.8% | 14.5% | 18.8% | 13.5% |
| Trilon ® M granules | 15% | 15% | 15% | 15% |
| Sodium percarbonate | 13.7% | 14% | 0% | 14% |
| Sokolan ® CP 50 granules | 6.5% | 6.5% | 6.5% | 6.5% |
| TAED | 4% | 4% | 4% | 4% |
| Sodium disilicate | 2% | 2% | 2% | 2% |
| Glucolipid | 0.3% | 4.3% | 0% | 0% |
| Glucolipid on Sipemat ® 22 | 0% | 0% | 0% | 10% |
| Sodium percarbonate coated with Glucolipid | 0% | 0% | 14% | 0% |

F10 Powder Detergent

| | |
|---|---|
| Glucolipid | 12.0% |
| Linear sodium alkylbenzenesulphonate | 5.3% |
| Fatty alcohol ethoxylate C12-18 (7 EO) | 2.0% |
| Sodium salts of fatty acids | 2.1% |
| Antifoam DC2-4248S | 5.0% |
| Zeolite 4A | 36.3% |
| Sodium carbonate | 14.9% |
| Sodium salt of acrylic-maleic acid copolymer (Sokalan CP5) | 3.1% |
| Sodium silicate | 3.8% |
| Carboxymethylcellulose | 1.5% |
| Dequest 2066 (Phosphonate) | 3.6% |
| Optical brighteners | 0.3% |
| Protease (Savinase 8.0) | 0.5% |
| Sodium perborate monohydrate | 1.0% |
| Sodium sulphate | Remainder |

F11 Liquid Detergent

| | |
|---|---|
| Glucolipid | 6.0% |
| Linear sodium alkylbenzenesulphonate | 4.0% |
| Fatty alcohol ethoxylate C12-18 (7 EO) | 5.0% |
| Fatty acid | 1.0% |
| Phosphonates | 0.5% |
| Propanediol | 5.0% |
| Protease (Alcalase ® 2.4 L FG) | 1% |
| 1,2-Benzisothiazoline-3-one ('BIT', e.g. "Proxel") | 100 ppm |
| Sodium hydroxide | --> pH 8.5 |
| Demineralized water | Remainder |

F12 Liquid Detergent Concentrate

| | |
|---|---|
| Glucolipid | 30.0% |
| Sodium lauryl ether sulphate | 10.0% |
| Linear sodium alkylbenzenesulphonate | 5.0% |
| Phosphonates | 0.5% |
| Sodium metaborate | 1.0% |
| Propanediol | 2.0% |
| Protease (Alcalase ® 2.4 L FG) | 1% |
| Lipase | 1% |
| Amylase | 1% |
| Fragrances | 0.5% |
| 1,2-Benzisothiazoline-3-one ('BIT', e.g. "Proxel") | 100 ppm |
| Sodium hydroxide | --> pH 8.5 |
| Demineralized water | Remainder |

F13 Laundry Formulation

| | |
|---|---|
| Glucolipid | 14.0% |
| linear alkyl benzene sulfonate | 14.0% |
| enzymes | 3.0% |
| MPG | 20% |
| TEA | 2.0% |
| Sodium citrate | 2.0% |
| Sodium chloride | 2.0% |
| Sodium hydroxide | 1.0% |
| Dispersant (e.g. polycarboxylate) | 1.0% |
| Friction based melamine formaldehyde based encapsulates: Aroma Ball Type 1 and Aroma Ball S-series ex Polychrom | 0.1% |
| water & foam control & other minors | Ad 100 |

The invention claimed is:

1. A mixture composition, comprising:

a glucolipid of formula (I) or a salt thereof formula (I)

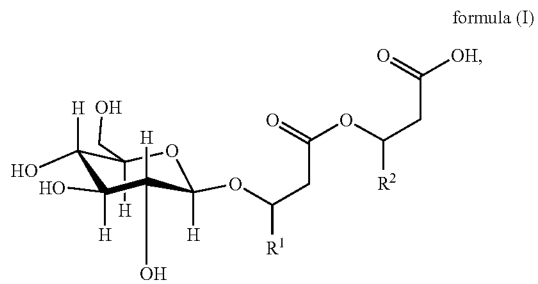

wherein $R^1$ and $R^2$=independently of one another, are an identical or different organic radical having from 2 to 24 carbon atoms, wherein the mixture composition comprises at least 60-90% by weight of a glucolipid GL-C10C10 of formula (I) with $R^1$ and $R^2$=$(CH_2)_6$—$CH_3$, wherein the percentages by weight refer to a sum of all of the glucolipids of formula (I) present, and wherein the mixture composition comprises from 5% by weight to 25% by weight of GL-C8C10, from 3% by weight to 17% by weight of GL-C10C12:1, from 2% by weight to 15% by weight of GL-C10C12, wherein the percentages by weight refer to the sum of all of the glucolipids of formula (I) present.

2. The mixture composition according to claim 1, wherein the mixture composition comprises from 0% by weight to 5% by weight of GL-C10, wherein the percentages by weight refer to the sum of all of the glucolipids of formula (I) present.

3. The mixture composition according to claim 1, wherein the mixture composition comprises at least 60% by weight of glucolipids of formula (I), wherein the percentages by weight refer to a total dry mass of the overall mixture composition.

4. A formulation comprising the mixture composition according to claim 1.

5. The formulation according to claim 4, comprising at least one further surfactant.

6. The formulation according to claim 5, wherein the total surfactant content of the formulation is from 5 to 60% by weight based on the total formulation.

7. A surface cleaner comprising the mixture composition according to claim 1.

8. The mixture composition according to claim 1, wherein the mixture composition comprises at least 80% by weight of glucolipids of formula (I), wherein the percentages by weight refer to a total dry mass of the overall mixture composition.

9. The mixture composition according to claim 1, wherein the mixture composition comprises at least 90% by weight of glucolipids of formula (I), wherein the percentages by weight refer to a total dry mass of the overall mixture composition.

10. The formulation according to claim 5, comprising a surfactant selected from the group consisting of anionic, nonionic, cationic, and amphoteric surfactants.

11. A surface cleaner comprising the formulation mixture according to claim 5.

12. The formulation according to claim 10, wherein the total surfactant content of the formulation is from 5 to 60% by weight based on the total formulation.

* * * * *

SEQUENCE LISTING

<160> NUMBER OF SEQ ID NOS: 8

<210> SEQ ID NO 1
<211> LENGTH: 1176
<212> TYPE: DNA
<213> ORGANISM: Serratia rubidaea ATCC 27593
<220> FEATURE:
<221> NAME/KEY: rbwB
<222> LOCATION: (1)..(1176)

<400> SEQUENCE: 1

```
atgagagtga taatatgcgc cctggggtcc tctggcgatg tttacccatg catcgaaatt      60

ggcgcgatat taaaagaaag aaaccatgat gtgcatatac ttaccaatga atacttcaaa     120

gattacgttg agtctcgcaa tctttccttt tcagcagtag gcagtaaaga ggactttatc     180

cgttcagtac gtgacagcca gctatgggag aagaaaacct cattaataaa aatatctgca     240

tacatggcta attatcaggt tggtatgttt cattcaatcg agaggttggt aaatgataat     300

tgtgtaatta ttcattctct ttgggtattc tcagccaagg tggttagcga aaaatattcg     360

ttaaaacgat tcccgataag ccttaccaac gccaacctta aactctgccc ggggaaattt     420

attagctggt tggaaagaaa gctcggcacc tcattgaacc tgaaggctga actctttaga     480

cgccgcctgg tttctccgct gttacaggag gtcatcgcct cgataagaaa atcagagaac     540

ctcccagccg ataaaaacat ctataccgac ctggtagata ggcgcttgaa tcctattatt     600

ttgtatgagc cttggttcta cgaaaaaaaa ccgcagcacg gattttatat ggggttcctg     660

ttaaataaaa accggacatt agaccacgct ccgataatca accgctttgt ggacaaaaaa     720

acggtggttt tcttcaccag ttgggcattg tctgatgaag caggcataaa tcatgtctta     780

agcagtctga aagatgaagg tttgaaatgt gtactggtca cccccaccct cgacagcatc     840
```

```
cacgttgaag aaaatgtcat cagaacacct taccttaata tggatagcat caaaggatgt    900

ctgtttgcca ttcaccacgg cggcatcggc accagtgccc aactgcttaa aaacggcata    960

cctcagttaa tctacccaaa agcctttgat cagttcgaaa acgcaagctc tctcgaaaga   1020

ataggctgtg gcgttaaagg cggcgatata aatgcgttga ggcatatgat taaaaagtcg   1080

gttaccaatg ataataactg tgctttttac gcctcgcggc taagtgaaga gaacaaagaa   1140

cgaaacgatg cgctggaacg tttactcatg ggttaa                             1176


<210> SEQ ID NO 2
<211> LENGTH: 391
<212> TYPE: PRT
<213> ORGANISM: Serratia rubidaea
<220> FEATURE:
<221> NAME/KEY: RbwB
<222> LOCATION: (1)..(391)

<400> SEQUENCE: 2

Met Arg Val Ile Ile Cys Ala Leu Gly Ser Ser Gly Asp Val Tyr Pro
1               5                   10                  15

Cys Ile Glu Ile Gly Ala Ile Leu Lys Glu Arg Asn His Asp Val His
            20                  25                  30

Ile Leu Thr Asn Glu Tyr Phe Lys Asp Tyr Val Glu Ser Arg Asn Leu
        35                  40                  45

Ser Phe Ser Ala Val Gly Ser Lys Glu Asp Phe Ile Arg Ser Val Arg
    50                  55                  60

Asp Ser Gln Leu Trp Glu Lys Lys Thr Ser Leu Ile Lys Ile Ser Ala
65                  70                  75                  80

Tyr Met Ala Asn Tyr Gln Val Gly Met Phe His Ser Ile Glu Arg Leu
                85                  90                  95

Val Asn Asp Asn Cys Val Ile Ile His Ser Leu Trp Val Phe Ser Ala
            100                 105                 110

Lys Val Val Ser Glu Lys Tyr Ser Leu Lys Arg Phe Pro Ile Ser Leu
        115                 120                 125

Thr Asn Ala Asn Leu Lys Leu Cys Pro Gly Lys Phe Ile Ser Trp Leu
    130                 135                 140

Glu Arg Lys Leu Gly Thr Ser Leu Asn Leu Lys Ala Glu Leu Phe Arg
145                 150                 155                 160

Arg Arg Leu Val Ser Pro Leu Leu Gln Glu Val Ile Ala Ser Ile Arg
                165                 170                 175

Lys Ser Glu Asn Leu Pro Ala Asp Lys Asn Ile Tyr Thr Asp Leu Val
            180                 185                 190

Asp Arg Arg Leu Asn Pro Ile Ile Leu Tyr Glu Pro Trp Phe Tyr Glu
        195                 200                 205

Lys Lys Pro Gln His Gly Phe Tyr Met Gly Phe Leu Leu Asn Lys Asn
    210                 215                 220

Arg Thr Leu Asp His Ala Pro Ile Ile Asn Arg Phe Val Asp Lys Lys
225                 230                 235                 240

Thr Val Val Phe Phe Thr Ser Trp Ala Leu Ser Asp Glu Ala Gly Ile
                245                 250                 255

Asn His Val Leu Ser Ser Leu Lys Asp Glu Gly Leu Lys Cys Val Leu
            260                 265                 270

Val Thr Pro Thr Leu Asp Ser Ile His Val Glu Glu Asn Val Ile Arg
        275                 280                 285

Thr Pro Tyr Leu Asn Met Asp Ser Ile Lys Gly Cys Leu Phe Ala Ile
```

```
    290                 295                 300

His His Gly Gly Ile Gly Thr Ser Ala Gln Leu Leu Lys Asn Gly Ile
305                 310                 315                 320

Pro Gln Leu Ile Tyr Pro Lys Ala Phe Asp Gln Phe Glu Asn Ala Ser
                325                 330                 335

Ser Leu Glu Arg Ile Gly Cys Gly Val Lys Gly Gly Asp Ile Asn Ala
            340                 345                 350

Leu Arg His Met Ile Lys Lys Ser Val Thr Asn Asp Asn Asn Cys Ala
        355                 360                 365

Phe Tyr Ala Ser Arg Leu Ser Glu Glu Asn Lys Glu Arg Asn Asp Ala
    370                 375                 380

Leu Glu Arg Leu Leu Met Gly
385                 390


<210> SEQ ID NO 3
<211> LENGTH: 888
<212> TYPE: DNA
<213> ORGANISM: Pseudomonas aeruginosa
<220> FEATURE:
<221> NAME/KEY: rhamnosyltransferase 1, rhlA
<222> LOCATION: (1)..(888)

<400> SEQUENCE: 3

atgcggcgcg aaagtctgtt ggtatcggtt tgcaagggcc tgcgggtaca tgtcgagcgc     60

gttgggcagg atcccgggcg cagcacggtg atgctggtca acggcgcgat ggcgaccacc    120

gcctcgttcg cccggacctg caagtgcctg gccgaacatt tcaacgtggt gctgttcgac    180

ctgcccttcg ccgggcagtc gcgtcagcac aacccgcagc gggggttgat caccaaggac    240

gacgaggtgg aaatcctcct ggcgctgatc gagcgcttcg aggtcaatca cctggtctcc    300

gcgtcctggg gcggtatctc cacgctgctg gcgctgtcgc gcaatccgcg cggcatccgc    360

agctcggtgg tgatggcatt cgcccctgga ctgaaccagg cgatgctcga ctacgtcggg    420

cgggcgcagg cgctgatcga gctggacgac aagtcggcga tcggccatct gctcaacgag    480

accgtcggca aatacctgcc gccgcgcctg aaagccagca accatcagca catggcttcg    540

ctggccaccg gcgaatacga gcaggcgcgc tttcacatcg accaggtgct ggcgctcaac    600

gatcggggct acctggcttg cctggagcgg atccagagcc acgtgcattt catcaacggc    660

agctgggacg aatacaccac cgccgaggac gcccgccagt tccgcgacta cctgccgcac    720

tgcagtttct cgcgggtgga gggcaccggg catttcctcg acctggagtc caagctggcc    780

gcggtacgcg tgcaccgcgc cctgctcgag cacctgctga agcaaccgga gccgcagcgg    840

gcggaacgcg cggcgggatt ccacgagatg gccatcggct acgcctga                  888


<210> SEQ ID NO 4
<211> LENGTH: 295
<212> TYPE: PRT
<213> ORGANISM: Pseudomonas aeruginosa
<220> FEATURE:
<221> NAME/KEY: RhlA
<222> LOCATION: (1)..(295)

<400> SEQUENCE: 4

Met Arg Arg Glu Ser Leu Leu Val Ser Val Cys Lys Gly Leu Arg Val
1               5                   10                  15

His Val Glu Arg Val Gly Gln Asp Pro Gly Arg Ser Thr Val Met Leu
            20                  25                  30

Val Asn Gly Ala Met Ala Thr Thr Ala Ser Phe Ala Arg Thr Cys Lys
```

```
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Glu Val Asn
                85                  90                  95

His Leu Val Ser Ala Ser Trp Gly Gly Ile Ser Thr Leu Leu Ala Leu
            100                 105                 110

Ser Arg Asn Pro Arg Gly Ile Arg Ser Ser Val Val Met Ala Phe Ala
        115                 120                 125

Pro Gly Leu Asn Gln Ala Met Leu Asp Tyr Val Gly Arg Ala Gln Ala
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
    210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Val Arg Val His Arg Ala Leu Leu Glu His Leu
            260                 265                 270

Leu Lys Gln Pro Glu Pro Gln Arg Ala Glu Arg Ala Ala Gly Phe His
        275                 280                 285

Glu Met Ala Ile Gly Tyr Ala
    290                 295
```

<210> SEQ ID NO 5
<211> LENGTH: 2028
<212> TYPE: DNA
<213> ORGANISM: Artificial Sequence
<220> FEATURE:
<223> OTHER INFORMATION: Promoter cassette Prha

<400> SEQUENCE: 5

```
ttaatctttc tgcgaattga gatgacgcca ctggctgggc gtcatcccgg tttcccgggt     60

aaacaccacc gaaaaatagt tactatcttc aaagccacat tcggtcgaaa tatcactgat    120

taacaggcgg ctatgctgga gaagatattg cgcatgacac actctgacct gtcgcagata    180

ttgattgatg gtcattccag tctgctggcg aaattgctga cgcaaaacgc gctcactgca    240

cgatgcctca tcacaaaatt tatccagcgc aaagggactt ttcaggctag ccgccagccg    300

ggtaatcagc ttatccagca acgtttcgct ggatgttggc ggcaacgaat cactggtgta    360

acgatggcga ttcagcaaca tcaccaactg cccgaacagc aactcagcca tttcgttagc    420

aaacggcaca tgctgactac tttcatgctc aagctgaccg ataacctgcc gcgcctgcgc    480

catccccatg ctacctaagc gccagtgtgg ttgccctgcg ctggcgttaa atcccggaat    540

cgccccctgc cagtcaagat tcagcttcag acgctccggg caataaataa tattctgcaa    600
```

```
aaccagatcg ttaacggaag cgtaggagtg tttatcgtca gcatgaatgt aaaagagatc    660

gccacgggta atgcgataag ggcgatcgtt gagtacatgc aggccattac cgcgccagac    720

aatcaccagc tcacaaaaat catgtgtatg ttcagcaaag acatcttgcg gataacggtc    780

agccacagcg actgcctgct ggtcgctggc aaaaaaatca tctttgagaa gttttaactg    840

atgcgccacc gtggctacct cggccagaga acgaagttga ttattcgcaa tatggcgtac    900

aaatacgttg agaagattcg cgttattgca gaaagccatc ccgtccctgg cgaatatcac    960

gcggtgacca gttaaactct cggcgaaaaa gcgtcgaaaa gtggttactg tcgctgaatc   1020

cacagcgata ggcgatgtca gtaacgctgg cctcgctgtg gcgtagcaga tgtcgggctt   1080

tcatcagtcg caggcggttc aggtatcgct gaggcgtcag tcccgtttgc tgcttaagct   1140

gccgatgtag cgtacgcagt gaaagagaaa attgatccgc cacggcatcc caattcacct   1200

catcggcaaa atggtcctcc agccaggcca gaagcaagtt gagacgtgat gcgctgtttt   1260

ccaggttctc ctgcaaactg cttttacgca gcaagagcag taattgcata aacaagatct   1320

cgcgactggc ggtcgagggt aaatcatttt ccccttcctg ctgttccatc tgtgcaacca   1380

gctgtcgcac ctgctgcaat acgctgtggt taacgcgcca gtgagacgga tactgcccat   1440

ccagctcttg tggcagcaac tgattcagcc cggcgagaaa ctgaaatcga tccggcgagc   1500

gatacagcac attggtcaga cacagattat cggtatgttc atacagatgc cgatcatgat   1560

cgcgtacgaa acagaccgtg ccaccggtga tggtataggg ctgcccatta aacacatgaa   1620

tacccgtgcc atgttcgaca atcacaattt catgaaaatc atgatgatgt tcaggaaaat   1680

ccgcctgcgg gagccggggt tctatcgcca cggacgcgtt accagacgga aaaaaatcca   1740

cactatgtaa tacggtcata ctggcctcct gatgtcgtca acacggcgaa atagtaatca   1800

cgaggtcagg ttcttacctt aaattttcga cggaaaacca cgtaaaaaac gtcgattttt   1860

caagatacag cgtgaatttt caggaaatgc ggtgagcatc acatcaccac aattcagcaa   1920

attgtgaaca tcatcacgtt catctttccc tggttgccaa tggcccattt tcctgtcagt   1980

aacgagaagg tcgcgaattc aggcgctttt tagactggtc gtaatgaa               2028
```

<210> SEQ ID NO 6
<211> LENGTH: 107
<212> TYPE: DNA
<213> ORGANISM: Artificial Sequence
<220> FEATURE:
<223> OTHER INFORMATION: Terminator sequence

<400> SEQUENCE: 6

```
caaataaaac gaaaggctca gtcgaaagac tgggcctttc gttttatctg ttgtttgtcg     60

gtgaacgctc tcctgagtag gacaaatccg ccgggagcgg atttgaa                  107
```

<210> SEQ ID NO 7
<211> LENGTH: 2132
<212> TYPE: DNA
<213> ORGANISM: Artificial Sequence
<220> FEATURE:
<223> OTHER INFORMATION: Synthetical operon rhlA_Pa rbwB_Srub

<400> SEQUENCE: 7

```
tttgggaggt gtgaaatgcg gcgcgaaagt ctgttggtat cggtttgcaa gggcctgcgg     60

gtacatgtcg agcgcgttgg gcaggatccc gggcgcagca cggtgatgct ggtcaacggc    120

gcgatggcga ccaccgcctc gttcgcccgg acctgcaagt gcctggccga acatttcaac    180
```

```
gtggtgctgt tcgacctgcc cttcgccggg cagtcgcgtc agcacaaccc gcagcggggg    240
ttgatcacca aggacgacga ggtggaaatc ctcctggcgc tgatcgagcg cttcgaggtc    300
aatcacctgg tctccgcgtc ctggggcggt atctccacgc tgctggcgct gtcgcgcaat    360
ccgcgcggca tccgcagctc ggtggtgatg gcattcgccc ctggactgaa ccaggcgatg    420
ctcgactacg tcgggcgggc gcaggcgctg atcgagctgg acgacaagtc ggcgatcggc    480
catctgctca acgagaccgt cggcaaatac ctgccgccgc gcctgaaagc cagcaaccat    540
cagcacatgg cttcgctggc caccggcgaa tacgagcagg cgcgctttca catcgaccag    600
gtgctggcgc tcaacgatcg ggctacctg gcttgcctgg agcggatcca gagccacgtg     660
catttcatca acggcagctg ggacgaatac accaccgccg aggacgcccg ccagttccgc    720
gactacctgc cgcactgcag tttctcgcgg gtggagggca ccgggcattt cctcgacctg    780
gagtccaagc tggccgcggt acgcgtgcac cgcgccctgc tcgagcacct gctgaagcaa    840
ccggagccgc agcgggcgga acgcgcggcg ggattccacg agatggccat cggctacgcc    900
tgaggataac aaactaaaat attgattcga caagacagga tggtgatatg agagtgataa    960
tatgcgccct ggggtcctct ggcgatgttt acccatgcat cgaaattggc gcgatattaa   1020
aagaaagaaa ccatgatgtg catatactta ccaatgaata cttcaaagat tacgttgagt   1080
ctcgcaatct ttccttttca gcagtaggca gtaaagagga ctttatccgt tcagtacgtg   1140
acagccagct atgggagaag aaaacctcat taataaaaat atctgcatac atggctaatt   1200
atcaggttgg tatgtttcat tcaatcgaga ggttggtaaa tgataattgt gtaattattc   1260
attctctttg ggtattctca gccaaggtgg ttagcgaaaa atattcgtta aaacgattcc   1320
cgataagcct taccaacgcc aaccttaaac tctgcccggg gaaatttatt agctggttgg   1380
aaagaaagct cggcacctca ttgaacctga aggctgaact ctttagacgc cgcctggttt   1440
ctccgctgtt acaggaggtc atcgcctcga taagaaaatc agagaacctc ccagccgata   1500
aaaacatcta taccgacctg gtagataggc gcttgaatcc tattattttg tatgagcctt   1560
ggttctacga aaaaaaaccg cagcacggat tttatatggg gttcctgtta aataaaaacc   1620
ggacattaga ccacgctccg ataatcaacc gctttgtgga caaaaaaacg gtggttttct   1680
tcaccagttg ggcattgtct gatgaagcag gcataaatca tgtcttaagc agtctgaaag   1740
atgaaggttt gaaatgtgta ctggtcaccc ccaccctcga cagcatccac gttgaagaaa   1800
atgtcatcag aacaccttac cttaatatgg atagcatcaa aggatgtctg tttgccattc   1860
accacggcgg catcggcacc agtgcccaac tgcttaaaaa cggcatacct cagttaatct   1920
acccaaaagc ctttgatcag ttcgaaaacg caagctctct cgaaagaata ggctgtggcg   1980
ttaaaggcgg cgatataaat gcgttgaggc atatgattaa aaagtcggtt accaatgata   2040
ataactgtgc tttttacgcc tcgcggctaa gtgaagagaa caaagaacga aacgatgcgc   2100
tggaacgttt actcatgggt taagctcgag ca                                 2132
```

<210> SEQ ID NO 8
<211> LENGTH: 10787
<212> TYPE: DNA
<213> ORGANISM: Artificial Sequence
<220> FEATURE:
<223> OTHER INFORMATION: Plasmid pACYC_rhlA_Pa rbwB_Srub

<400> SEQUENCE: 8

```
tcaggcgggc aagaatgtga ataaaggccg gataaaactt gtgcttattt ttctttacgg     60
tctttaaaaa ggccgtaata tccagctgaa cggtctggtt ataggtacat tgagcaactg    120
```

```
actgaaatgc ctcaaaatgt tctttacgat gccattggga tatatcaacg gtggtatatc    180
cagtgatttt tttctccatt ttagcttcct tagctcctga aaatctcgat aactcaaaaa    240
atacgcccgg tagtgatctt atttcattat ggtgaaagtt ggaacctctt acgtgccgat    300
caacgtctca ttttcgccaa aagttggccc agggcttccc ggtatcaaca gggacaccag    360
gatttattta ttctgcgaag tgatcttccg tcacaggtat ttattcggcg caaagtgcgt    420
cgggtgatgc tgccaactta ctgatttagt gtatgatggt gtttttgagg tgctccagtg    480
gcttctgttt ctatcagctg tccctcctgt tcagctactg acggggtggt gcgtaacggc    540
aaaagcaccg ccggacatca gcgctagcgg agtgtatact ggcttactat gttggcactg    600
atgagggtgt cagtgaagtg cttcatgtgg caggagaaaa aaggctgcac cggtgcgtca    660
gcagaatatg tgatacagga tatattccgc ttcctcgctc actgactcgc tacgctcggt    720
cgttcgactg cggcgagcgg aaatggctta cgaacggggc ggagatttcc tggaagatgc    780
caggaagata cttaacaggg aagtgagagg gccgcggcaa agccgttttt ccataggctc    840
cgcccccctg acaagcatca cgaaatctga cgctcaaatc agtggtggcg aaacccgaca    900
ggactataaa gataccaggc gtttccccct ggcggctccc tcgtgcgctc tcctgttcct    960
gcctttcggt ttaccggtgt cattccgctg ttatggccgc gtttgtctca ttccacgcct   1020
gacactcagt tccgggtagg cagttcgctc caagctggac tgtatgcacg aaccccccgt   1080
tcagtccgac cgctgcgcct tatccggtaa ctatcgtctt gagtccaacc cggaaagaca   1140
tgcaaaagca ccactggcag cagccactgg taattgattt agaggagtta gtcttgaagt   1200
catgcgccgg ttaaggctaa actgaaagga caagttttgg tgactgcgct cctccaagcc   1260
agttacctcg gttcaaagag ttggtagctc agagaacctt cgaaaaaccg ccctgcaagg   1320
cggttttttc gttttcagag caagagatta cgcgcagacc aaaacgatct caagaagatc   1380
atcttattaa tcagataaaa tatttctaga tttcagtgca atttatctct tcaaatgtag   1440
cacctgaagt cagccccata cgatataagt tgtaattctc atgtttgaca gcttatcatc   1500
gataagcttt aatgcggtag tttatcacag ttaaattgct aacgcagtca ggcaccgtgt   1560
atgattgaac aagatggatt gcacgcaggt tctccggccg cttgggtgga gaggctattc   1620
ggctatgact gggcacaaca gacaatcggc tgctctgatg ccgccgtgtt ccggctgtca   1680
gcgcaggggc gcccggttct ttttgtcaag accgacctgt ccggtgccct gaatgaactg   1740
caggacgagg cagcgcggct atcgtggctg gccacgacgg gcgttccttg cgcagctgtg   1800
ctcgacgttg tcactgaagc gggaagggac tggctgctat tgggcgaagt gccggggcag   1860
gatctcctgt catctcacct tgctcctgcc gagaaagtat ccatcatggc tgatgcaatg   1920
cggcggctgc atacgcttga tccggctacc tgcccattcg accaccaagc gaaacatcgc   1980
atcgagcgag cacgtactcg gatggaagcc ggtcttgtcg atcaggatga tctggacgaa   2040
gagcatcagg ggctcgcgcc agccgaactg ttcgccaggc tcaaggcgcg catgcccgac   2100
ggcgaggatc tcgtcgtgac ccatggcgat gcctgcttgc cgaatatcat ggtggaaaat   2160
ggccgctttt ctggattcat cgactgtggc cggctgggtg tggcggaccg ctatcaggac   2220
atagcgttgg ctacccgtga tattgctgaa gagcttggcg gcgaatgggc tgaccgcttc   2280
ctcgtgcttt acggtatcgc cgctcccgat tcgcagcgca tcgccttcta tcgccttctt   2340
gacgagttca tggaagccgg cggcacctcg ctaacggatt caccactcca agaattggag   2400
ccaatcaatt cttgcggaga actgtgaatg cgcaaaccaa cccttggcag aacatatcca   2460
```

-continued

```
tcgcgtccgc catctccagc agccgcacgc ggcgcatctc gggcagcgtt gggtcctggc   2520
cacgggtgcg catgatcgtg ctcctgtcgt tgaggacccg gctaggctgg cggggttgcc   2580
ttactggtta gcagaatgaa tcaccgatac gcgagcgaac gtgaagcgac tgctgctgca   2640
aaacgtctgc gacctgagca acaacatgaa tggtcttcgg tttccgtgtt tcgtaaagtc   2700
tggaaacgcg gaagtcccct acgtgctgct gaagttgccc gcaacagaga gtggaaccaa   2760
ccggtgatac cacgatacta tgactgagag tcaacgccat gagcggcctc atttcttatt   2820
ctgagttaca acagtccgca ccgctgtccg gtagctcctt ccggtgggcg cggggcatga   2880
ctatcgtcgc cgcacttatg actgtcttct ttatcatgca actcgtagga caggtgccgg   2940
cagcgcccaa cagtcccccg gccacggggc ctgccaccat acccacgccg aaacaagcgc   3000
cctgcaccat tatgttccgg atctgcatcg caggatgctg ctggctaccc tgtggaacac   3060
ctacatctgt attaacgaag cgctaaccgt ttttatcagg ctctgggagg cagaataaat   3120
gatcatatcg tcaattatta cctccacggg gagagcctga gcaaactggc ctcaggcatt   3180
tgagaagcac acggtcacac tgcttccggt agtcaataaa ccggtaaacc agcaatagac   3240
ataagcggct atttaacgac cctgccctga accgacgacc gggtcgaatt tgctttcgaa   3300
tttctgccat tcatccgctt attatcactt attcaggcgt agcaccaggc gtttaagggc   3360
accaataact gccttaaaaa aattacgccc cgccctgcca ctcatcgcag tactgttgta   3420
attcattaag cattctgccg acatggaagc catcacaaac ggcatgatga acctgaatcg   3480
ccagcggcat cagcaccttg tcgccttgcg tataatattt gcccatggat ttaaatttaa   3540
tctttctgcg aattgagatg acgccactgg ctgggcgtca tcccggtttc ccgggtaaac   3600
accaccgaaa aatagttact atcttcaaag ccacattcgg tcgaaatatc actgattaac   3660
aggcggctat gctggagaag atattgcgca tgacacactc tgacctgtcg cagatattga   3720
ttgatggtca ttccagtctg ctggcgaaat tgctgacgca aaacgcgctc actgcacgat   3780
gcctcatcac aaaatttatc cagcgcaaag ggacttttca ggctagccgc cagccgggta   3840
atcagcttat ccagcaacgt ttcgctggat gttggcggca acgaatcact ggtgtaacga   3900
tggcgattca gcaacatcac caactgcccg aacagcaact cagccatttc gttagcaaac   3960
ggcacatgct gactactttc atgctcaagc tgaccgataa cctgccgcgc ctgcgccatc   4020
cccatgctac ctaagcgcca gtgtggttgc cctgcgctgg cgttaaatcc cggaatcgcc   4080
ccctgccagt caagattcag cttcagacgc tccgggcaat aaataatatt ctgcaaaacc   4140
agatcgttaa cggaagcgta ggagtgttta tcgtcagcat gaatgtaaaa gagatcgcca   4200
cgggtaatgc gataagggcg atcgttgagt acatgcaggc cattaccgcg ccagacaatc   4260
accagctcac aaaaatcatg tgtatgttca gcaaagacat cttgcggata acggtcagcc   4320
acagcgactg cctgctggtc gctggcaaaa aaatcatctt tgagaagttt taactgatgc   4380
gccaccgtgg ctacctcggc cagagaacga agttgattat tcgcaatatg gcgtacaaat   4440
acgttgagaa gattcgcgtt attgcagaaa gccatcccgt ccctggcgaa tatcacgcgg   4500
tgaccagtta aactctcggc gaaaaagcgt cgaaaagtgg ttactgtcgc tgaatccaca   4560
gcgataggcg atgtcagtaa cgctggcctc gctgtggcgt agcagatgtc gggctttcat   4620
cagtcgcagg cggttcaggt atcgctgagg cgtcagtccc gtttgctgct taagctgccg   4680
atgtagcgta cgcagtgaaa gagaaaattg atccgccacg gcatcccaat tcacctcatc   4740
ggcaaaatgg tcctccagcc aggccagaag caagttgaga cgtgatgcgc tgttttccag   4800
gttctcctgc aaactgcttt tacgcagcaa gagcagtaat tgcataaaca agatctcgcg   4860
```

```
actggcggtc gagggtaaat cattttcccc ttcctgctgt tccatctgtg caaccagctg   4920
tcgcacctgc tgcaatacgc tgtggttaac gcgccagtga gacggatact gcccatccag   4980
ctcttgtggc agcaactgat tcagcccggc gagaaactga aatcgatccg gcgagcgata   5040
cagcacattg gtcagacaca gattatcggt atgttcatac agatgccgat catgatcgcg   5100
tacgaaacag accgtgccac cggtgatggt atagggctgc ccattaaaca catgaatacc   5160
cgtgccatgt tcgacaatca caatttcatg aaaatcatga tgatgttcag gaaaatccgc   5220
ctgcgggagc cggggttcta tcgccacgga cgcgttacca gacggaaaaa aatccacact   5280
atgtaatacg gtcatactgg cctcctgatg tcgtcaacac ggcgaaatag taatcacgag   5340
gtcaggttct taccttaaat tttcgacgga aaccacgta aaaaacgtcg atttttcaag   5400
atacagcgtg aattttcagg aaatgcggtg agcatcacat caccacaatt cagcaaattg   5460
tgaacatcat cacgttcatc tttccctggt tgccaatggc ccattttcct gtcagtaacg   5520
agaaggtcgc gaattcaggc gctttttaga ctggtcgtaa tgaacattta aatgaattcc   5580
cttgggactc tagagatccg cgggggccca ggaggggga tctggcattt ttgggaggtg   5640
tgaaatgcgg cgcgaaagtc tgttggtatc ggtttgcaag ggcctgcggg tacatgtcga   5700
gcgcgttggg caggatcccg ggcgcagcac ggtgatgctg gtcaacggcg cgatggcgac   5760
caccgcctcg ttcgcccgga cctgcaagtg cctggccgaa catttcaacg tggtgctgtt   5820
cgacctgccc ttcgccgggc agtcgcgtca gcacaacccg cagcgggggt tgatcaccaa   5880
ggacgacgag gtggaaatcc tcctggcgct gatcgagcgc ttcgaggtca atcacctggt   5940
ctccgcgtcc tggggcggta tctccacgct gctggcgctg tcgcgcaatc cgcgcggcat   6000
ccgcagctcg gtggtgatgg cattcgcccc tggactgaac caggcgatgc tcgactacgt   6060
cgggcgggcg caggcgctga tcgagctgga cgacaagtcg gcgatcggcc atctgctcaa   6120
cgagaccgtc ggcaaatacc tgccgccgcg cctgaaagcc agcaaccatc agcacatggc   6180
ttcgctggcc accggcgaat acgagcaggc gcgctttcac atcgaccagg tgctggcgct   6240
caacgatcgg ggctacctgg cttgcctgga gcggatccag agccacgtgc atttcatcaa   6300
cggcagctgg gacgaataca ccaccgccga ggacgcccgc cagttccgcg actacctgcc   6360
gcactgcagt ttctcgcggg tggagggcac cgggcatttc ctcgacctgg agtccaagct   6420
ggccgcggta cgcgtgcacc gcgccctgct cgagcacctg ctgaagcaac cggagccgca   6480
gcgggcggaa cgcgcggcgg gattccacga gatggccatc ggctacgcct gaggataaca   6540
aactaaaata ttgattcgac aagacaggat ggtgatatga gagtgataat atgcgccctg   6600
gggtcctctg gcgatgttta cccatgcatc gaaattggcg cgatattaaa agaaagaaac   6660
catgatgtgc atatacttac caatgaatac ttcaaagatt acgttgagtc tcgcaatctt   6720
tccttttcag cagtaggcag taaagaggac tttatccgtt cagtacgtga cagccagcta   6780
tgggagaaga aaacctcatt aataaaaata tctgcataca tggctaatta tcaggttggt   6840
atgtttcatt caatcgagag gttggtaaat gataattgtg taattattca ttctctttgg   6900
gtattctcag ccaaggtggt tagcgaaaaa tattcgttaa aacgattccc gataagcctt   6960
accaacgcca accttaaact ctgcccgggg aaatttatta gctggttgga aagaaagctc   7020
ggcacctcat tgaacctgaa ggctgaactc tttagacgcc gcctggtttc tccgctgtta   7080
caggaggtca tcgcctcgat aagaaaatca gagaacctcc cagccgataa aaacatctat   7140
accgacctgg tagataggcg cttgaatcct attattttgt atgagccttg gttctacgaa   7200
```

```
aaaaaaccgc agcacggatt ttatatgggg ttcctgttaa ataaaaaccg gacattagac   7260
cacgctccga taatcaaccg ctttgtggac aaaaaaacgg tggttttctt caccagttgg   7320
gcattgtctg atgaagcagg cataaatcat gtcttaagca gtctgaaaga tgaaggtttg   7380
aaatgtgtac tggtcacccc caccctcgac agcatccacg ttgaagaaaa tgtcatcaga   7440
acaccttacc ttaatatgga tagcatcaaa ggatgtctgt ttgccattca ccacggcggc   7500
atcggcacca gtgcccaact gcttaaaaac ggcatacctc agttaatcta cccaaaagcc   7560
tttgatcagt tcgaaaacgc aagctctctc gaaagaatag gctgtggcgt taaaggcggc   7620
gatataaatg cgttgaggca tatgattaaa aagtcggtta ccaatgataa taactgtgct   7680
ttttacgcct cgcggctaag tgaagagaac aaagaacgaa acgatgcgct ggaacgttta   7740
ctcatgggtt aagctcgagc acgcgagagt agggaactgc caggcatcaa ataaaacgaa   7800
aggctcagtc gaaagactgg gcctttcgtt ttatctgttg tttgtcggtg aacgctctcc   7860
tgagtaggac aaatccgccg ggagcggatt tgaacgatga taagctgtca aacatgagaa   7920
ttcttgaaga cgaaagggcc tcgtgtgtac aaacgttcgt caaaagggcg acacaaaatt   7980
cctgcagggg ccggcccagc gccggcggtc gagtggcgac ggcgcggctt gtccgcgccc   8040
tggtagattg cctggccgta ggccagccat ttttgagcgg ccagcggccg cgataggccg   8100
acgcgaagcg gcggggcgta gggagcgcag cgaccgaagg gtaggcgctt tttgcagctc   8160
ttcggctgtg cgctggccag acagttatgc acaggccagg cgggttttaa gagttttaat   8220
aagttttaaa gagttttagg cggaaaaatc gccttttttc tcttttatat cagtcactta   8280
catgtgtgac cggttcccaa tgtacggctt tgggttccca atgtacgggt tccggttccc   8340
aatgtacggc tttgggttcc caatgtacgt gctatccaca ggaaagagac cttttcgacc   8400
tttttcccct gctagggcaa tttgccctag catctgctcc gtacattagg aaccggcgga   8460
tgcttcgccc tcgatcaggt tgcggtagcg catgactagg atcgggccag cctgccccgc   8520
ctcctccttc aaatcgtact ccggcaggtc atttgacccg atcagcttgc gcacggtgaa   8580
acagaacttc ttgaactctc cggcgctgcc actgcgttcg tagatcgtct tgaacaacca   8640
tctggcttct gccttgcctg cggcgcggcg tgccaggcgg tagagaaaac ggccgatgcc   8700
gggatcgatc aaaaagtaat cggggtgaac cgtcagcacg tccgggttct tgccttctgt   8760
gatctcgcgg tacatccaat caactagctc gatctcgatg tactccggcc gcccggtttc   8820
gctctttacg atcttgtagc ggctaatcaa ggcttcaccc tcggataccg tcaccaggcg   8880
gccgttcttg gccttcttcg tacgctgcat ggcaacgtgc gtggtgttta accgaatgca   8940
ggtttctacc aggtcgtctt tctgctttcc gccatcggct cgccggcaga acttgagtac   9000
gtccgcaacg tgtggacgga acacgcggcc gggcttgtct cccttccctt cccggtatcg   9060
gttcatggat tcggttagat gggaaaccgc catcagtacc aggtcgtaat cccacacact   9120
ggccatgccg gccggccctg cggaaacctc tacgtgcccg tctggaagct cgtagcggat   9180
cacctcgcca gctcgtcggt cacgcttcga cagacggaaa acggccacgt ccatgatgct   9240
gcgactatcg cgggtgccca cgtcatagag catcggaacg aaaaaatctg gttgctcgtc   9300
gcccttgggc ggcttcctaa tcgacggcgc accggctgcc ggcggttgcc gggattcttt   9360
gcggattcga tcagcggccg cttgccacga ttcaccgggg cgtgcttctg cctcgatgcg   9420
ttgccgctgg gcggcctgcg cggccttcaa cttctccacc aggtcatcac ccagcgccgc   9480
gccgatttgt accgggccgg atggtttgcg accgctcacg ccgattcctc gggcttgggg   9540
gttccagtgc cattgcaggg ccggcagaca acccagccgc ttacgcctgg ccaaccgccc   9600
```

-continued

```
gttcctccac acatggggca ttccacggcg tcggtgcctg gttgttcttg attttccatg   9660

ccgcctcctt tagccgctaa aattcatcta ctcatttatt catttgctca tttactctgg   9720

tagctgcgcg atgtattcag atagcagctc ggtaatggtc ttgccttggc gtaccgcgta   9780

catcttcagc ttggtgtgat cctccgccgg caactgaaag ttgacccgct tcatggctgg   9840

cgtgtctgcc aggctggcca acgttgcagc cttgctgctg cgtgcgctcg gacggccggc   9900

acttagcgtg tttgtgcttt tgctcatttt ctctttacct cattaactca aatgagtttt   9960

gatttaattt cagcggccag cgcctggacc tcgcgggcag cgtcgccctc gggttctgat  10020

tcaagaacgg ttgtgccggc ggcggcagtg cctgggtagc tcacgcgctg cgtgatacgg  10080

gactcaagaa tgggcagctc gtacccggcc agcgcctcgg caacctcacc gccgatgcgc  10140

gtgcctttga tcgcccgcga cacgacaaag gccgcttgta gccttccatc cgtgacctca  10200

atgcgctgct taaccagctc caccaggtcg gcggtggccc atatgtcgta agggcttggc  10260

tgcaccggaa tcagcacgaa gtcggctgcc ttgatcgcgg acacagccaa gtccgccgcc  10320

tggggcgctc cgtcgatcac tacgaagtcg cgccggccga tggccttcac gtcgcggtca  10380

atcgtcgggc ggtcgatgcc gacaacggtt agcggttgat cttcccgcac ggccgcccaa  10440

tcgcgggcac tgccctgggg atcggaatcg actaacagaa catcggcccc ggcgagttgc  10500

agggcgcggg ctagatgggt tgcgatggtc gtcttgcctg acccgccttt ctggttaagt  10560

acagcgataa ccttcatgcg ttccccttgc gtatttgttt atttactcat cgcatcatat  10620

acgcagcgac cgcatgacgc aagctgtttt actcaaatac acatcacctt tttagacggc  10680

ggcgctcggt ttcttcagcg gccaagctgg ccggccaggc cgccagcttg gcatcagaca  10740

aaccggccag gatttcatgc agccgcacgg ttccggatga gcattca                10787
```